(12) United States Patent
Osbourn et al.

(10) Patent No.: US 7,982,096 B2
(45) Date of Patent: Jul. 19, 2011

(54) ROOT SPECIFIC PROMOTERS

(75) Inventors: Anne Elisabeth Osbourn, Norwich (GB); Kosmas Haralampidis, Athens (GR); Rachel Melton, Norwich (GB); Saleha Bakht, Norwich (GB); Xiaoquan Qi, Beijing (CN)

(73) Assignee: Plant Bioscience Limited, Norwich, Norfolk (GB)

( * ) Notice: Subject to any disclaimer, the term of this patent is extended or adjusted under 35 U.S.C. 154(b) by 191 days.

(21) Appl. No.: 11/940,638

(22) Filed: Nov. 15, 2007

(65) Prior Publication Data
US 2008/0244791 A1 Oct. 2, 2008

Related U.S. Application Data

(60) Provisional application No. 60/865,936, filed on Nov. 15, 2006.

(51) Int. Cl.
*C12N 15/82* (2006.01)
*C12N 15/63* (2006.01)

(52) U.S. Cl. ..... 800/287; 536/24.1; 800/278; 435/320.1

(58) Field of Classification Search .................. None
See application file for complete search history.

(56) References Cited

U.S. PATENT DOCUMENTS

2003/0177518 A1* 9/2003 Osbourn et al. ............. 800/278
2004/0067506 A1* 4/2004 Scheres et al. ................ 435/6

FOREIGN PATENT DOCUMENTS

WO 01/46391 6/2001
WO 2006/044508 4/2006

OTHER PUBLICATIONS

Atanassova, R. et al., "Functional analysis of the promoter region of a maize (Zea mays L) H3 histone gene in transgenic *Arabidopsis thaliana*," Plant Mol. Biol. (1998) 37:275-285.

Haralampidis, K. et al., "A new class of oxidosqualene cyclases directs synthesis of antimicrobial phytoprotectants in monocots," Proc. Natl. Acad. Sci. USA (2001) 98(23):13431-13436.

Qi, X. et al., "A gene cluster for secondary metabolism in oat: implications for the evolution of metabolic diversity in plants," Proc. Natl. Acad. Sci. USA (2004) 101(21):8233-8238.

Qi, X. et al., "A different function for a member of an ancient and highly conserved cytochrome P450 family: from essential sterols to plant defense," Proc. Natl. Acad. Sci. USA (2006) 103(49):18848-18853.

* cited by examiner

*Primary Examiner* — Li Zheng

(74) *Attorney, Agent, or Firm* — Michael Best & Friedrich LLP

(57) ABSTRACT

Promoters and genes involved in avenacin production in oats are cloned and characterized. Promoters for oxidosqualene cyclase and a cytochrome P450 are shown to be useful in root-specific expression of genes operatively linked to these promoters when introduced into plants. Sequences operably linked to the promoters are expressed in root epidermal cells.

28 Claims, 22 Drawing Sheets

AsCYP51H10 PROMOTER (2998nt, SEQ ID NO: 181)

GARE-motif (GA responsiveness)
GTTTATTGATCACACAATAGTGAGAGACACGGCCCTTGCAAAACAGACTGCCAAACCACTGCATAGTCGCCAAAACAACGACAATAAAG
TGACG-motif (MeJ)
CTCGAAAACTATCTCCAAGGAGCAGAGCATGACGGGCCACACTAAGACTTGGAATGGAGGAATGCTACTTTTAATCCATGCCGCCTTAA
TTACGGAAATTTTTCACGAATAACACGCTAAAGTGACAAAGATATATACCTAATTCCACATGACAGACGAACCATGCATCCATTGCAAC CCAATAACTTATAGATCGTGTTAAGGTGAGGGGAATGATTTTGTGTAAGAGTAAACACTTTGTTATAAGTTAACATAAAAAACCAAATATTTACAAA
CTCTAATAACAATACAATTGAATAACGAGAGTGTATTTACTTGGATCAAGTGTCTTGTCCATATTGTCACATAGTCACTACAAACATTATTCTTACA
AAAGTATCCACATCAAAAAAATAAATTATATTATGTATAAAAAGCAACATAAGACCTAAAATAGAGAGATATT CTAGAAATTCTTACAAAAGCCAAACATCCAGCTGCTAATATGGTAGACCATATTGGTATTTAAACATATCACAACTAGGGGTTTTGTTT
W box (fungal elicitor)
CTCGCTGGAAGGAAATACTTGTGGGCAATGGTATTTCCGGTTTTCGAAAATACTAGAGCTGCCGGTCAAACTACCTCCCGAATTTTTTCAAACAAAC
CCATCCAAAGTTTATCAAAATTCTTTAAATTTTAGAAAAATATTAAAATACCTATGAATTTGGTATGGTAGTATTTGTTCT
W box (fungal elicitor)
TAGTGGTAACCGGAAACACCCGTTTCTGACTACATACCCGAACATCGGTCAAGAATAAAAACCTGATCATAACCATTGAATCTCCGTAAGTTTGCTA
ACGTATCATGCTGTTCTCATGTTACATAAGAAAAATGATAAAAATCCCCTCGATTTAGTAACACTATGCATTAGGTTTGTAGAAGAGTAAATGTTTG
AGAAAATGATAGTAGATTATTAATATTTGTCCTGACCATGCGCATGAGACACTAGCTAAGTGTCCCATAGTAA
W box (fungal elicitor)
GTATTGACACATCTAGAGATATGTCCATGTCTTAAATATCGTGTATTTGTTATATTAAGGATATAAATGTGAGAATATGTTGGTATAAC ATTGGAAAAAATGTTAACATACTAAACATGACTACCTCACATTTTTTACGGACATTGATATTCTAGAACTATCAATACCGCTATACTACCAGTAGGA
TATCATCTTCAATATCGATGATGTAGATATGCAAACTTGCACTTTCAAAAGAATGTTTAATATAATTTTCTAAGTGAACTATCTACCGAGACATTAT
ATCTTTAATAATATAAAAAATTCTTTATTGATTTTCCTGAATTTGAAACCCAAAATATGTCGGTCTACCTCTT
P-box (GA resp.)
CGAAAAATGACATTTAGCTCATGGTATGTCTTTTTCCATGATATAATAAAGTAATTTGTATCTTATATTTAAGTATACAAGTCATTCAAAAGGTAGT
TTTAGTCATGTGATATTTTTGTGTGGTGTCTCTAGAATAATTATTAATAAATTCAAAATTTTAGTATGTATATAACCATAAATTTATTTCTCAAGC
AAATAAAATGAGATTAAGACATTGCCCTCGCAATTGCGAGGTCTACCTGGCTAGTGAGAGAAAAAAGGAGAACATGCATTGAACCAGAGAGAGAGTA
ATAAATGAGATAACCCTTATAATCTCAAACAATATAAAAAAGCTCTTAGGACTAATAATCCTGAACAGAGGTAGTAACATGCAACTGTATGCATTCC
GAACTACGCATTTTGATGACATGACATGTCATTAAATAATGAAAACAGTCTTGTGGTAACTAGCTATGTTACCATAACACAAGACATGTCTAAGTAA
GATGAGTCTATGATATAATAAATGAGATATTCCATAAAACTAGATATAAGTTACTACCCACTCTGAAGATGATAACAAAGAATAGTAATGCACGCAT
GACAATACACTATTTACTAGTCTTCTCTAAATTTATCCGAT
ABRE / TGACG-motif (MeJ)
CAAAATGGCCTGCTCGGGTTGCAATGCATTCTTGACGTGTTGAAGTTTCTGATATCGATGTAAGGTGGTCATACAAGACGAGAATACCAA
ABRE / TGACG-motif (MeJ)
TGGAGTACTAGATCTCGATGGACTAAGCATATGCAAATTTTATCTGAACAAGAAGCAGGCTTACTCAGGTTGCAATGTATTCTTGACGTG
ABRE / TGACG-motif (MeJ)
CTGTTGCCTTGCTCCAGACGACCCGCATGCAAAAGCGAGCTTGTCCCCTAGAGTTGTGAATACTAGTTTCATTAGAAACATTGACGTCT
W box (fungal elicitor)

FIG. 9

```
GCGAAAGCCATTAATGCCTCTGTGAACACAATCGGGCAGTATTGACTAGAATCTCCAAGATCAGGCCATGAAATTAGTTGTTTACTTGA
                    W box (fungal elicitor)                                          W box
TAATATTGTCCAAGAGTTAGGGTTTAGGTCAAGTAGAGGCCGTGGCTTTTTTCCATTTCTCCATAATAAAAGGGCTTAGGTCAAGTAGT
                                              W box (fungal elicitor)
AGCTGCCTATATAAATGAGGCATTGCGGGGTTCCTTACTCACTTGTGTGCATTGACTGCTACCAGCTGTGTGCTGGACACTCGTTCACAGTGAACCA
GTCAGGAGGATTTCAAATTCGTATTCAGGTATGCTTGATTTTAGTTTTTAAGTCATATGAGTTCATTTTTAGATCATTTTTTCATACGAGAGAAATA
AGACTAGGGCTAGGTTTCTTCTTCATATGGGCCGGGTCCAACATTTCCATAACAATCACGCATCACAGCTATT ACTTGTTCTTCTGAATTTTCTATAGCCTTTAAAAACCGACAATCAGAGTTCAATTACCAATCTAGTCTTGGTCATATTTTGTTTCTTAATGAAGTGT
TTTTGCTTCACTTTGTCCTTGTGGAGTCGAATGTGGCTTCCTGTTTAGACTGTTAGCTAGGTTCACCCTTTCAGATTTCTT
                                              W box (fungal elicitor)
CATACTAATTATCTTCATATTCTGCCAGTGTGAATCCTCTAGTCAATAACGACATGGCACC
```

FIG. 9 Cont'd

Beta-Amyrin Synthase (*Sad1*) promoter (SEQ ID NO: 182)

```
+ AAAATATGTC CCTATCTATA TTTGAGTTTA TATAGATATA TCTTATTTTT CTGCAAATTT  TGATATATT  69
- TTTTATACAG GGATAGATAT AAACTCAAAT ATATCTATAT AGAATAAAAA GACGTTTAAA  ACTATATAA

+ ATATGTATTT TTCTGAATTT AAATAATTTA GTTATGATTT TTCTAAGATT A ATGTGGCA AAAAAAAGAA  138
- TATACATAAA AAGACTTAAA TTTATTAAAT CAATACTAAA AAGATTCTAA T TACACCGT TTTTTTTCTT
                                                         W_box(fungal elicitor) CAACGG
+ AAATAGCTAA GCCGTCGGCG TAGGTCTGAA ACCTACGCGT AG ACTTGACGGCCGTTGCTC TACCGTTAGC  207
- TTTATCGATT CGGCAGCCGC ATCCAGACTT TGGATGCGCA TC TGAACTG CGGCAACGAG ATGGCAATCG
                                                TGACG-motif(MeJ) MYB_binding site (plant defense)
+ CCAATGGGCT ACGCCGACGG TCATGTTTAC GCC GACGGC GGCCGTCGGC CTATTTATTC TACGCCGACG  276
- GGTTACCCGA TGCGGCTGCC AGTACAAATG CGG CTGCCG CCGGCAGCCG GATAAATAAG ATGCGGCTGC + GCAAAATTGG GCCGACGCCC CGTC AAGCT ACGCCGACGG TCCCGACATT TTGCCGTCGG CGTATAAAAA  345
- CGTTTTAACC CGGCTGCGGG GCAG TTCGA TGCGGCTGCC AGGGCTGTAA AACGGCAGCG GCATATTTTT
                                                    W_box(fungal elicitor)
+ GACCGTCGGC CTATT TAGT TATTCCCGTA GTGTGTCGGT GTTGACACTA TTATGGTAAC TATCCTAACC  414
- CTGGCAGCCG GATAA ATCA ATAAGGGCAT CACACAGCCA CAACTGTGAT AATACCATTG ATAGGATTGG
    MYB_binding site (plant defense)
+ GGTAGG TTA CAATTATCAG GGCTTTGTCA TGCACATTTA TAAATGTGAA TCAGGTTGAA CTTTATT TG  482
- CCATCC AAT GTTAATAGTC CCGAAACAGT ACGTGTAAAT ATTTACACTT AGTCCAACTT GAAATAA AC + GTGTTCCCAA TCAGACGTTA GTAAACACAA TATCAGATTA ACCTGGGAAA TCTTCATG T AACTTAGACT  551
- CACAAGGGTT AGTCTGCAAT CATTTGTGTT ATAGTCTAAT TGGACCCTTT AGAAGTAC A TTGAATCTGA
                                                                    dOCT(meristem
specific)
+ AATAAAATGC ATCTGTTACC GTGTACAAAT ACTATCACTA ACCAGATCC  CTGCAAGACA AGATCCACGG  620
- TTATTTTACG TAGACAATGG CACATGTTTA TGATAGTGAT TGGTCTAGG  GACGTTCTGT TCTAGGTGCC
                                                 W_box(fungal elicitor)
+ ATCATGGTGC AGCGATTTAC GAGATAATCT ATTGACTAAT  TATACTTGT TCTAGTACTA TCTACTGACC  689
- TAGTACCACG TCGCTAAATG CTCTATTAGA TAACTGATTA  ATATGAACA AGATCATGAT AGATGACTGG + CTTCTCTGGA AGACAACCAT CGTGTATTCT G CACCGATG GAAGTGAATA GATCTTTCTT GTATTATCCC  758
- GAAGAGACCT TCTGTTGGTA GCACATAAGA C GTGGCTAC CTTCACTTAT CTAGAAAGAA CATAATAGGG + TCATGAAGGC ACTCAGAGCA AA CTTGAGC GAACCTTCCG CATTCATTTC TTCACATGCG GTGTCTGATC  827
- AGTACTTCCG TGAGTCTCGT TT GAACTCG CTTGGAAGGC GTAAGTAAAG AAGTGTACGC CACAGACTAG + AGTCAAACAA CCT CCAGAG ATTTAGTAAA AACAATGTCT CGGGATTCCG CGATTAATTT AGTCGTCTTA  896
- TCAGTTTGTT GGA GGTCTC TAAATCATTT TTGTTACAGA GCCCTAAGGC GCTAATTAAA TCAGCAGAAT
```

FIG. 10

```
+ TGGC CTCGA GTACTTGTTA TAATAAGATG ATTTGATACT TGCAGTATCT TTACAAACTG CTAGC TAAA   964
- ACCG GAGCT CATGAACAAT ATTATTCTAC TAAACTATGA ACGTCATAGA AATGTTTGAC GATCG ATTT
                                                                    CAT-box(meristem
specific)
+ TTGGACAGTA GCTAGTTTTG TCAGTCTAGT ACGTACTACA TAGTATTTTT TTCTGT ATC TAGTGGCACT  1033
- AACCTGTCAT CGATCAAAAC AGTCAGATCA TGCATGATGT ATCATAAAAA AAGACA TAG ATCACCGTGA + ACTGAAATCT CACTTTCCAC GATTTCAAAT AAAAATTACC TGATCTG AC ATGATCACTG GCTACGCCGA  1102
- TGACTTTAGA GTGAAAGGTG CTAAAGTTTA TTTTTAATGG ACTAGAC TG TACTAGTGAC CGATGCGGCT + GATTCTACAA ATATTTCTAT AAGTAGTTTG TGGATTCC A ATATATATAC GGATTCCGTA AAGCTCTCTT  1171
- CTAAGATGTT TATAAAGATA TTCATCAAAC ACCTAAGG T TATATATATG CCTAAGGCAT TTCGAGAGAA + ACCGATGGTA TGACTTTAGT AGTAACAAA  ATCATAGGCT TCGAGTGAAG ATTGGCTACC AACTGTAATG  1240
- TGGCTACCAT ACTGAAATCA TCATTGTTT  TAGTATCCGA AGCTCACTTC TAACCGATGG TTGACATTAC + TAAGATTGTT GTCCAAGATA  AGATACTCA AGTTACAGAT GCACTACTCT AATACTAAGA GTTATTGATC  1309
  ATTCTAACAA CAGGTTCTAT  TCTATGAGT TCAATGTCTA CGTGATGAGA TTATGATTCT CAATAACTAG + TATATTACGG C TCCCGTAC CGTAGACATA TTGATTCTAC GTTCACCTTC TTAAAAGGAC ATTCTTCTAC  1378
- ATATAATGCC G AGGGCATG GCATCTGTAT AACTAAGATG CAAGTGGAAG AATTTTCCTC TAAGAACATG
                                                                       TCA-element(SA
responsiveness)
+ AA TCAAAAC AAATGGGTCT AGCTACCTTG GTCAATATGT ATTTCTATCG GTATTTAGTT ATA AAGGAC  1446
- TT AGTTTTG TTTACCCAGA TCGATGGAAC CAGTTATACA TAAAGATAGC CATAAATCAA TAT TTCCTC
   A
+ AGGAATACAG AATAATTTTT TTAACTCCAT AGTACCTCTA TTGCTTTCAG TATA AAGAG TTTGATGCAC  1515
- TCCTTATGTC TTATTAAAAA AATTGAGGTA TCATGGAGAT AACGAAAGTC ATAT TTCTC AAACTACGTG + GGTTCTCTGT ACTAATAAAT GTTCTATTGT TGATTGATTC TTAAC CGCA TCCTATGCAA TTTTAACCTC  1584
- CCAAGAGACA TGATTATTTA CAAGATAACA ACTAACTAAG AATTG GCGT AGGATACGTT AAAATTGGAG + AAAAAAGTTT CACGGTACAC CGACTTGCCT TACTAG CCC TACTGTTTTC TTGAGAAGGA TGTTCAAACT  1653
- TTTTTTCAAA GTGCCATGTG GCTGAACGGA ATGATC GGG ATGACAAAAG AACTCTTCCT ACAAGTTTGA + TTGGGCTTTT GCATCTAAAA TAAGACA CA CATCATTTTT GGTTTATTAT TCAACAATGT GTGGGAAAAG  1722
- AACCCGAAAA CGTAGATTTT ATTCTGT GT GTAGTAAAAA CCAAATAATA AGTTGTTACA CACCCTTTTC + CATACAACAA TCAACTCG A TATACCACCT TCGCGGAGGG CCTCCTCTTT AAATGTCTGG GAGTACTACA  1791
- GTATGTTGTT AGTTGAGC T ATATGGTGGA AGCGCCTCCC GGAGGAGAAA TTTACAGACC CTCATGATGT
```

FIG 10 Cont'd

```
+ CATATGTAA  AGATGATGCC CACTTACAAA GAACGAGGAC ACCACTTAAA CCGGGTGTAC AAAGTACTAC  1860
- GTATACATT  TCTACTACGG GTGAATGTTT CTTGCTCCTG TGGTGAATTT GGCCCACATG TTTCATGATG

+  ACATATGTA AAGATGAGGC CATAGAACAA GCAAGAGCAC CAAGATATTT AGATCCACTA A AATGCAAC  1928
-  TGTATACAT TTCTACTCCG GTATCTTGTT CGTTCTCGTG GTTCTATAAA TCTAGGTGAT T TTACGTTG
                                TGACG-motif(MeJ)
+ CACCTCGATG TCCATAAAAA ATGATGG TGA CG TACAACAC TCAACAAATA TC GATAAAA ATGATAGTGT  1997
- GTGGAGCTAC AGGTAT TTTT TACTACC ACT GCATGTTGTG AGTTGTTTAT AG CTATTTT TACTATCACA
                   TCA-element(SA responsiveness)
+ CCTAGTTGCA CATCTTCTAA CATGTTGGTG TCTATTATGC ACA AGTGGG CATGGAAGCA AGTAAATATT  2066
- GGATCAACGT GTAGAAGATT GTACAACCAC AGATAATACG TGT TCACCC GTACCTTCGT TCATTTATAA + GTGTACTATA GCTACTGGTG ACTCGAGTGT ATCT CCAAG ACTCGATAGC AAACCCGAAG CCTCTTCAGC  2135
- CACATGATAT CGATGACCAC TGAGCTCACA TAGA GGTTC TGAGCTATCG TTTGGGCTTC GGAGAAGTCG
                                                               box S G-box
ABRE(pathogen/MeJ/ABA)
+ TTGTCCACAT ATCATTGTGG AATGT TCAC TACGACTCGC CACGCCAAGC ATAACCTGGA TA AGCCACG   2204
- AACAGGTGTA TAGTAACACC TTACA AGTG ATGCTGAGCG GTGCGGTTCG TATTGGACCT AT TCGGTGC A
   TATC-box                                                      box S(pathogen
responsiveness)
+  GATATGAG ATTTCC CGC AGCTTCCCTC TGAGTGAGGA GGCAGAACTA TACGCCTCAA CACGACG AGC   2273
-  CCCTAT ACTC TAAAGG GCG TCGAAGGGAG ACTCACTCCT CCGTCTTGAT ATGCGGAGTT GTGCTGCTCG
   TATC-box(GA responsiveness)
+ CACC CCC TA AGGCTAGTCA TAGTGGGAGT AACTTGGGTA GTAACATATT CCTACATATA TTGCGAAC T  2341
- GTGGGGG AT TCCGATCAGT ATCACCCTCA TTGAACCCAT CATTGTATAA GGATGTATAT AACGCTTG A + AACCATTTAC ATCACATGAC ATCCAATTAA ATCATCACAC AGACTCTTAT GATAACTAC  CTATCTTACC  2410
- TTCGTAAATG TACTGTACTG TAGGTTAATT TAGTAGTGTG TCTCAGAATA CTATTGATC  GATACAATGG + ATAACATCAC ACATTTCTAA AAAAATAAAT CTATATTATA ATAAATAAGG  TTTTGCATG ATACCACATC  2479
- TATTGTAGTG TGTAAAGATT TTTTTATTTA GATATAATAT TATTTATTCC  AAAACGTAC TATGGTGTAG + TATGTTATTT TGCACTATGA AGATAGTAAC TTAGACTAGT A ACATATAC ATGTTACTAC TCTAAGTTAC  2548
- ATACAATAAA ACGTGATACT TCTATCATTG AATCTGATCA T TGTATATG TACAATGATG AGATTCAATG
                                P-box(GA responsiveness)
+ TCCCCACAAT GACCAGCCTA ACA CCTTTTG TA CTGTTTT GCACATTTGC AGTTACTTT TTCTTAGGTG  2617
- AGGGGTGTTA CTGGTCGGAT TGT GGAAAAC AT GACAAAA CGTGTAAACG TCAATGAAA AGAATCCAC
                                                 ABRE
+ AAGAGAAAAC ACAAGACATA ATT TTAATA TTTCAACTTC AT TACGG CT GGTGCAAATA ATTTTTACGG  2686
- TTCTCTTTTG TGTTCTGTAT TAA AATTAT AAAGTTGAAG TA ATGCC GA CCACGTTTAT TAAAAATGCC + TGCAATTTTC GACA TGATT TATTGTATAT TTACAGAAAT TTATGCTCCA AATTTGTTTG GTACCTTCAG  2755
```

FIG. 10 Cont'd

```
- ACGTTAAAAG CTGT ACTAA ATAACATATA AATGTCTTTA AATACCAGGT TTAAACAAAC CATGGAAGTC

+ TATTA GTTT CTGGACATTG TACATATTAT GTTGCCGTAT AAGCTGAGCT AGAAGGATCA TTAGTG TAA    2823
- ATAAT CAAA GACCTGTAAC ATGTATAATA CAACGGCATA TTCGACTCGA TCTTCCTAGT AATCAC ATT
                                                                    P-box(GA responsiveness)
+ TTCCATATAT ATCTAAATGT ACCTGTGGAA TCACATTTGA GGAAGTTCCA ATGATGC CC TTTTTG CCCT   2892
- AAGGTATATA TAGATTTACA TGGACACCTT AGTGTAAACT CCTTCAAGGT TACTACG GG AAAAACGGGA
                                                                    TATC-box(GA responsiveness)
+ GCACACGCAT ATATAAGAAC CCTTTGCCCG CAGCATAGAG CTAGTACT A GCTAG TATCC CA TTGCTTGT  2961
- CGTGTGCGTA TATATTCTTG GGAAACGGGC GTCGTATCTC GATCATGA T CGATCATAGG GTAACGAACA
              MYB binding site (plant defense)
+ TTTCCTCGCA TACACTGCCC GTTGTTGGTG CGCAC  2996
- AAAGGAGCGT ATGTGACGGG CAAC ACCAC GCGTG
```

FIG. 10 Cont'd

```
CLUSTAL W (1.83) multiple sequence alignment using 2998 bp of each sequence.

bAS        GAAAATATGTCCCTATCTATATTTGAGTTTATATAGATATATCTTATTTTTCTGCAA-AT 59
cypA       --------------GTTTATTGATCACACAATAGTGAGAGACACGGCCCTTGCAAAACAG 46
                * ***    * *    *   * *             * bAS        TTTGATATATTA-TATGTATTTTTCTGAATTTAAATAATTTAGTTATGAT----TTTTCT 114
cypA       ACTGCCAAACCACTGCATAGTCGCCAAAACAACGACAATAAAGCTCGAAAACTATCTCCA 106
             **  *  *  *  **   *  **    *  **    * *    *    * * * bAS        AAGATTAATGTGGCAAAAAAAGAAAAATAGCTAAGCCGTCGGCGTAG-GTCTGAAACCT 173
cypA       AGGAGCAGAGCATGACGGGCCACACTAAGACTTGGAATGGAGGAATGCTACTTTTAATCC 166
            * **   *         *      *      *      * **   *   * **  * bAS        ACGCGTAGACTTGACGCCGTTGCTCTACCGTTAGCCCAATGGGCTACGCCGACGGTCATG 233
cypA       ATGCC--GCCTTAATTACGGAAATTTTTCACGAAT--AACACGCTAAAGTGACAAAGATA 222
           * ***  * ***  *  **     *   *         **   *    ** bAS        TTTACGCCG------ACGGCGGCCGT-CGGCCTATTTATTCTACGCCGACGGCA---AAA 283
cypA       TATACCTAATTCCACATGACAGACGAACCATGCATCCATTGCAACCCAATAACTTATAGA 282
           * ***          * * * **  *     *  * ** *   *       * * bAS        TTGGGCCGACGCCCCGTCAA-GCTACGCCGACGGTCCCGACATTTTGCCGTCGGCGTATA 342
cypA       TCGTGTTAAGGTGAGGGGAATGATTTTGTGTAAGAGTAAACACTTTGTTATAAGTTAACA 342
           * * *  **   *    ** *    *      *    * **   *    *   * bAS        -AAAAGACCGTCGGCCTA-----TTTAGTTAT--TCCCGTAGTGTGTCGGTGTTGACACT 394
cypA       TAAAAAACCAAATATTTACAAACTCTAATAACAATACAATTGAATAACGAGAGTGTATTT 402
            ** *          **    * ** *     *   * *  *   **      * bAS        ATTATGGT-AACTATCCTAACCGGTAGGTTACA--ATTAT--CAGGGCTTTGTCATGCAC 449
cypA       ACTTGGATCAAGTGTCTTGTCCATATTGTCACATAGTCACTACAAACATTATTCTTACAA 462
           * *  * *            *    * bAS        ATTTATAAATGT----GAATCAGGTTGAACTTTATTTGGTGTTCCCAATCAGACGTTAGT 505
cypA       AAGTATCCACATCAAAAAAATAAATTATATTATGTATAAAAAGCAACATAAGACCTAAAA 522
             *  ***  *     **  *  **  * **  *   *         *   *  * bAS        AAACACAATATCAGATTAACCTGGGAAATCTTCATGTAACTTAG-ACTAATAAAATGCAT 564
cypA       TAGAGAGATATTCTAGAAATTCTTACAAAAGCCAAACATCCAGCTGCTAATATGGTAGAC 582
            *    ****   *                         ****    *  * bAS        C-TGTTACCGTGTACAAATACTATCACTAA----CCAGATCCCTGC---AAGACAAGATC 616
cypA       CATATTGGTATTTAAACATATCACAACTAGGGGTTTTGTTTCTCGCTGGAAGGAAATACT 642
           *  * **   * ** *    *   **        *      * bAS        CACGGATCATGGTGCAGC-GATTTACGAGA-TAATCTATTGACTAATTATACTTGTTCTA 674
cypA       TGTGGGCAATGGTATTTCCGGTTTTCGAAAATACTAGAGCTGCCGGTCAAACTACCTCCC 702
              *** *       * *  * ** *    * *    *     * bAS        GTACTATCT---ACTGACCCTTCTCTGGAAGACAACCATCGTGTA--TTCTGCACCGATG 729
cypA       GAATTTTTCAAACAAACCCATCCAAAGTTTATCAAAATTCTTTAAATTTTAGAAAAATA 762
           * * * *        **     *   *   ** * **    *   *   ** bAS        --GAAGTGAATA-GATCTT--TCTTGTATTATCC-CTCATGAAGGCACTCAGAGCAAACT 783
cypA       TTAAAATACCTATGAATTTGGTATGGTAGTATTTGTTCTTAGTGGTAACCGGAAACACCC 822
                    **    *  * * * *   *  ***  *  **    * * bAS        TGAGCGAAC--CTTCCGCATTCATTTCTTCACATGCGGTGTCTGATCA--GTCAAACAAC 839
cypA       GTTTCTGACTACATACCCGAACATCGGTCAAGAATAAAAACCTGATCATAACCATTGAAT 882
             *      ** * *  ***  *     * *      ****** * bAS        CTCCAGAGATTTAGTAAAA----ACAATGTCTCGGGATTCCGCGATTAATTTAGTCG--- 892
cypA       CTCCGTAAGTTTGCTAACGTATCATGCTGTTCTCATGTTACATAAGAAAAATGATAAAAA 942
           ****  *  ***  ***      *   *** *      *   * *   * *
```

FIG. 11

```
bAS     TCTTATGGCCTCGAGTACTTGTTATAATA-------AGATGATTTGATACTTGC-AGTAT  944
cypA    TCCCCTCGATTTAGTAACACTATGCATTAGGTTTGTAGAAGAGTAAATGTTTGAGAAAAT 1002
        **    * * *     **     * *       * ** *  *  *  ** bAS     CTTTACAAACTGCTAGCTAAATTGGACAGTAGCTAGTTTTGTCAGTCTAG-TACGTACTA 1003
cypA    GATAGTAGATTATTAAT--ATTTGTCCTGACCATGCGCATGAGACACTAGCTAAGTGTCC 1060
           *   *  *     * *    *      **  *  **  ** bAS     CATAGTATTTTTTCTGTATCTAGTGG------CACTACTGAAATCTCACTT-TCCACGA  1056
cypA    CATAGTAAGTATTGACACATCTAGAGATATGTCCATGTCTTAAATATCGTGTATTTGTTA 1120
        *******   *      **** *               **    *          * bAS     TTTCAA--ATAAAAATTACCTGATCTGACATGAT--CACTGGCTA---CGCCGAGATTCT 1109
cypA    TATTAAGGATATAAATGTGAGAATATGTTGGTATAACATTGGAAAAAATGTTAACATACT 1180
        * *   * **         *  *   *   * bAS     ACAAAT-ATTTCTATAAGTAGTTTCTGGATTCCAATATATATACCGATTCCGTAAAGCTC 1168
cypA    AAACATGACTACCTCACATTTTTTACGGACATTGATATTCTAGAACTATCAATACCGCTA 1240
        *   *    *  **    * *   *  *     **             * bAS     TCTTACCGATGGTATGACTTTAGTAGTAACAAAATCATAGGCTTCGAGTGAAGATTGGCT 1228
cypA    TACTACCAGTAGGATATCATCTTCAATATCGATGATGTAGATAT---GCAAACTTGCACT 1297
        *  ****  *  ** * *  *    * ** * *      ***   *   *  **  *  ** bAS     ACCAACTGTA-ATGTAAGATTGTTGTCCAAGATAAGATACTCAAGTTACAGATGCACTAC 1287
cypA    TTCAAAAGAATGTTTAATATAATTTTCTAAGTGAA------CTATCTACCGAGACATTAT 1351
         ***  *  *  *    * *     *         * * * bAS     TCTAATACTAACAGTTATTCATCTATATTACCGCTCCCGTACCGTAGACATATTGATTCT 1347
cypA    ATCTTTAATAATATAAAAAATTCTTTATTGATTTTCCTGAATTTGAAACCCAAAATATGT 1411
               * *   *    *    * * *    *     *   *       * * bAS     ACGTTCACCTTCTTAAAAGGAGATTCTTGTACAATCAAAACAAATGGGTCTAGCTACCTT 1407
cypA    CGGTCTACCTCTTCGAAAAATGACATTTA---GCTCATGGTATGTCTTTTTCCATGATAT 1468
          * **  * *                *  * *  *  *  *       * bAS     GGTCAATATGTATTTCTATCG-GTATTTAGTTATAAAGGAGAGGAATACAGAATAATTTT 1466
cypA    AATAAA-GTA-ATTTGTATCTTATATTTAAGTATACA----AGTCATTCAAAA-GGTAGT 1521
           * **   *  **   ** ** ** *           *  * bAS     TTTAACTCCATAGTACCTCTATTGCTTTCAGTATAAAGAGTTTGATGCACGGTTCTCTGT 1526
cypA    TTTAGTCATGTGATATTTTTGTGTGGTGTCTCTAGAATAATTATTAATAAATTCAAAAT  1591
        ****      *  **    *  * *    * *** *        **  *      ***        * bAS     ACTAATAAATGTTCTATTGTTGATTGATT-CTTAACCGCATCCTATGCAATTTTAACCTC 1585
cypA    TTTAGTATGTATATAACCATAAATTTATTTCTCAAGCAAATAAAATGAGATTAAGACATT 1641
              *    *      *  * * * *        * *   * bAS     AAA---AAAGTTTCACGGTACACC-GACTTGCCTTACTAGC--------CCTACTGTTTT 1633
cypA    GCCCTCGCAATTGCGAGGTCTACCTGGCTAGTGAGAGAAAAAGGAGAACATGCATTGAA  1701
              * ***  * * * * ** *     *         * *   * * bAS     CTTGAGAAGGATGTTCAAACTT--TGGGCTTTTGCATCTAAAATAAGACACACATCATTT 1691
cypA    CCAGAGAGAGAGTAATAAATGAGATAACCCTTATAATCTCAAACAATATAAAAAAGCTCT 1761
         * **      ***     *      * ***  *  *      *    *  * bAS     TTGGTTTATTATTCAACAATGTGTGGGAAAAGCATACAACAATCAACTCGATATACCACC 1751
cypA    TAGGACTAATAATCCTGAACA-GAGGTAGTAACATGCAACTGTATGCATTGCGAACTACG 1820
        *          **  *  *  * *    *   * bAS     TTCGCGGAGGGCCTCCTCTTTAAATGTCTGGGAGTACTACACATATGTAAAGATGATGCC 1811
cypA    CATTTTGATGACATGACATGTCATTAAATAATGAAAACAGTCTTGTGGTAACTAGCTATG 1880
              *  *  *    *  * *  *     *    *  *  * * ***  **      *  *
```

FIG. 11 Cont'd.

```
bAS   CACTTACAAAGAACGAGGACACCCACTTAAACCGGGTGTACAAAGTACTACACATATGTAA 1871
cypA  TTACCATAACACAAGACATGTCTAAGTAAGATGAGTCTATGATATAATAAATG------- 1933
       * **    * **       * *  ***    *     *     * bAS   AGATGAGGCCATAGAACAAG-CAAGAGCACCAAGATATTTAGATCCACTAAAATGCAACC 1930
cypA  AGAT-ATTCCATAAAACTAGATATAAGTTACTACCCACTCTGAA--GATGATAACAAAGA 1990
      ****  *  *** *  **   *    * *    *   **     * *   ** bAS   ACCTCGATGTCCATAAAAAATGATGGTGACGTACAACACTCAACAAATAT---CGATAAA 1987
cypA  ATAGTAATGCACGCATGACAATACACTATTTACTAGTCTTCTGTAAATTTATCCGATCAA 2050
       *   ***  *    *   *   *   *    * *     **  *   ** bAS   AATGATAGTGTCCTAGTTGCA-CATCTTCTAACATGTTG--GTGTCTATTATGCAC---A 2041
cypA  AATGGCC-TGCTCGGGTTGCAATGCATTCTCACGTGTTGAAGTTTCTGATATCGATGTAA 2109
      **       * ****     *   *  * *     * bAS   AGTGGGCATGGAAGCAAGTAAATATTG-TGTACTA-TAGCTACTGGTGACTCGAGTGTAT 2099
cypA  GGTGGTCATACAAG-ACCGAATACCAATGGAGTACTAGATCTCGATGGACTAAGCATAT 2168
       ** *  *** *    *   * *   *      *     *     * bAS   CTCCAAGACTCGATAGCAAACCCGAAGCCTCTTCAGCTGTGCACATATCATTGTGGAAT 2159
cypA  GCAAATTTTATCTGAACAAGAAGCAGGCTTACTCAGGTTG-CAATGTATTCTCACGTACT 2227
         *       * ***     * **    *    *  *  ***  *  * ** bAS   GTT-CACTACGACTCGCCACGC-CAAGCATAACCTGGATAAGCCACGTGGGATATGAGAT 2217
cypA  GTTGCCTTGCTCCAGACGACCCCCATGCAAAAGCGGCTGTGCGCCTAGAGTTGTGAA-- 2285
      ***  * *      *    *  *     *   *   **  *  * * *** bAS   TTCCCGCAGCTTCCCTCTGAGTGAGGAGGCAGAACTATACGCCTCAACACGACGAGCCAC 2277
cypA  ----TACTAGTTTCATTAGAAACATCACGTACTGCGAAAGCCATTAATGCCTCTGTGAAC 2341
            *      **   *    *  * *     *    *  **   *    ** bAS   CCCCTAAGGCTAGTCATAGTGGGAGTAACTTGGGTAGTAACATATTCCTACATATATTGC 2337
cypA  ACAATCGGGC-AGTATTGACTAGAATCTCCAAGATCAGGCCATG-----AAATTAGTTGT 2395
       *   * * *  *     **   *    * *    ***      *    * bAS   GAACTAAGCATTTAGATGACATGACATGCAATTAAATGATGAGAGAGAGTCTTATGATAA 2397
cypA  TTACTTGATAAATATTGTC-CAAGAGTTAGGGTTTA--GGTCAAGTAGAGGCC-GTGGCTT 2451
         ***           *  *  **    *   **  * *  * *      * ** bAS   CTAGCTATGTTACCATAACATCACACATTTC-TAAAAAATAAATCTATATTATAATAAA 2456
cypA  TTTTCCATTTCTCCATAATAAAAGGGCTTAGGTCAAGTAGTAGCTGCCTAT----ATAAA 2507
        *   ** * ****** *   *   * **   *   *  * ** *     *** bAS   TAAGGTTTTGCATGATACCA----CATCTATGT-TATTTTGCACTATGAAGATAGTAACT 2511
cypA  TGAGGCATTGCGGGGTTCCTTACTCACTTGTGTGCATTGACTGCTACCAGCTGTGTGCTG 2567
      * * ** *          * *         *****    *  ** bAS   TAGACTAGT--AACATATACATGTTACTA---CTCTAAGTTACTCCCCACA-ATGACCAG 2565
cypA  GACACTCGTTCACAGTGAACCAGTCAGGAGGATTTCAAATTCGTATTCAGGTATGCTTGA 2627
        * *   **    *           **    *   * *    * bAS   CCTAACACCTTTTGTACTGTTTTGCACATTTGCAGTTTACTTTTTCTTAGGTGAAGAGAA 2625
cypA  TTTTAGTTTTTAAGTCATATGA-GTTCATTTTTAGATCATTTTTTCATACG-AGAGAAAT 2685
        *   *     * *    *  ***     **  * *  ****  * bAS   AACACAAGACATAATTTTAATATTTCAACTTCATTACGTGCTGGTGCAAATAATTTTTAC 2685
cypA  AAGACTAGGGCTAGGTTTGTT-------CTTCATATGGGCCGGGTGCAAC--ATTTCGAT 2736
              ***  *      ******    * *  ****    **  * bAS   GGTGCAATTTTCGACATGATTTATTGTATATTTACAGAAATTTATGCTCCAAATTTGTTT 2745
cypA  AA--CAATCACGCATCAGAGCTATTACTTGTTCTTCTGAATTT----TCTATAGCCTTTA 2790
         ****   *   ** **  **** *  *  *  *****     **  *       **
```

FIG. 11 Cont'd

```
bAS    GGTACCTTCAGTATTAGTTTCTGGACATTGTACATATTATGTTGCCGTATAAGCTGAG-C  2804
cypA   AAAACCGACAATCAGAGTTCA-----ATTACCAATCTAGTCTTGGT-CATATTTTGTTTC  2844
       *   *  **         *   ** *  * *    *   **    * bAS    TAGAAGGATCATTAGTGTAATTCCATATATATCTAAATGTACCTGTGGAATCACATTTGA  2864
cypA   TTAATGAAGTGTTTTTGCTTCACTTTGTCCTTGTGGAGTCGAATGTGGCTTCCTGTTTAG  2904
       *   *  *          *   * *  * *   *     ***     *** bAS    GGAAGTTCCAATGATGCCCTTTTTGCCCTGCACACGCATATATAAGAACCCTTTGCCCGC  2924
cypA   ACTGTTAGCTAGGTTCACCCTTTCAGATTTC-TTCATACTAATTATCTTCATATTCTGCC  2963
         * * * *    *    ** *  * *   *   ** *   * *  * bAS    AGCATAGAGCTAGTACTAGCTAGTATCCCATTGCTTGTTTTCCTCGCATACACTGCCCGT  2984
cypA   AGTGTGAATCCTCTAGTCAATAACGACATGGCACC-------------------------  2998
       **  *  *      **    *        * bAS    TGTTGGTGCGCACC  2998
cypA   --------------
```

FIG. 11 Cont'd

CLUSTAL W (1.83) multiple sequence alignment using 951 bp of each sequence

```
bas      ------------------------------GCCGAGATTCTACAAATATTTCTATAAGTAG  31
cypa     CTTAAATATCGTGTATTTGTTATATTAAGGATATAAATGTGAGAATATGTTGGTATAACA  60
                                       *    *  *   *****  *    ** bas      TTTGTGGA--TTCCAATATA-TATACG-GATTCCGTAAAGCTCTCTTACCGATGGTATGA  87
cypa     TTGGAAAAAATGTTAACATACTAAACATGACTACCTCACATTTT-TTACGGACATTGATA 119
         ** *     *  *      *     *  *  *  **      *   * bas      CTTTAGTAGTAACAAAATCA-TAGGCTTCGAGTGAAGATTGGCTACCAACTGTAATGTAA 146
cypa     TTCTAGAACTATCAATACCGCTATACTACCAGTAGGATATCATCTTCAATATCGATG--A 177
          * ***  *   * * *     * *  *     *    *** * bas      GATTGTTGTCCAAGATAAGATACTCAAGTTACAGATGCACTACTCTAATACTAAGAGTTA 206
cypa     TGTAGATATGCAAACTTGCACTTTCAA---AAGAATGT-TTAATATAATTTTCTAAGTGA 233
          * * * ***   *  *  ****    *  *   * ****  *    *** * bas      TTGATCTAT------ATTACGGCTCCCGTACCGTAGAGATATTGATTCTACGTTCACCTT 260
cypa     ACTATCTACCGAGACATTATATCTTTAATAATATAAAAA-----ATTCTTTATTGATTTT 288
           ***                 *      ***     *  ** bas      CTTAAAAGGAGATTCTTGTACAATCAAAACAAATGGGTCTAGCTACCTTGGTCAAT-ATG 319
cypa     CCTGAA--------TTTGAAACCCAAAATATGTCGGTCTACCT-CTTCGAAAAATGACA 338
         * *          *  *  ***** *  * ****   * * *   *** * bas      TATTTCTATCGGTATTTAGTT-------ATAAAGGAGAGGAATACAGAATAATTTTTTTA 372
cypa     TTTAGCTCATGGTATGTCTTTTTCCATGATATAATAAAGTAAT-TTGTATCTTATATTTA 397
         * *     *** *         * *  *  ***  *  *  *  *  **** bas      ACTCCATAGTACCTCTA-----TTGCTTTCAGTATAAAGAGTTTGATGCACGGT-TCTCT 426
cypa     AGTATACAAGTCATTCAAAAGGTAGTTTTAGTCATGTGATATTTTTTGTGGTGTCTCT 457
         * *  *    *  * *      * * *            * *** bas      GTACTAATAAATGTTCTATTGTTGATTGATTCTTAACCGCATCCTATGCAATTTTAACCT 486
cypa     AGAATAATTATTAATAAATTCAAAATT--TTAGTATGTATATAACCATAAATTTATTTCT 515
           * ****  *   *  *   *               * bas      CAAAAAAGTTTCACGGTACACCGAC-TTGCCTTACTAGCCCTACTGTTTTCTTGAGAAGG 545
cypa     CAAGCAAATAAAATGAGATTAAGACATTGCCCTCGCAATTGCGAGGTCTACCTGGCTAGT 575
         *    *    *   *  * *  *** *    *     ** * * **  * bas      ATGTTCAAACTTTGGGCTTTTGCATCTAAAATAAGACACACATCATTTTTGGTTTATTAT 605
cypa     GAGAGAAAAAG-GAGAACATGCATTGAACCAGAGAGAGA-GTAATAAATGAGATAACCC 633
          *   ***    *  *   ***    *** *   *  * bas      TCAACAATGTGTGGGAAAAGCATACAACAATCAACTCGATATACCACCTTCGCGGAGGGC 665
cypa     TTA-TAATCTCAAACAATATAAAAAAGCTCTTAGGACTA-ATAAT-CCTGAACAGAGGTA 690
         * *  *** *     *  * * *   * *   *  *   *   * **** bas      CTCCTCTTTAAATGTCTGG---GAGTACTACACATATGTAAAGATGATGCCCACTTACAA 722
cypa     GTAACATGCAACTGTATGCATTGCGAACTACGCAT-TTTGATGACATGACATGTCATTAA 749
          *    *   * **     * * *** *  *   * **    *     ** bas      AGAACGAGGACACCACTTA---AACCGGGTGTA----CAAAGTACTACACATATGTAA-- 773
cypa     ATAATGAAAACAGTCTTGTGGTAACTAGCTATGTTACCATAACACAAGACATGTCTAAGT 809
         *    *  *       ***  * *    ** *  ** * **** * *** bas      -AGATGAGGCCATAG---AACAAGCAAGAGCACCAAGATATTTAGATCCACTAAAATGCA 829
cypa     AAGATGAGTCTATGATATAATAAATGAGATATTCCATAAAACTAGAT---ATAAGTTACT 866
          *******  * **    ** **   ***    *  *   ** *****  ***  *
```

FIG. 12

```
bas   ACCACCTC----GATGTCCATAAAAAATGATGGTG-ACGTACAACA-------------- 870
cypa  ACCCACTCTGAAGATGATAACAAAGAATAGTAATGCACGCATGACAATACACTATTTACT 926
      *  *    ****   * * *  *   * *  *** bas   ----CTCAACAAATAT---CGATAAAAATGATAGTGTCCTAGTTGCA-CATCTTCTAACA 922
cypa  AGTCTTCTGTAAATTTATCCGATCAAAATGGCC-TGCTCGGGTTGCAATGCATTCTCACG 985
             ** *   ** **     *  ****** * bas   TGTTG--GTGTCTATTATGCAC---AAGTGGGCATGGAAGCAAGTAAATATTG-TGTACT 976
cypa  TGTTGAAGTTTCTGATATCGATGTAAGGTGGTCATACAAG-ACGAGAATACCAATGGAGT 1044
      ***   * *  *       * ** *  *** * *  **    * * bas   A-TAGCTACTGGTGACTCGAGTGTATCTCCAAGACTCGATAGCAAACCCGAAGCCTCTTC 1035
cypa  ACTAGATCTCGATGGACTAAGCATATGCAAATTTTATCTGAACAAGAAGCAGGCTTACTC 1104
      * ***  *    * *     ***     *       *  ***   *   ** *   ** bas   AGCTTGTCGACATATCATTGTGGAATGTT-CACTACGACTCGCCACGC-CAAGCATAACC 1093
cypa  AGGTTG-CAATGTATTCTCACGTACTGTTGCCTTGCTCCAGACGACCCGCATGCAAAAGC 1163
       *  *   ***  *    *  *****  *    *       *  * ** *  * ** * bas   TGGATAAGCCACGTGGGATATGAGATTTCCCGCAGCTTCCCTCTGAGTGAGGAGGCAGAA 1153
cypa  GAGCTTGTCCCCTAGAGTTGTGAA------TACTAGTTTCATTAGAAACATCACGTACTG 1217
       *      * *   * *  ***       *    ** *  **     *   *  * * bas   CTATACGCCTCAACACGACGAGCCACCCCCTAAGGCTAGTCATAGTGGGAGTAACTTGGG 1213
cypa  CGAAAGCCATTAATGCCTCTGTGAACACAATCGGGC-AGTATTGACTAGAATCTCCAAGA 1276
      * *    * ** *      *   *     **  *   * * *      *  * bas   TAGTAACATATTCCTACATATATTGCGAACTAAGCATTTAGATGACATGACATGCAATTA 1273
cypa  TCAGGCCATG-----AAATTAGTTGTTTACTTGATAATATTGTC-CAAGAGTTAGGGTTT 1330
      *     ***           *  * *   *    **  *  * *    *  ** bas   AATGATGAGAGAGAGTCTTATGATAACTAGCTATGTTACCATAACATCACACATTTC-TA 1332
cypa  A--GGTCAAGTAGAGGCC-GTGGCTTTTTTCCATTTCTCCATAATAAAAGGGCTTAGGTC 1387
      *   *  *    ****  *  **    *  *    * *  **** *   **   * bas   AAAAAATAAATCTATATTATAATAAATAAGGTTTTGCATGATACCA----CATCTATGT- 1387
cypa  AAGTAGTAGCTGCCTAT----ATAAATGAGGCATTGCGGGGTTCCTTACTCACTTGTGTG 1443
      **   * **  *          **** *  **** *    *       * *** bas   TATTTTGCACTATGAAGATAGTAACTTAGACTAGT--AACATATACATGTTACTA----CT 1442
cypa  CATTGACTGCTACCAGCTGTGTGCTGGACACTCGTTCACAGTGAACCAGTCAGGAGGATT 1503
       *    *  *       **    * *      *         *       * bas   CTAAGTTACTCCCCACA-ATGACCAGCCTAACACCTTTTGTACTGTTTTGCACATTTGCA 1501
cypa  TCAAATTCGTATTCAGGTATGCTTGATTTTAGTTTTAAGTCATATGA-GTTCATTTTTA 1562
       ** **  *      ** ***        * **   **  ** * *   *****    *
CTGGTGCA
bas   GTTTACTTTTTCTTAGGTGAAGAGAAAACACAAGACATAATTTTAATATTTCAACTTCAT 1561
cypa  GATCATTTTTTCATACGAGA-GAAATAAGACTAGGGCTAGGTTTGTT-------CTTCAT 1614
      *  * ****   *   ** * *  *  *       *        ****** bas   TACGTGCTGGTGCAAATAATTTTTACGGTGCAATTTTCGACATGATTTATTGTATATTTA 1621
cypa  ATGGGCCGGGTGCAAC--ATTTCGATA--ACAATCACGCATCAGAGCTATTACTTGTTCT 1670
       *  * *****  **  *    **** *   ** *    **  * ** bas   CAGAAATTTATGCTCCAAATTTGTTTGGTACCTTCAGTATTAGTTTCTGGACATTGTACA 1681
cypa  TCTGAATTT----TCTATAGCCTTTAAAAACCGACAATCAGAGTTCA-----ATTACCAA 1721
         *****      *    *   *  ** *  *  *  **         *  * bas   TATTATGTTGCCGTATAAGCTGAG-CTAGAAGGATCATTAGTGTAATTCCATATATATCT 1740
cypa  TCTAGTCTTGGT-CATATTTTGTTTCTTAATGAAGTGTTTTTGCTTCACTTTGTCCTTGT 1780
        *  *  ***    ***     ***    **     **  ***    *   * *
```

FIG. 12 Cont'd

```
bas     AAATGTACCTGTGGAATCACATTTGAGGAAGTTCCAATGATGCCCTTTTTGCCCTGCACA 1800
cypa    GGAGTCGAATGTGGCTTCCTGTTTAGACTGTTAGCTAGGTTCACCCTTTCAGATTTC-TT 1839
         *     ***     ***         *  *  *  *    *        * * bas     CGCATATATAAGAACCCTTTGCCCGCAGCATAGAGCTAGTACTAGCTAGTATCCCATTGC 1860
cypa    CATACTAATTATCTTCATATTCTGCCAGTGTGAATCCTCTAGTCAATAACGACATGGCAC 1899
         *  *   ** *      * * *   *** *  *    ** *    **     *     * bas     TTGTTTTCCTCGCATACACTGCCCGTTGTTGGTGCGCACC 1900
cypa    C--------------------------------------- 1900
```

FIG. 12 Cont'd.

ROOT SPECIFIC PROMOTERS

CROSS REFERENCE TO RELATED APPLICATIONS

This application claims the priority benefit of U.S. Provisional Patent Application Ser. No. 60/865,936 filed Nov. 15, 2006, which is incorporated herein by reference.

FIELD OF THE INVENTION

The present invention relates generally to methods and materials for use in tissue specific expression. In particular it relates to the promoters of genes for two enzymes responsible for plant avenacin biosynthesis (an oxidosqualene cyclase and a cytochrome P450).

BACKGROUND OF THE INVENTION

Plants synthesise a diverse range of natural products. Many of these compounds are specialised metabolites that are produced only by certain taxonomic groups (1). Plant-derived natural products have important ecological functions, often serving as attractants or deterrents in interactions with other organisms (1,2). The ability to synthesise particular natural products is therefore likely to be a consequence of niche colonisation and adaptive evolution (2,3). Currently we know very little about how new metabolic pathways arise. A better understanding of the origin and nature of the genes and enzymes that comprise natural product pathways will enable us to probe the mechanisms underpinning the generation of metabolic diversity.

Avenacins are antimicrobial triterpene glycosides (saponins) that accumulate in the roots of oats (*Avena* spp.) (4,5). The ability to synthesise avenacins is restricted to members of the genus *Avena* (4) and has arisen relatively recently—since the divergence of oats from other cereals and grasses (6). The major avenacin, A-1, contains the fluorophore N-methyl anthranilic acid and so confers a bright blue fluorescence on the roots of oat seedlings under ultraviolet illumination. In previous work we have exploited this fluorescence as a screen to isolate saponin-deficient (sad) mutants of diploid oat (*Avena strigosa*) following chemical (sodium azide) mutagenesis (5). sad mutants are compromised in disease resistance to a range of fungal pathogens, demonstrating that avenacins confer broad-spectrum protection against microbial attack (5). These experiments have provided the first direct evidence for a role for preformed antimicrobial compounds in plant defence.

Avenacins are synthesised from the isoprenoid pathway and share a common biogenetic origin with sterols, the two pathways diverging after 2,3-oxidosqualene (FIG. 1) (4, 7-9). In primary sterol biosynthesis 2,3-oxidosqualene is cyclised to cycloartenol by cycloartenol synthase. Cycloartenol is then converted to other sterols via a series of intermediates that includes obtusifoliol. The first committed step in the avenacin pathway is the cyclisation of 2,3-oxidosqualene to the triterpene precursor β-amyrin, catalysed by the oxidosqualene cyclase enzyme β-amyrin synthase (7-9). β-Amyrin is not antimicrobial but is converted to the biologically active avenacins by a series of uncharacterised modifications that are predicted to involve oxidation, glycosylation and acylation (9).

From genetic analysis of our mutant collection we originally defined eight loci for avenacin synthesis (Sad1-8).

We have previously cloned Sad1, the gene encoding β-amyrin synthase (FIG. 1) (8), (and see Haralampidis et al., PNAS Vol. 98, No 23, pp 13431-13436, Nov. 6, 2001; see also WO01/46391), but have not previously reported the sequence of the functional promoter of this gene. Our data indicate that Sad1 is likely to have been recruited from sterol metabolism by duplication and divergence of a plant cycloartenol-synthase like gene and that this is a relatively recent evolutionary event (6,8). Remarkably, six of the seven other Sad loci that we have defined by mutation (Sad-2,3,5,6,7 and 8) co-segregate with Sad1, indicating that the genes for avenacin biosynthesis are clustered (5,6). Although many examples of clustered genes for natural product pathways have been reported in microbes, gene clusters of this kind are not a common phenomenon in plants (2,6). The reason for clustering of avenacin biosynthetic genes is not yet known.

WO2006/044508, (see also Qi et al., PNAS, Vol. 101, No. 21, pp. 8233-8238, May 25, 2004) relate to the cloning of the Sad2 gene, although limited information was provided about the function and specificity of the promoter of that gene.

The CYP51 sterol demethylases are regarded as the most ancient cytochrome P450 family. They are highly conserved across the animal, fungal and plant kingdoms and are only known to have a single strictly conserved function—in the synthesis of essential sterols (10-13). AsCYP51H10 belongs to a new subfamily of divergent plant CYP51 enzymes (CYP51H) that until now has been defined only by rice sequences of unknown function (11). This subfamily is not represented in *Arabidopsis* or other dicots. Our data indicate that AsCYP51H10 has undergone neofunctionalisation and is required for the synthesis of defence-related antimicrobial triterpene glycosides (avenacins) but is dispensable for primary sterol biosynthesis. To our knowledge this is the first report of a CYP51 enzyme that has acquired a new function. Our demonstration that both Sad1 (6, 8) and Sad2 (AsCyp51H10) have been recruited from plant primary sterol metabolism indicates an intimate evolutionary connection between the sterol and avenacin pathways. However the expression patterns of Sad1 and Sad2 have been refined. While their sterol biosynthesis counterparts (the cycloartenol synthase and obtusifoliol 14α-demethylase genes, respectively) are expressed constitutively throughout the plant, expression of Sad1 and Sad2 (which are 70 kb apart) is tightly regulated and is restricted to the epidermal cells of the root tip, the site of accumulation of avenacins.

The promoters from genes which are tissue specific (e.g. root, or root-tip specific) have utility inter alia in expressing transgenes in this manner. Thus it can be seen that the characterisation of the sequences and specificity of such promoters provides a contribution to the art.

SUMMARY OF THE INVENTION

Disclosed herein are the sequences and specificity of the promoter of the Sad1 and Sad2 genes. These promoters have been characterized and shown to be tightly regulated and restricted to expression in the epidermal cells of the root tip and lateral roots, the site of accumulation of avenacins.

Interestingly, promoter reporter fusion experiments show that these promoters show similar patterns of expression as they do in oat when transformed into *Arabidopsis* and rice as reporter constructs. This is surprising, given that one would have expected there to be a specific transcription factor dedicated to the avenacin pathway only represented in oats. The fact that these two promoters plug into appropriate regulatory mechanisms in other diverse species is critically important to their use in those species.

The earlier disclosure of the Sad1 gene did not disclose the full sequence of the promoter (see Haralampidis et al.; WO01/46391 mRNA).

The earlier disclosure of the Sad2 gene did not disclose its function as a root specific promoter (see WO2006/044508; Qi et al).

In this patent disclosure we report the cloning and characterisation of the complete Sad1 promoter as well as a second gene and its promoter in the avenacin pathway, Sad2 (AsCyp51H10), which encodes a cytochrome P450 enzyme belonging to the CYP51 sterol demethylase family.

CYP51 sterol demethylases are the only cytochrome P450 enzymes with a conserved function across the animal, fungal and plant kingdoms (in the synthesis of essential sterols). These highly conserved enzymes, which are important targets for cholesterol-lowering drugs, antifungal agents and herbicides, are regarded as the most ancient member cytochrome P450 family. Here we present the first report of a CYP51 enzyme that has acquired a new function. We show that the plant enzyme AsCYP51H10 is dispensable for synthesis of essential sterols and has been recruited for the production of antimicrobial compounds (avenacins) that confer disease resistance in oats. The AsCyp51H10 gene is synonymous with Sad2, a gene that we had previously defined by mutation as being required for avenacin synthesis. In earlier work we showed that Sad1, the gene encoding the first committed enzyme in the avenacin pathway (β-amyrin synthase), had arisen by duplication and divergence of a cycloartenol synthase-like gene [Haralampidis, K. et al. (2001) *Proc. Natl. Acad. Sci. USA* 98, 13431-13436; Qi X et al. (2004) *Proc. Natl. Acad. Sci., USA* 101, 8233-8238].

Sad1 and Sad2 lie within 70 kb of each other and are expressed specifically in the epidermal cells of the root tip, the site of accumulation of avenacins.

With respect to the two promoters identified herein, we show that heterologous expression can be directed to the plant root tip by operatively linking these promoters to heterologous gene sequences. Likewise, utilizing these promoters to drive expression of the oat avenacin biosynthetic genes, heterologous expression in other plants (monocots and dicots) including in cereals (barley, wheat, rice etc) other than oats is enabled to control soil borne diseases such as "take-all", *Fusarium*, and other root-infecting pathogens. There is as yet no effective form of take-all resistance in wheat germplasm, a resistance which has been demonstrated in oat due to the unique expression in this plant crop of the avenacins. Likewise, resistance to *Fusarium* and other root-infecting pathogens is an as yet not fully met need. We show that these promoters (Sad1, the gene encoding β-amyrin synthase, the first committed enzyme in the pathway, and Sad2, which encodes a CYP450 that also acts early in the pathway) retain their characteristic expression patterns when introduced into *Arabidopsis* and rice. These promoters therefore have broad utility across diverse plant species for targeted gene expression in roots. Our data indicate substantial sequence divergence of the pathway components that have been characterized to date since the separation of oats from other cereals in evolutionary time. Although the pathway is missing from closely related cereals, and yet precisely because they are closely related, one could reasonably expect the pathway to function in other cereals upon introduction of the pathway into such commercially valuable crops.

In one aspect the invention provides a promoter exhibiting root-specific expression of genes operatively linked to said promoter, wherein said promoter is selected from the group consisting of the oat beta amyrin synthase promoter, the oat CYP51H10 promoter, operative portions thereof, and variants thereof which have between about 70 and 100 percent nucleic acid sequence homology therewith.

In another aspect the invention provides a method for achieving root-specific expression of a gene in a plant which comprises operatively linking the nucleic acid sequence encoding said gene with a root-specific promoter, wherein said promoter is selected from the group consisting of the oat beta amyrin synthase promoter, the oat CYP51H10 promoter, operative portions thereof, and variants thereof which have between about 70 and 100 percent nucleic acid sequence homology therewith.

In one embodiment the nucleic acid comprises the entire sequences of FIG. 9 (SEQ ID NO: 181) or 10 (SEQ ID NO: 182) respectively, or active fragments (operative portions) thereof.

"Nucleic acid" and "nucleic acid molecule" have the same meaning. The nucleic acids of the invention may consist essentially of a nucleotide sequence of the present invention (which is to say that the sequence is 'of the essence of' the molecule, generally making up more than 50% of it).

The nucleic acid molecules or vectors (see below) according to the present invention may be provided isolated and/or purified from their natural environment, in substantially pure or homogeneous form, or free or substantially free of nucleic acid or (other) genes of the species of interest or origin. The term "isolated" encompasses all these possibilities.

Complement sequences of those discussed herein are also encompassed. As is well understood by those skilled in the art, two nucleic acid nucleotide sequences are "complementary" when one will properly base pair with all or part of the other according to the standard rules (G pairs with C, and A pairs with T). One sequence is "the complement" of another where those sequences are of the same length, but are complementary to each other.

Thus in one aspect the invention provides an isolated nucleic acid, comprising:
(i) the oat beta-amyrin synthase promoter shown in FIG. 10 (SEQ ID NO: 182), or
(ii) the oat AsCYP51H10 promoter shown in FIG. 9 (SEQ ID NO: 181), or
(iii) a promoter sequence which is a variant of the promoter sequence of (i) or (ii), and shares at least about 70%, 80% or 90% identity with the respective promoter, or
(iv) a promoter sequence which is an operative portion of the promoter sequence of (i) or (ii).

In one embodiment the promoter sequence is a variant or operative portion of the oat beta-amyrin synthase promoter comprising at least at 500, 600, 700, 800, 900, 1000 contiguous nucleotides of the sequence of nucleotides shown as 1 to 1057 in FIG. 10 (SEQ ID NO: 182).

Variants

Variants of the present invention (of promoters or coding sequences) can be artificial nucleic acids (i.e. containing sequences which have not originated naturally) which can be prepared by the skilled person in the light of the present disclosure. Artificial variants (derivatives) may be prepared by those skilled in the art, for instance by site directed or random mutagenesis, or by direct synthesis. Preferably the variant nucleic acid is generated either directly or indirectly (e.g. via one or amplification or replication steps) from an original nucleic acid having all or part of the sequences of the first aspect. Preferably the variant encodes a product which has one or more of the transcription factor activities discussed above.

Alternatively they may be novel, naturally occurring, nucleic acids, isolatable using the sequences of the present invention. Sequence variants which occur naturally may also include alleles (which will include polymorphisms or mutations at one or more bases).

Artificial changes, which may be by way of base substitution, deletion, or addition, may be desirable for a number of reasons, including introducing or removing restriction endonuclease sequences, or altering the length, strength, or specificity of the promoter with respect to the native promoter. For instance it may be desirable to remove motifs which may bind transcriptional factors and thereby reduce specificity.

Specifically, variants may include promoters which have been extended at the 3' or 5' terminus.

Also included are fragments or other portions of the native sequences, however produced, having the requisite activity as described above. For instance restriction enzymes or nucleases may be used to digest a nucleic acid molecule, or mutagenesis may be employed, followed by an appropriate assay (for example using a reporter gene such as luciferase—see below) to determine the sequence required. Portions may also be isolated by use of specific primers to amplify selected motifs or other elements, for instance by PCR.

Chimaeric promoters having the minimal elements or motifs responsible for root specific regulation, possibly in conjunction with other promoter sequences (e.g. taken from known plant promoters) form another part of the present invention.

A variant promoter of the present invention will have root-specific promoter activity and will share at least about 70%, or 80% identity, most preferably at least about 90%, 95%, 96%, 97%, 98% or 99% identity with the native promoter.

Similarity or identity between the variant and the native promoter from which it is derived may be as defined and determined by the TBLASTN program, of Altschul et al. (1990) *J. Mol. Biol.* 215: 403-10, which is in standard use in the art, or, and this may be preferred, the standard program BestFit, which is part of the Wisconsin Package, Version 8, September 1994, (Genetics Computer Group, 575 Science Drive, Madison, Wis., USA, Wis. 53711).

Testing Promoter Activity

For suitably homologous promoter sequences, the level of activity may be quantified, for instance by using the expression methods described herein.

Activity can then be assessed by the amount of mRNA produced by transcription from the promoter, or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction.

Use of a reporter gene facilitates determination of promoter activity by reference to protein production. The reporter gene preferably encodes an enzyme which catalyses a reaction which produces a detectable signal, preferably a visually detectable signal, such as a coloured product. Many examples are known, including β-galactosidase, luciferase and green fluorescent protein (GFP). β-glucoronidase (GUS) activity may be assayed as described in the Examples below.

Vectors Including Promoter

In one aspect, the invention provides nucleic acid (e.g. an expression cassette) comprising a promoter sequence as discussed above operably linked to a heterologous gene.

"Operably linked" means joined as part of the same nucleic acid molecule, suitably positioned and oriented for transcription to be initiated from the promoter. DNA operably linked to a promoter is "under transcriptional initiation regulation" of the promoter.

The term "heterologous gene" includes any sequence which it is desired to transcribe and which is non-naturally occurring contiguosly with the promoter. It includes, for example, any of: a sequence complementary to a native plant gene; a biosynthetic gene; a pathogen resistance gene and so on.

The promoters of the present invention have been shown to work in the root tip and lateral root initials (i.e. root meristematic regions) and so also may have utility for expression of nodule-related genes for transferal of nitrogen fixation capability.

In one embodiment the nucleic acid is a vector, more preferably an expression vector.

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

In one aspect, the invention provides a cell comprising or transformed with a vector discussed above.

Suitable vectors, and appropriate host cells, can be readily chosen or constructed, containing appropriate regulatory sequences, including terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, Second Edition, Ausubel et al. eds., John Wiley & Sons, 1992. Inasmuch as these references disclose more than the common general knowledge of the person skilled in this art, the disclosures of Sambrook et al. and Ausubel et al. are incorporated herein by reference.

Plants

Particularly of interest in the present context are nucleic acid constructs and vectors which operate in plants.

If desired, selectable genetic markers may be included in the vector, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

In one aspect, the invention provides a plant cell comprising or transformed with a heterologous nucleic acid or vector discussed above.

The term "heterologous" is used broadly in this aspect to indicate that the nucleic acid of the invention has been introduced into said cells of the plant or an ancestor thereof, using genetic engineering, i.e. by human intervention. A heterologous gene may replace an endogenous equivalent gene, i.e. one which normally performs the same or a similar function, or the inserted sequence may be additional to the endogenous gene or other sequence.

In another embodiment there is provided a method of making a transformed plant cell, comprising transforming a plant cell with a vector of the invention as described herein.

Thus a further aspect of the present invention provides a method of transforming a plant cell involving introduction of a vector as described above into a plant cell and causing or allowing recombination between the vector and the plant cell genome to introduce a heterologous nucleic acid into the genome e.g. such as to achieve root specific expression as discussed above.

Optionally the plant cell is a root cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

Nucleic acid can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

*Agrobacterium* transformation is widely used by those skilled in the art to transform dicotyledonous species. Recently, there has also been substantial progress towards the routine production of stable, fertile transgenic plants in almost all economically relevant monocot plants (see e.g. Hiei et al. (1994) *The Plant Journal* 6, 271-282)). Microprojectile bombardment, electroporation and direct DNA uptake are preferred where *Agrobacterium* alone is inefficient or ineffective. Alternatively, a combination of different techniques may be employed to enhance the efficiency of the transformation process, eg bombardment with *Agrobacterium* coated microparticles (EP-A-486234) or microprojectile bombardment to induce wounding followed by co-cultivation with *Agrobacterium* (EP-A-486233).

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

Generally speaking, following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The generation of fertile transgenic plants has been achieved in the cereals rice, maize, wheat, and barley (reviewed in Shimamoto, K. (1994) *Current Opinion in Biotechnology* 5, 158-162; Vasil, et al. (1992) *Bio/Technology* 10, 667-674; Vain et al., 1995, *Biotechnology Advances* 13 (4): 653-671; Vasil, 1996, *Nature Biotechnology* 14 page 702).

In one aspect, the invention provides a plant transformed with a vector discussed above.

The plant may optionally have been regenerated from the plant cell described above.

In another embodiment there is provided a method of making a transformed plant, comprising transforming a plant with a vector of the invention as described herein.

In addition to the regenerated plant obtainable by the above method, the present invention embraces all of the following: a clone of such a plant; selfed or hybrid progeny; descendants (e.g. F1 and F2 descendants) and any part of any of these. Such progeny will include a heterologous nucleic acid, expression cassette or vector of the invention.

The invention also provides a plant propagule from such plants, that is any part which may be used in reproduction or propagation, sexual or asexual, including cuttings, and so on. In particular the invention also provides a seed of such plants, again including a heterologous nucleic acid, expression cassette or vector of the invention.

The invention also provides a method for directing root-specific expression of a gene, said method comprising introducing into a plant cell an isolated nucleic acid comprising a promoter of the invention operably linked to said gene, and regenerating a plant from said plant cell in order to effect said specific expression.

The invention also provides a method for modifying root development the method comprising use of any of said nucleic acids and vectors described above. For example the method may include the step of causing or allowing expression of the product (polypeptide or nucleic acid transcript) encoded by heterologous nucleic acid (e.g. under control of a promoter of the invention) from that nucleic acid within cells of the plant. The step may be preceded by the earlier step of introduction of the nucleic acid into a cell of the plant or an ancestor thereof.

Use of the nucleic acids described above (e.g. the Sad2 promoter sequence) for these methods and purposes forms a further aspect of the invention.

Figure 1:
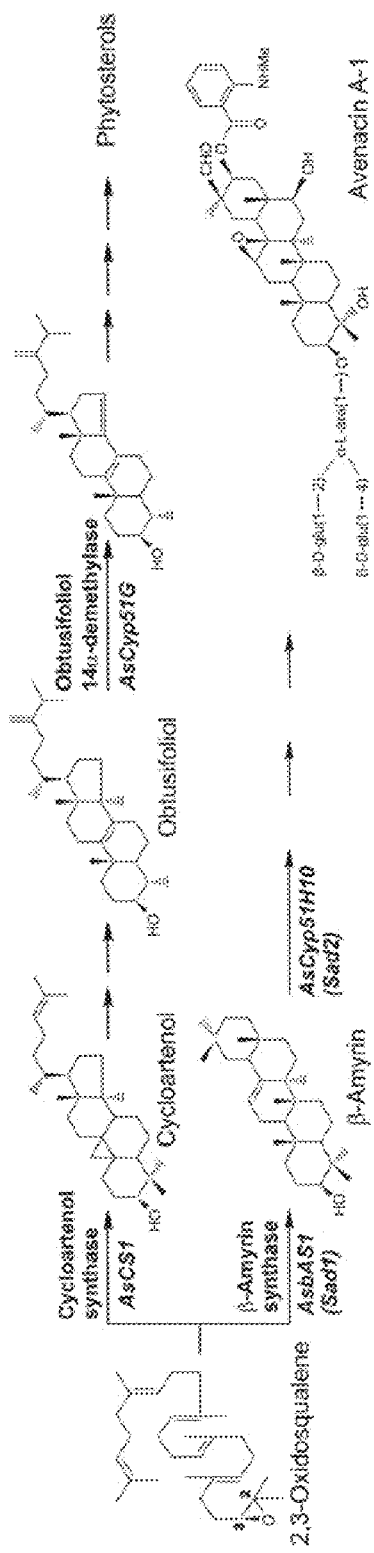
FIG. 1. Synthesis of sterols and defence-related triterpenes in oats. The sterol and triterpene pathways branch after 2,3-oxidosqualene. Key genes and enzymes are indicated.

(A) Alignment of selected regions of 36 representative CYP51 sequences from diverse organisms. The predicted substrate recognition sites (SRS) (16) are framed. Completely conserved amino acids are shown on a black background and those that are conserved in all except AsCYP51H10 on a grey background. Mutations in sad2 mutants in these regions are shown (mutant number preceded by "#"; changes marked with black dots). Residues that line the active site cavity are indicated by triangles. The filled triangles denote the subset of these which are likely to be key determinants in modulating the size and shape of the cavity in AsCYP51H10.

Row 1: MtCYP51B1: αB' (SEQ ID NO: 1); αI' (SEQ ID NO: 2); β1-4 (SEQ ID NO: 3); β4-2 (SEQ ID NO: 4); Row 2: MaCYP51B1: αB' (SEQ ID NO: 5); αI' (SEQ ID NO: 6); β1-4 (SEQ ID NO: 7); β4-2 (SEQ ID NO: 8); Row 3: MvCYP51B1: αB' (SEQ ID NO: 9); αI' (SEQ ID NO: 10); β1-4 (SEQ ID NO: 11); β4-2 (SEQ ID NO: 12); Row 4: TbCYP51E1: αB' (SEQ ID NO: 13); αI' (SEQ ID NO: 14); β1-4 (SEQ ID NO: 15); β4-2 (SEQ ID NO: 16); Row 5: TcCYP51E1: αB' (SEQ ID NO: 17); αI' (SEQ ID NO: 18); β1-4 (SEQ ID NO: 19); β4-2 (SEQ ID NO: 20); Row 6: LmCYP51E1: αB' (SEQ ID NO: 21); αI' (SEQ ID NO: 22); β1-4 (SEQ ID NO: 23); β4-2 (SEQ ID NO: 24); Row 7: AbsCYP51A1: αB' (SEQ ID NO: 25); αI' (SEQ ID NO: 26); β1-4 (SEQ ID NO: 27); β4-2 (SEQ ID NO: 28); Row 8: FHCYP51A1: αB' (SEQ ID NO: 29); αI' (SEQ ID NO: 30); β1-4 (SEQ ID NO: 31); β4-2 (SEQ ID NO: 32); Row 9: DrCYP51A1: αB' (SEQ ID NO: 33); αI' (SEQ ID NO: 34); β1-4 (SEQ ID NO: 35); β4-2 (SEQ ID NO: 36); Row 10: HsCYP51A1: αB' (SEQ ID NO: 37); αI' (SEQ ID NO: 38); β1-4 (SEQ ID NO: 39); β4-2 (SEQ ID NO: 40); Row 11: RatCYP51A1: αB' (SEQ ID NO: 41); αI' (SEQ ID NO: 42); β1-4 (SEQ ID NO: 43); β4-2 (SEQ ID NO: 44); Row 12: AfCYP51F1: αB' (SEQ ID NO: 45); αI' (SEQ ID NO: 46); β1-4 (SEQ ID NO: 47); β4-2 (SEQ ID NO: 48); Row 13: PdCYP51F1: αB' (SEQ ID NO: 49); αI' (SEQ ID NO: 50); β1-4 (SEQ ID NO: 51); β4-2 (SEQ ID NO: 52); Row 14: MfCYP51F1: αB' (SEQ ID NO: 53); αI' (SEQ ID NO: 54); β1-4 (SEQ ID NO: 55); β4-2 (SEQ ID NO: 56); Row 15: UnCYP51F1: αB' (SEQ ID NO: 57); αI' (SEQ ID NO: 58); β1-4 (SEQ ID NO: 59); β4-2 (SEQ ID NO: 60); Row 16: MgCYP51F1: αB' (SEQ ID NO: 61); αI' (SEQ ID NO: 62); β1-4 (SEQ ID NO: 63); β4-2 (SEQ ID NO: 64); Row 17: VnCYP51F1: αB' (SEQ ID NO: 65); αI' (SEQ ID NO: 66); β1-4 (SEQ ID NO: 67); β4-2 (SEQ ID NO: 68); Row 18: SDCYP51F1: αB' (SEQ ID NO: 69); αI' (SEQ ID NO: 70); β1-4 (SEQ ID NO: 71); β4-2 (SEQ ID NO: 72); Row 19: CaCYP51F1: αB' (SEQ ID NO: 73); αI' (SEQ ID NO: 74); β1-4 (SEQ ID NO: 75); β4-2 (SEQ ID NO: 76); Row 20: CgCYP51F1: αB' (SEQ ID NO: 77); αI' (SEQ ID NO: 78); β1-4 (SEQ ID NO: 79); β4-2 (SEQ ID NO: 80); Row 21: EgCYP51F1: αB' (SEQ ID NO: 81); αI' (SEQ ID NO: 82); β1-4 (SEQ ID NO: 83); β4-2 (SEQ ID NO: 84); Row 22: CnCYP51F1: αB' (SEQ ID NO: 85); αI' (SEQ ID NO: 86); β1-4 (SEQ ID NO: 87); β4-2 (SEQ ID NO: 88); Row 23: UmCYP51F1: αB' (SEQ ID NO: 89); αI' (SEQ ID NO: 90); β1-4 (SEQ ID NO: 91); β4-2 (SEQ ID NO: 92); Row 24: CrCYP51G1: αB' (SEQ ID NO: 93); αI' (SEQ ID NO: 94); β1-4 (SEQ ID NO: 95); β4-2 (SEQ ID NO: 96); Row 25: LeCYP51G1: αB' (SEQ ID NO: 97); αI' (SEQ ID NO: 98); β1-4 (SEQ ID NO: 99); β4-2 (SEQ ID NO: 100); Row 26: PoCYP51G1: αB' (SEQ ID NO: 101); αI' (SEQ ID NO: 102); β1-4 (SEQ ID NO: 103); β4-2 (SEQ ID NO: 104); Row 27: AqCYP51G1: αB' (SEQ ID NO: 105); αI' (SEQ ID NO: 106); β1-4 (SEQ ID NO: 107); β4-2 (SEQ ID NO: 108); Row 28: LjCYP51G1: αB' (SEQ ID NO: 109); αI' (SEQ ID NO: 110); β1-4 (SEQ ID NO: 111); β4-2 (SEQ ID NO: 112); Row 29: AtCYP51G1: αB' (SEQ ID NO: 113); αI' (SEQ ID NO: 114); β1-4 (SEQ ID NO: 115); β4-2 (SEQ ID NO: 116); Row 30: PtCYP51G1: αB' (SEQ ID NO: 117); αI' (SEQ ID NO: 118); β1-4 (SEQ ID NO: 119); β4-2 (SEQ ID NO: 120); Row 31: TaCYP51G1: αB' (SEQ ID NO: 121); αI' (SEQ ID NO: 122); β1-4 (SEQ ID NO: 123); β4-2 (SEQ ID NO: 124); Row 32: SbCYP51G1: αB' (SEQ ID NO: 125); αI' (SEQ ID NO: 126); β1-4 (SEQ ID NO: 127); β4-2 (SEQ ID NO: 128); Row 33: ZmCYP51G1: αB' (SEQ ID NO: 129); αI' (SEQ ID NO: 130); β1-4 (SEQ ID NO: 131); β4-2 (SEQ ID NO: 132); Row 34: OsCYP51G1: αB' (SEQ ID NO: 133); αI' (SEQ ID NO: 134); β1-4 (SEQ ID NO: 135); β4-2 (SEQ ID NO: 136); Row 35: AuCYP51G1: αB' (SEQ ID NO: 137); αI' (SEQ ID NO: 138); β1-4 (SEQ ID NO: 139); β4-2 (SEQ ID NO: 140); Row 36: AsCYP51H10 : αB' (SEQ ID NO: 141); αI' (SEQ ID NO: 142); β1-4 (SEQ ID NO: 143); β4-2 (SEQ ID NO: 144);

(B) Modelling of the active site cavity of AsCYP51H10 (bottom) and the oat sterol 14α-demethylase AsCYP51G1 (middle) based on the *Mycobacterium tuberculosis* MtCYP51B1 crystal structure (top).

(C) Phylogenetic analysis of CYP51 amino acid sequences. The numbers indicate the percentage of bootstrap replicates (out of 1000) in which the given branching was observed. Accession numbers for the sequences used in alignments, modelling and phylogenetic analysis are given in Supporting Table 2.

Figure 4:
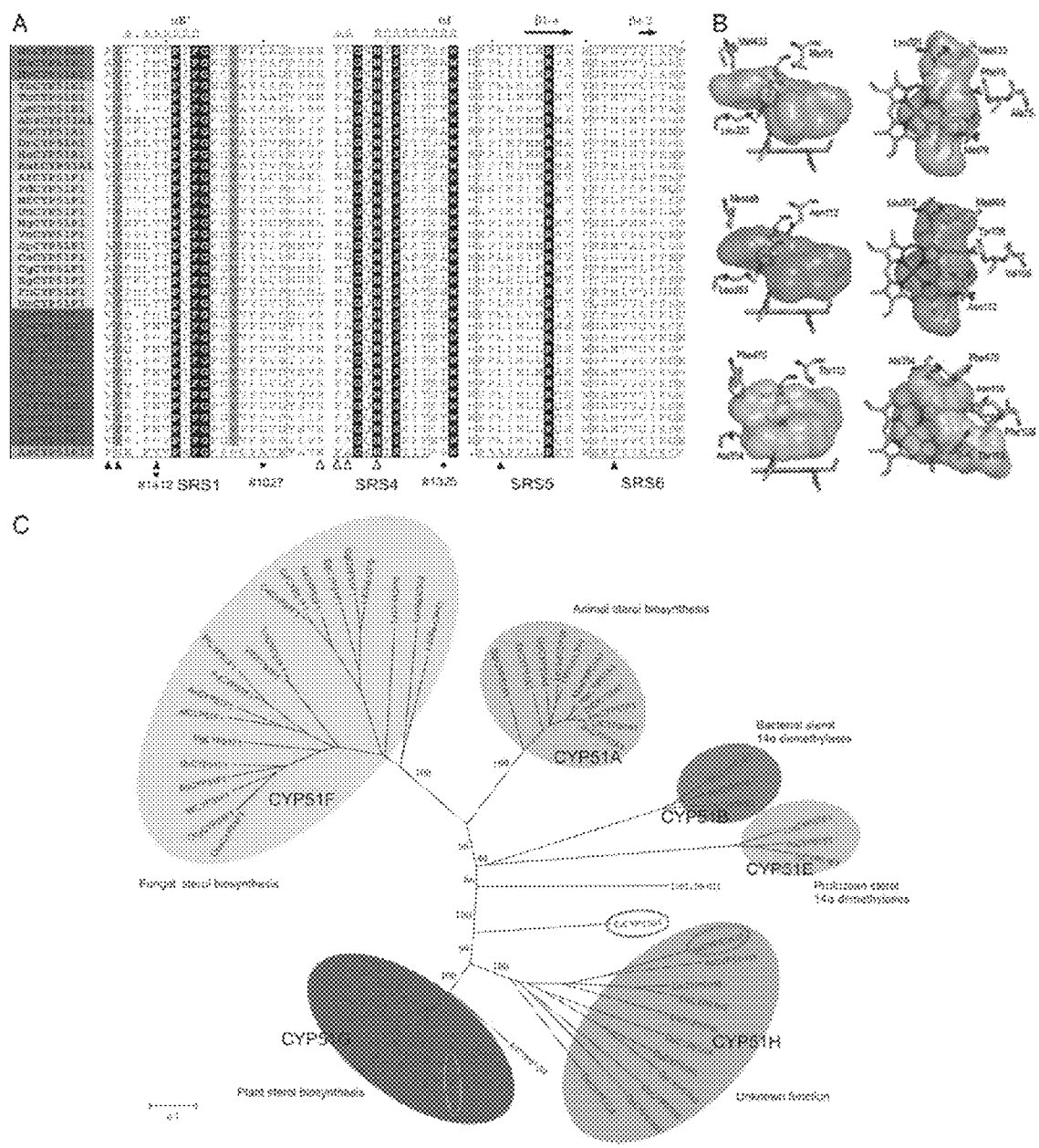
FIG. 4. Sequence and structure of AsCYP51H10.
Figure 5:
Figure 5:
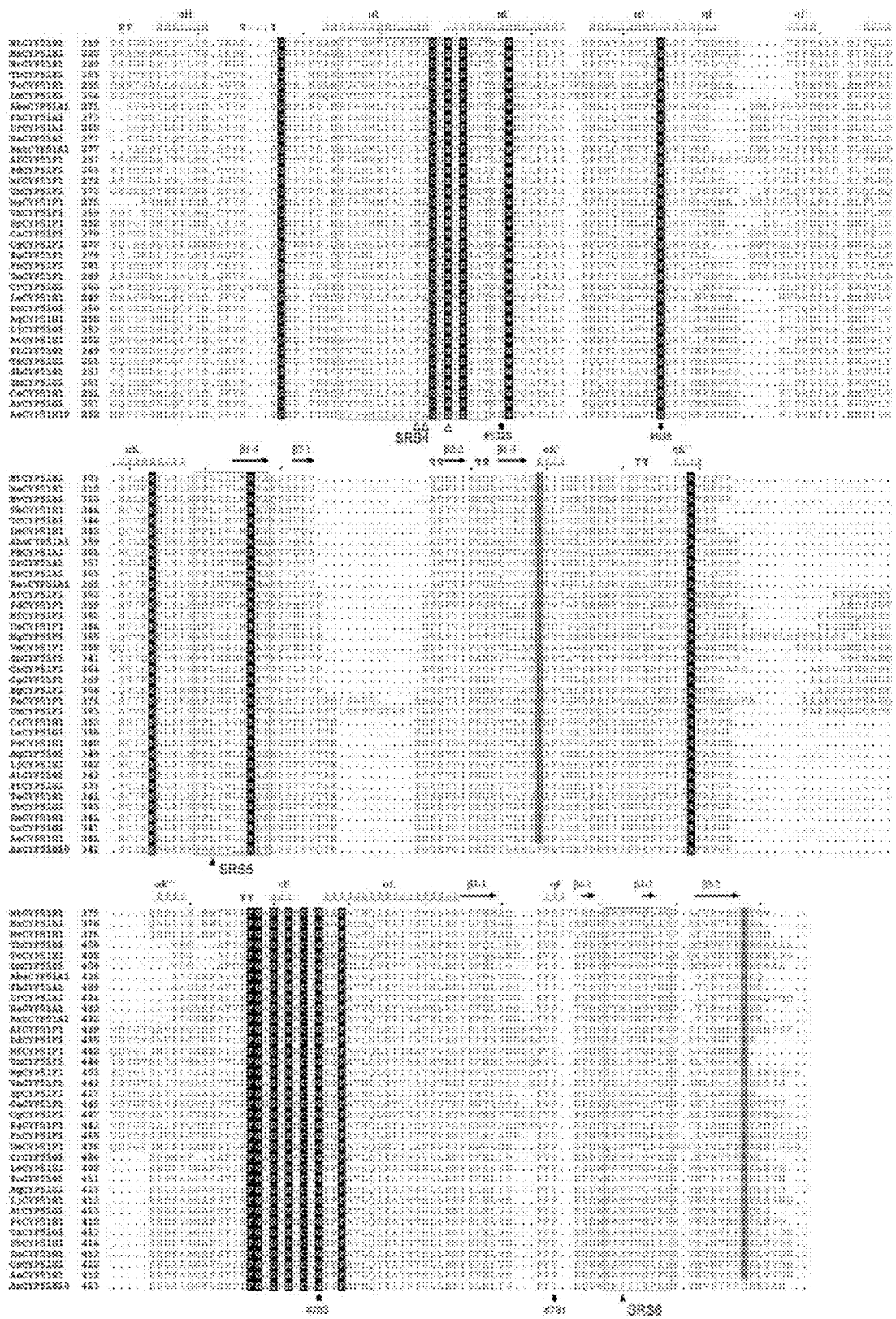

FIG. 5. Full length alignment of the 36 representative CYP51 sequences shown in FIG. 4A. Individual sequence information is given in Supporting Table 2. Alignment was performed using CLUSTER X, version 1.8, and manually adjusted according to Lepesheva et al (22), and displayed using ESPript (version 2.1) (23). Assignment of secondary structure elements is based on the MTCYP51B1 structure (16). The predicted substrate recognition sites (SRS) are framed. Black background, completely conserved amino acid residues; grey background, amino acid residues that are conserved in all members except AsCYP51H10. Mutations in sad2 mutants are shown (mutant number preceded by "#"; changes marked with black dots). Residues that line the active site cavity are indicated by triangles. The filled triangles denote the subset of these that are likely to be key determinants in modulating the size and shape of the cavity in AsCYP51H10. MtCYP15B1 (SEQ ID NO: 145); MaCYP15B1 (SEQ ID NO: 146); MvCYP51B1 (SEQ ID NO: 147); TbCYP51E1 (SEQ ID NO: 148); TcCYP51E1 (SEQ ID NO: 149); LmCYP51E1 (SEQ ID NO: 150); AbsCYP51A1 (SEQ ID NO: 151); FhCYP51A1 (SEQ ID NO: 152); DrCYP51A1 (SEQ ID NO: 153); HsCYP51A1 (SEQ ID NO: 154); RatCYP51A1 (SEQ ID NO: 155); AfCYP51F1 (SEQ ID NO: 156); PdCYP51F1 (SEQ ID NO: 157); MfCYP51F1 (SEQ ID NO: 158); UnCYP51F1 (SEQ ID NO: 159); MgCYP51F1(SEQ ID NO: 160); VnCYP51F1 (SEQ ID NO: 161); SlDCYP51F1 (SEQ ID NO: 162); CaCYP51F1 (SEQ ID NO: 163); CgCYP51F1 (SEQ ID NO: 164); EgCYP51F1 (SEQ ID NO: 165); FnCYP51F1 (SEQ ID NO: 166); UmCYP51F1 (SEQ ID NO: 167); CrCYP51G1 (SEQ ID NO: 168); LeCYP51G1 (SEQ ID NO: 169); PoCYP51G1 (SEQ ID NO: 170); AgCYP51G1 (SEQ ID NO: 171); LjCYP51G1 (SEQ ID NO: 172); AtCYP51G1 (SEQ ID NO: 173); PtCYP51G1(SEQ ID NO: 174); TaCYP51G1 (SEQ ID NO: 175); SbCYP51G1 (SEQ ID NO: 176); ZmCYP51G1 (SEQ ID NO: 177); OsCYP51G1 (SEQ ID NO: 178); AsCYP51G1 (SEQ ID NO: 179); AsCYP51H10 (SEQ ID NO: 180).

Figure 6:
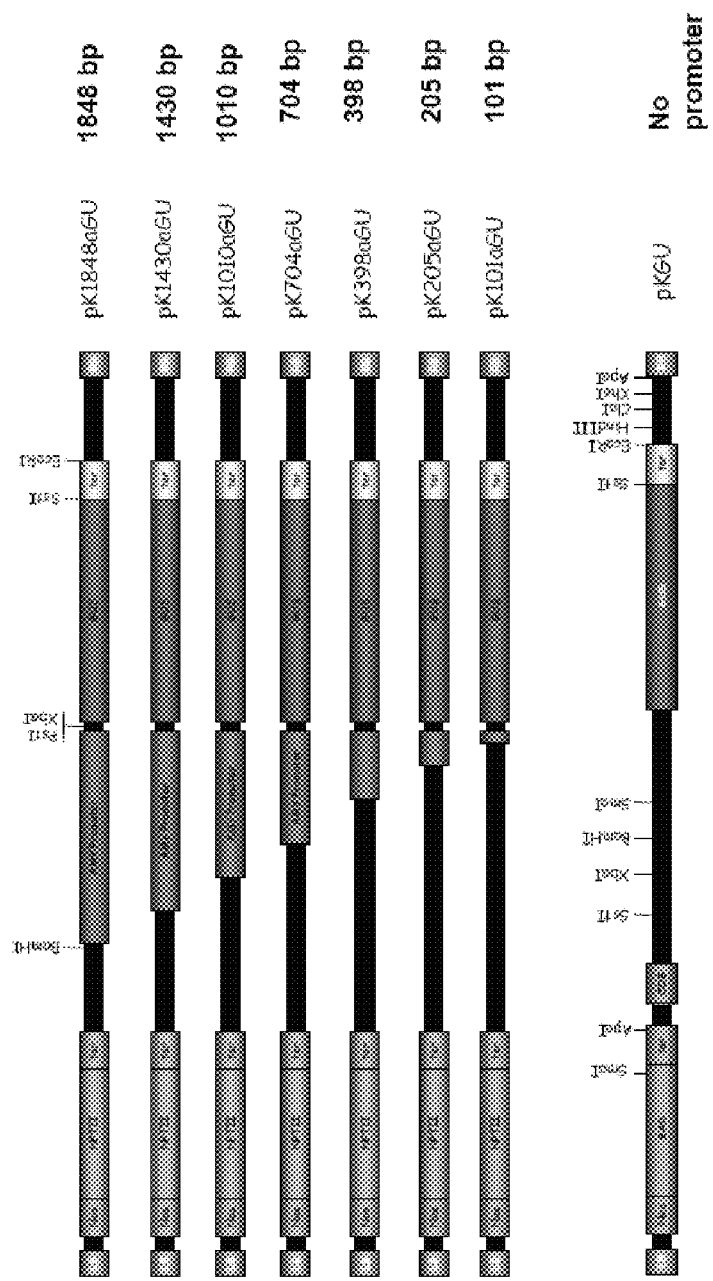

FIG. 6. Gene constructs which showed no expression of an heterologous gene.

Figure 7:
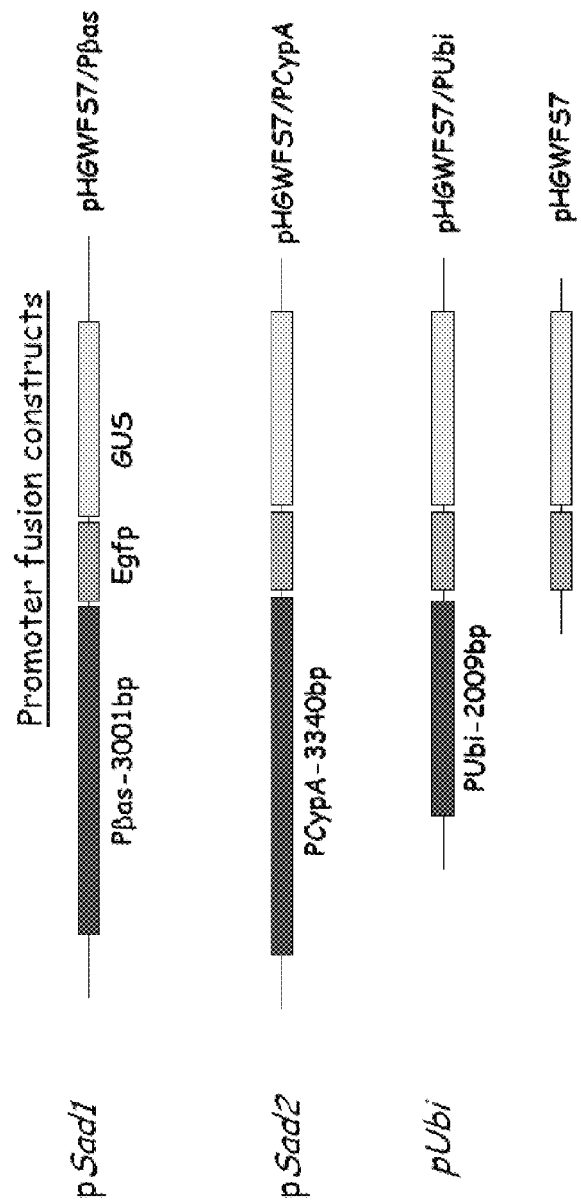

FIG. 7. Gene constructs which showed expression of an heterologous gene.

Figure 8:
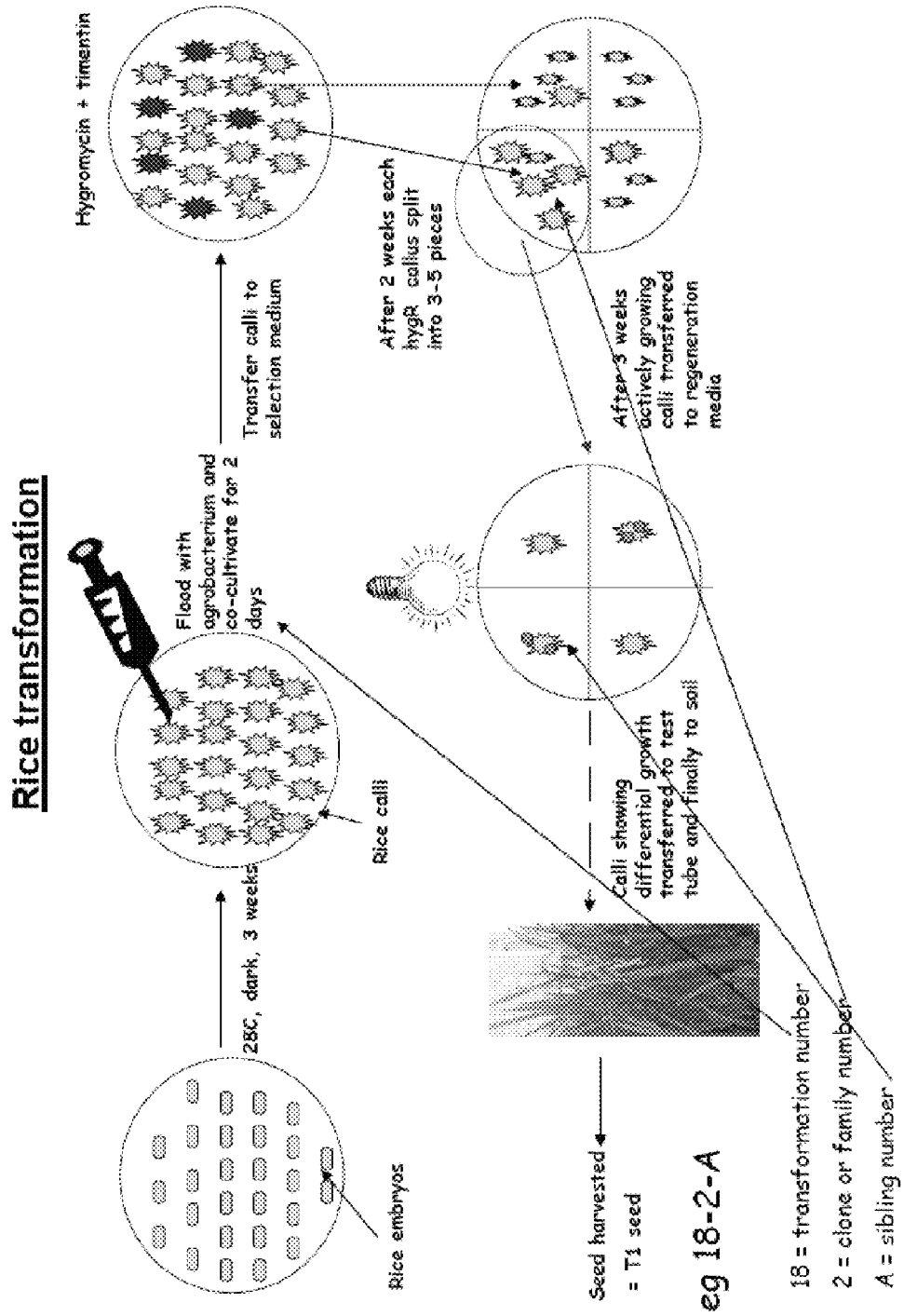

FIG. 8. Rice transformation methodology.

FIG. 9. AsCYP51H10 (Sad2) promoter sequence (SEQ ID NO: 181).

FIG. 10. Beta-amyrin synthase (Sad1) promoter sequence (SEQ ID NO: 182 (+ strand) and SEQ ID NO: 183 (– strand)).

FIG. 11. Clustal analysis and aligment of the AsCYP51H10 (Sad2) ("cypA") promoter sequence (SEQ ID NO: 181) and the beta-amyrin synthase (Sad1) ("bAS") promoter sequence (SEQ ID NO: 184).

FIG. 12. Clustal analysis and aligment of the AsCYP51H10 (Sad2) ("cypA") promoter sequence (SEQ ID NO: 186) and the beta-amyrin synthase (Sad1) ("bAS") promoter sequence SEQ ID NO: 185).

DETAILED DISCLOSURE OF THE INVENTION

Incorporated by reference herein is the entire disclosure of WO01/46391, which disclosed the cloning of the Sad1 gene and a non-functional portion of its promoter. We report here the sequence of the full, functional promoter of this gene and its root specific expression pattern. Likewise, while the cloning of the Sad2 gene was disclosed in WO2006/044508, the entire disclosure of which is incorporated here by reference, the function of the promoter associated with that gene as a root specific promoter was not disclosed. Further details with respect to the cloning and characterization of the function of these promoters is provided herein below.

A. Cloning of AsCyp51H10.

The avenacin gene cluster maps to the distal part of linkage group AswC of diploid oat in a region of the genome that is not conserved in other cereals (6). We have shown that the uncharacterised RFLP probe isu441, which is derived from a hexaploid oat cDNA library, maps within the avenacin gene cluster (6). We sequenced this 480-nucleotide cDNA and found homology with cytochrome P450 monoxygenases, the closest match being with wheat obtusifoliol 14α-demethylase (CYP51) (52% amino acid sequence identity) (14). Since cytochrome P450s are implicated in avenacin biosynthesis (9) this gene became a candidate pathway gene. We isolated and sequenced the full length cDNA and gene corresponding to isu441 from the diploid oat accession *Avena strigosa* S75 (the wild type parent of the sad mutants). The gene was designated AsCyp51H10.

Figure 2:
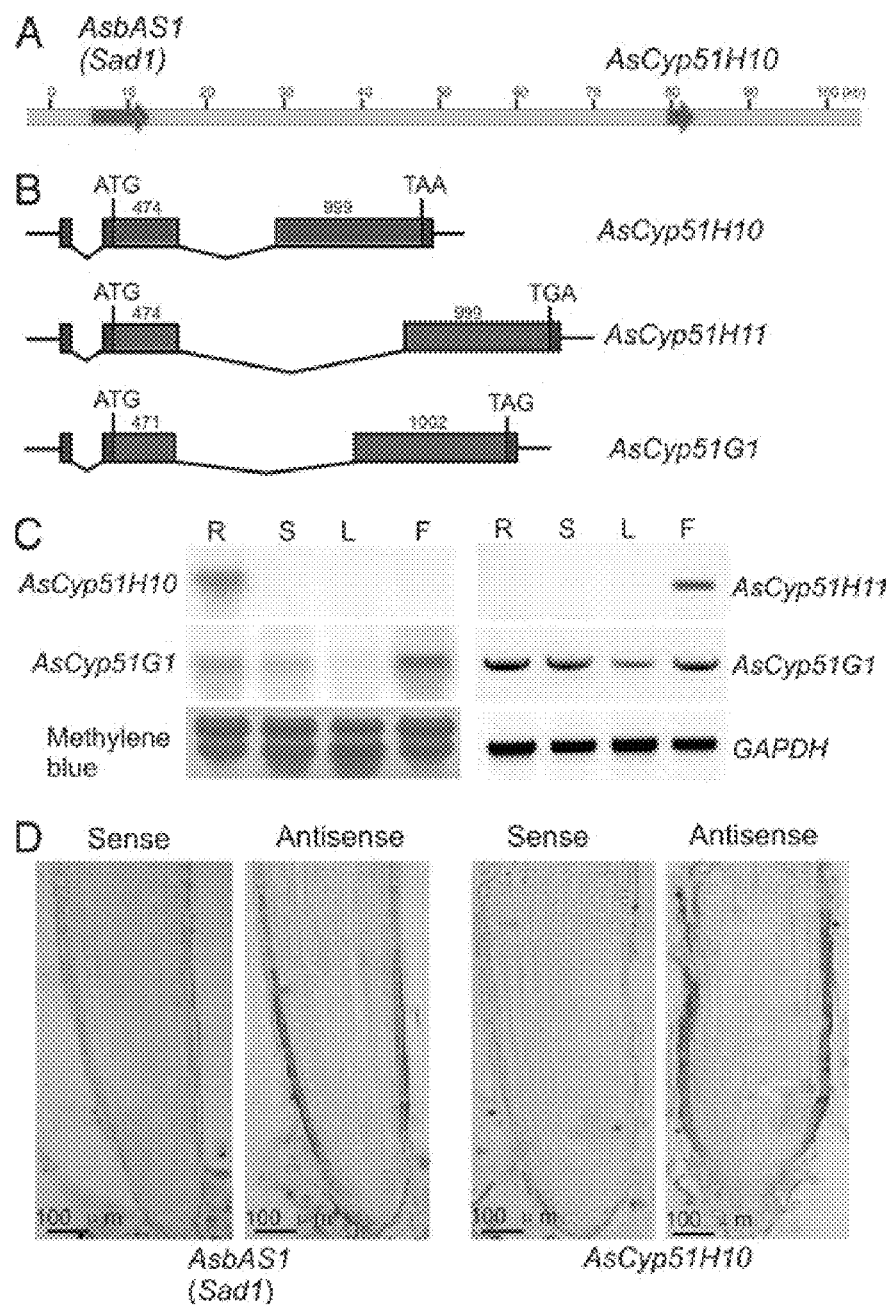
FIG. 2. Isolation and characterisation of AsCyp51H10. (A) BAC clone #B460D15 contains Sad1 and AsCyp51H10. (B) Gene structures of AsCyp51H10, AsCyp51H10 and AsCyp51G1. (C) Northern blot analysis of AsCyp51H10 and AsCyp51G1 transcripts (left panels) and RT-PCR analysis of AsCyp51H11 and AsCyp51G1 transcripts (right panels) in oat roots (R), shoots (S), leaves (L) and flowers (F). The oat glyceraldehyde 3-phosphate dehydrogenase gene (GAPDH) was used as a control for RT-PCR. (D) In situ mRNA analysis of Sad1 and AsCyp51H10 transcripts in the root tips of *A. strigosa*.

The AsCyp51H10 cDNA was used as a probe to screen a bacterial artificial chromosome (BAC) library that we constructed for A. strigosa S75. Six BAC clones spanning the Sad1 region were identified. Sequence analysis established that AsCyp51H10 is 66,828 base pairs from Sad1 and that the gap between these two genes contains repetitive sequences but no other obvious open reading frames (FIG. 2A). A seventh BAC clone mapped to a different linkage group (AswG) and contained a homologue of AsCyp51H10 (designated AsCyp51H11). AsCyp51H10 and AsCyp51H11 share 74% nucleotide sequence identity. The presumed oat obtusifoliol 14α-demethylase gene was not detected in our BAC screen. However we were able to identify sequences corresponding to this in an expressed sequence tag (EST) database of >16, 000 sequences that we had previously generated from oat roots (8). We then cloned and sequenced the full-length cDNA and the corresponding gene (designated AsCyp51G1).

AsCyp51H10 and AsCyp51H11 have 53% and 54% nucleotide sequence identity with AsCYP51G, respectively. AsCyp51G1 maps to a third linkage group, AswB.

B. Expression of AsCyp51H10 is Restricted to the Root Epidermis.

The gene structures of AsCyp51H10, AsCyp51H11 and AsCyp51G1 are very similar (FIG. 2B). All three genes are predicted to encode products 490 amino acids in length. The exon sizes of AsCyp51H10 and AsCyp51H11 are identical but differ from those of the obtusifoliol 14α-demethylase gene AsCyp51G, suggesting a closer evolutionarily relationship between the former two genes (FIG. 2B). The obtusifoliol 14α-demethylase gene AsCyp51G1 is expressed in all plant organs examined, consistent with a role in primary sterol metabolism (FIG. 2C). In contrast, AsCyp51H10 is expressed specifically in the roots while AsCyp51H11 transcripts were detected only in the flowers (FIG. 2C). Synthesis of avenacin A-1 is under tight regulation and is restricted to the epidermal cells of the root tip (8). Previously we have shown by mRNA in situ hybridisation that expression of Sad1 is restricted to this cell type (8). AsCyp51H10 showed a very similar pattern of expression (FIG. 2D).

C. AsCYP51H10 is Synonymous with Sad2.

The above data are suggestive of a role for AsCYP51H10 in avenacin biosynthesis. We therefore sequenced the AsCyp51H10 gene in our original collection of ten sad mutants (5) to establish whether this gene was likely to correspond to any of the loci that we had defined by mutation. As expected, we found no differences in the sequence of AsCyp51H10 in the two characterised sad1 mutants within the collection. The sequence of AsCyp51H10 in six other mutants (single mutants for each of the loci, Sad3-Sad8) was also unaffected. However, non-synonymous point mutations were found in the coding region of AsCyp51H10 in the two independent sad2 mutants within the collection (#791 and #1027) (Table 1). Preliminary experiments suggested that the sad2 mutants #791 and #1027 accumulate β-amyrin while mutants affected at other Sad loci do not (15). This was confirmed by quantitative GC/MS analysis (FIG. 3A; Table 1). These data are consistent with a block in a cytochrome P450-mediated step early in the pathway and suggest that AsCyp51H10 is synonymous with Sad2.

Figure 3:
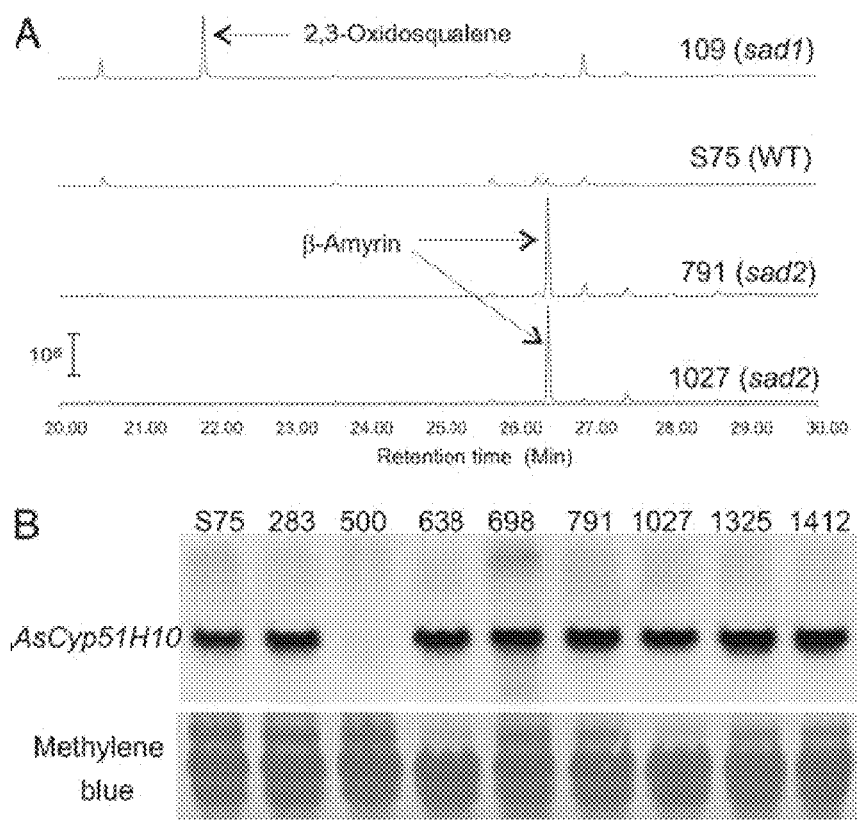
FIG. 3. Identification and characterisation of sad2 mutants. (A) GC analysis of root extracts from S75 (WT) and sad1 and sad2 mutants. The vertical bar on the bottom left indicates relative mass abundance. sad2 mutants accumulate β-amyrin, while sad1 mutants (such as mutant #109) accumulate 2,3-oxidosqualene. The identity of the accumulated intermediates was determined by MS. (B) Northern blot analysis of AsCyp51H10 transcript levels in sad2 mutants and the WT S75.

We then screened an extended collection of 92 reduced root fluorescence mutants with the objective of isolating more sad2 mutants, using TLC analysis as a preliminary screen. This allowed us to identify six new candidate sad2 mutants (#283, #500, #638, #698, #1325 and #1412). Allelism tests confirmed that these were indeed new mutant alleles of Sad2. Five of these new mutants had non-synonymous point mutations in the AsCyp51H10 gene, while the sixth mutant (#500) had a point mutation in an exon-intron boundary (Table 1). Significantly, AsCyp51H10 transcript levels were substantially reduced in mutant #500 (FIG. 3B). Quantitative GC/MS confirmed that, like #791 and #1027, these new sad2 mutants had elevated levels of β-amyrin (Table 1). These data provide compelling evidence that AsCyp51H10 corresponds to Sad2.

TABLE 1

| Characterization of sad2 mutants | | | | |
|---|---|---|---|---|
| Mutant | Mutation event | Predicted amino acid change | Region of protein | Mean β-amyrin content (μg/g of fresh roots) |
| Wild type | | | | |
| S75 | — | — | — | 1.4 ± 0.1 |

TABLE 1-continued

Characterization of sad2 mutants

| Mutant | Mutation event | Predicted amino acid change | Region of protein | Mean β-amyrin content (µg/g of fresh roots) |
|---|---|---|---|---|
| Original sad2 | | | | |
| 791 | $C^{2360} \rightarrow T$ | $Pro^{463} \rightarrow Ser$ | Near SRS6 | 40.2 ± 1.9 |
| 1027 | $C^{371} \rightarrow T$ | $Ala^{124} \rightarrow Val$ | SRS1 | 50.4 ± 1.2 |
| New sad2 | | | | |
| 283 | $G^{2277} \rightarrow A$ | $Gly^{435} \rightarrow Asp$ | Heme binding | 47.4 ± 8.5 |
| 500 | $G^{475} \rightarrow A$ | Splicing error | — | 41.3 ± 0.6 |
| 638 | $G^{1922} \rightarrow A$ | $Glu^{317} \rightarrow Lys$ | Conserved amino acid in αJ helix | 48.2 ± 2.9 |
| 698 | $G^{1670} \rightarrow A$ | $Ala^{233} \rightarrow Thr$ | SRS3 | ND |
| 1325 | $C^{1866} \rightarrow T$ | $Ser^{298} \rightarrow Phe$ | SRS4 | 37.1 ± 1.1 |
| 1412 | $C^{338} \rightarrow T$ | $Thr^{113} \rightarrow Ile$ | SRS1 | 41.5 ± 1.3 |

SRSs, predicted substrate recognition sites (16).
ND, not determined.

D. AsCYP51H10 is a Divergent Member of the CYP51 Family.

Comparisons of the amino acid sequences of sterol 14α-demethylase (CYP51) sequences from diverse organisms indicates 34 conserved amino acid residues across bacteria, protozoa, fungi, animals and plants. Six of these residues are not conserved in the oat AsCYP51H10 protein (FIG. 5). The predicted amino acid changes in the seven sad2 mutants with normal levels of AsCYP51H10 transcript were all within conserved substrate recognition sites or in other regions that are likely to be critical for structure and/or activity (Table 1). An alignment of selected regions of 36 representative CYP51 amino acid sequences across substrate recognition sites 1, 4, 5 and 6 (16) is shown in FIG. 4A. Modelling of the 3D structures of AsCYP51H10 and the oat sterol 14α-demethylase AsCYP51G1 using the *Mycobacterium tuberculosis* MtCYP51B1 crystal structure (16) as a template predicted the shapes and sizes of the active site cavities of MtCYP51B1 and AsCYP51G1 to be very similar while that of AsCYP51H10 is quite different (FIG. 4B). Residues that are predicted to significantly affect the size and shape of the active site cavity are shown in FIG. 4B. The ensemble-averaged active site volume in the model of AsCYP51H10 is 568±96 Å$^3$ while that of AsCYP51G1 is 346±108 Å$^3$, very similar to the active site volume determined from the crystal structure of MtCYP51B1 (343±62 Å$^3$). These observations are consistent with acquisition of a new function by AsCYP51H10.

FIG. 4C shows conserved subfamilies of CYP51 sterol 14α-demethylases from animals (CYP51A), bacteria (CYP51B), protozoa (CYP51E), fungi (CYP51F) and plants (CYP51G). AsCyp51G1, the predicted obtusifoliol 14α-demethylase from oat, falls within the CYP51G (dark green) subfamily. Yeast expression experiments have confirmed that this gene does indeed encode functional obtusifoliol 14α-demethylase (data not shown). However, we were unable to express AsCYP51H10 and AsCYP51H11 in active form with the standard yeast expression system used for conserved plant CYP51G enzymes (17). The CYP51H subfamily appears to be restricted to oats and rice and is not represented in *Arabidopsis*.

The position of *Chlamydomonas reinhardtii* CYP51G (CrCYP51G1) in the phylogenetic tree (FIG. 4C) implies that the CYP51H family was derived from an ancient CYP51G-like sequence during the evolution of green plants. Tajima's relative rate test (18) using *C. reinhardtii* CYP51G as an outgroup indicates that the AsCYP51H10 and AsCYP51H11 branches are significantly longer than that of AsCYP51G1 ($\chi 2=39.68$ and 41.67, respectively, P<0.0001). The branches of the rice sequences within the CYP51H subgroup are also significantly longer than that of rice CYP51G1 (data not shown). There is greater mean diversity in the rice and oat CYP51H subfamily than in the monocot CYP51G subfamily (0.653±0.028 versus 0.088±0.009, respectively). Collectively these results indicate that the CYP51H subfamily is evolving at a much higher rate than the conserved CYP51G subfamily, consistent with acquisition of a new function(s), as suggested by Nelson et al. (11). Our data confirm that AsCYP51H10 has indeed acquired a new function—in the synthesis of secondary metabolites required for plant defence. This finding has broad significance for understanding the mechanisms of action and potential evolutionary plasticity of the CYP51 family as a whole.

E. Co-Evolution of Sad1 and Sad2.

Previously we reported that Sad1 has arisen by duplication and divergence of a cycloartenol synthase-like gene (6, 8). The data presented here indicate that a second gene in the avenacin pathway, Sad2 (AsCyp51H10), has been recruited from an ancient CYP51G-like sequence. These results indicate an intimate evolutionary connection between sterol and triterpene biosynthesis. The first step in the pathway for the synthesis of a different group of defence-related compounds produced by maize (benzoxazinoids) has also been shown to be recruited from primary metabolism, in this case from tryptophan biosynthesis (19,20), and there is an increasing body of evidence to indicate that gene duplication, neofunctionalisation and positive selection drive metabolic diversification in plants (e.g. 21,22). Unlike their sterol pathway counterparts ASCS1 (cycloartenol synthase) and AsCyp51G1 (obtusifoliol 14α-demethylase), which are expressed throughout the plant, expression of Sad1 and Sad2 is highly tissue specific and is restricted to the epidermal cells of the root tips. AsCS1 and AsCyp51G1 are not genetically linked to each other or to the Sad gene cluster. Sad1 and Sad2 are physically linked and co-segregate with other genetically defined loci in the pathway that are required for clearly distinct biochemical functions (6). The biochemical function of AsCYP51H10 is as yet known. Conversion of β-amyrin to avenacin A-1 will require oxidation at five different sites (FIG. 1) and all of these conversions could potentially involve cytochrome P450 enzymes. AsCYP51H10 may therefore be required for hydroxylation of β-amyrin (or a modified derivative of this) at one or more positions. Elucidation of the precise biochemical function of AsCYP51H10, coupled with further investigation of the nature and origin of the avenacin gene cluster, will shed light on mechanisms underpinning the evolution of metabolic diversity in plants and on the selective pressures that drive this process.

With respect to the two promoters identified herein, we show that heterologous expression can be directed to the plant root tip by operatively linking these promoters to heterologous gene sequences. Likewise, utilizing these promoters to drive expression of the oat avenacin biosynthetic genes, heterologous expression in other plants (monocots and dicots) including in cereals (barley, wheat, rice, etc) other than oats is enabled to control soil borne diseases such as "take-all", *Fusarium*, and other root-infecting pathogens. There is as yet no effective form of take-all resistance in wheat germplasm, a resistance which has been demonstrated in oat due to the unique expression in this plant crop of the avenacins. Likewise, resistance to *Fusarium* and other root-infecting pathogens is an as yet not fully met need. We show that these promoters (Sad1, the gene encoding α-amyrin synthase, the first committed enzyme in the pathway, and Sad2, which encodes a CYP450 that also acts early in the pathway) retain their characteristic expression patterns when introduced into *Arabidopsis* and rice. These promoters therefore have broad utility across diverse plant species for targeted gene expression in roots. Our data indicate substantial sequence divergence of the pathway components that have been characterized to date since the separation of oats from other cereals in evolutionary time. Although the pathway is missing from closely related cereals, and yet precisely because they are closely related, one could reasonably expect the pathway to function in other cereals upon introduction of the pathway into such commercially valuable crops and other plants as necessary.

EXAMPLES

Having generally described this invention, the following exemplary support is provided to extend the written description an enable those skilled in the art to fully practice this invention. However, the specifics of these examples should not be read as limiting on the invention. Rather, for purposes of apprehending the scope of the invention disclosed herein, reference should be had to the appended claims.

Example 1

AsCyp51H10, AsCyp51H11 and AsCyp51G1 cDNA and Gene Isolation

Plant material. Wild type and mutant *Avena strigosa* lines are as described previously (5) Full-length cDNAs were defined by 5' and 3' RACE using GeneRacer™ kit (Invitrogen), amplified by PCR and cloned into the pCR®4-TOPO plasmid (Invitrogen). Genes were characterised by direct sequencing of PCR products generated from genomic DNA and/or by sequencing of BAC clones (see below).

BAC library construction and screening. A BAC library of *A. strigosa* accession number S75 was constructed using established methods (23). Approximately 150,000 colonies with an average insert size of ~110 Kb (ca. 4.2× genome coverage) were stored in 384-well microtitre plates and gridded onto high density filters. Filters were screened with $^{32}$P-labeled cDNA probes. Hybridisation and washing were conducted at stringencies of either 60° C. or 65° C. following standard methods (24). BAC fingerprinting was conducted by digestion of BAC DNA with HindIII and BamH1, and manual comparison of the restriction fragments after agarose gel electrophoresis. Subcloning of BAC inserts and sequencing was carried out using standard methods (24).

Transcript analysis. For Northern blot analysis, total RNA was extracted using TRI-REAGENT (Sigma). Hybridisations with biotin-labeled (Biotin-16-dUTP; Roche) antisense RNA probes for AsCyp51H10 were carried out at high stringency (68° C.) with signal detection using BrightStar® BioDetect™ (Ambion). For RT-PCR, first-strand cDNA synthesis was carried out using the SuperScript™ II Reverse Transcriptase (Invitrogen) according to the manufacturer's instructions and cDNA amplified by standard PCR with 30 cycles. For mRNA in situ analysis, biotin-labeled sense and antisense RNA probes from AsbAS1 and AsCyp51H10 were used. Tissue preparation and hybridisation was carried out as described (25).

Metabolite analysis. Roots from individual 6 day-old seedlings were harvested, freeze-dried, ground in liquid nitrogen and extracted with methanol. Extracts were centrifuged and the supernatant removed and dried down prior to extraction with 100 μl $CHCl_3$/MeOH (7:3 v/v). Extracts and a β-amyrin standard were spotted onto silica gel 60 thin layer chromatography (TLC) plates (Merk) and the TLC developed with hexane:acetone (80:20 v/v). β-Amyrin and other compounds were detected with iodine vapour. Qualitative and quantitative GC/MS was conducted using an Agilent 5973 Electron Ionisation mass selective detector coupled to an Agilent 6890 gas chromatograph. Trimethylsilyl (TMS) derivatives of the extracted samples were separated on a J&W DB-5MS capillary column (30 m long, 0.25 mm i.d., 0.25 μm film thickness; Agilent). The GC oven temperature was maintained at 250° C. for 1 min after injection, then programmed to 325° C. at a rate of 5°/min and held for 10 min at the final temperature. Helium carrier gas was used at a flow of 1.0 mL/min and 2 μL samples were injected in hexane in split mode (10:1) at an injector temperature of 250° C. The mass spectrometer ion source was maintained at 250° C. β-Amyrin was supplied by Apin Chemicals Ltd, and 2,3-oxidosqualene and 5β-cholestan-3β-ol standards by Sigma-Aldrich Co.

Sequence comparisons and homology modelling. Protein sequences (Supporting Table 2) were aligned using CLUSTER X, Version 1.8, manually adjusted according to Lepesheva et al (26) and displayed using ESPript (version 2.1)(27). MEGA3.1 software (28) was used for phylogenetic analysis, assessment of sequence diversity and Tajima's relative rate test (18). Gaps in the alignment were excluded from our analysis (complete-deletion option). The Neighbour-Joining method was used to construct the phylogenetic tree.

For homology modelling, sequence alignments of AsCYP51H10 and AsCYP51G1 with MtCYP51B1 utilised the structural information available in the PDB entry 1 EA1 and were generated using Fugue (29). Modeller (version 8.2) (30) was employed to generate homology models of the two enzymes based on the MtCYP51B1 crystal structure. The models were subjected to stereochemical validation using appropriate routines in Modeller (30). To explore more fully alternative active site residue conformations in our models other than those delivered directly by Modeller we used the non-Newtonian ensemble generator CONCOORD (31). The pocket definitions included residues 72-85, 95-103, 253-263, 319-324 and 433-435 in MtCYP51B1. Similar residues were included in simulations of AsCYP51H10 and AsCYP51G1. This approach allows prediction of the range of likely configurations adopted by the residues of the substrate-binding pocket. An energy-based method (QsiteFinder) was then used to characterise the active site cavities in the ensembles of modelled structures (32).

Example 2

Transformation and Expression of Promoter Regions of Oat Beta-amyrin Synthase (Sad1) and AsCyp51H10 (Sad2) in Both Rice and Arabidopsis Based on prior work in which an 1848 bp of 5' sequence for AsbAS1 (Sad1) was obtained, we made a deletion series (see FIG. 6) fused to GUS in pB1121 binary vector background (KmR). Constructs were stably transformed into *Arabidopsis thaliana* Landsberg erecta, utilizing the 35 S CMV promoter as a positive control and no promoter as a negative control. With this series, Gus activity was only observed in flowers and siliques (not in the roots). We did note that the pattern of expression changed within the deletion series.

We then obtained more upstream sequence and promoter fusion constructs were made with 3001 bp oat beta-amyrin synthase (Sad1) promoter and 3340 bp oat AsCYP51H10 (Sad2) (FIG. 7) promoter fused to both GUS and GFP reporter genes in the vector PHGWSF7. A third construct was made with the constitutively expressed ubiquitin promoter from maize in the same vector. All three constructs along with the promoterless vector were then stably transformed into *Arabidopsis* (accession Colombia) and rice (Nipponbare) by dipping plants in *Agrobacterium* solution for 2 mins, covering with a plastic bag to retain humidity for 24 hrs, removing the plastic bag, and harvesting the seed when ready. T1 seed was germinated on GM+Hyg50. We obtained the following numbers of HygR transformants from the first transformation attempt: 3 HygR transformants with the beta-amyrin synthase (Sad1) promoter, 1 HygR with AsCYP51H10 promoter, 2 HygR with Ubi promoter. We did not observe any GFP expression with any of isolates. We selected 3 HygR progeny from each of these plants for growing on for seed and we stained the remaining seedlings for GUS activity.

Our rice transformation methodology is shown graphically in FIG. 8. We germinated 40 seed from each T1 line on MSR6+50 ug/ml, Hygromycin, and checked for any signs of GFP expression. Our results are summarized as follows:

| Promoter | # Families | # died | # Sterile | #GFP | # Not Screened |
|---|---|---|---|---|---|
| Sad1 | 15 | 1 | 0 | 5 | 2 |
| AsCYP51H10 | 15 | 0 | 9 | 2 | 0 |
| Ubiquitin | 10 | 1 | 1 | 6 | 0 |
| None | 11 | 0 | 4 | 0 | 0 |

We then transferred x3 HygR +GFP expressing from each T1 family to CER for T2 seed. We found that expression of the Sad1 promoter in *Arabidopsis* and rice (as assessed using a GUS reporter) mirrors the distribution of the UV-fluorescent avenacins (and Sad1 expression) in oats (see from Turner, J., 1959, *J. Exp. Botany* 11:403-412.)

For *Arabidopsis* three transformed lines with the beta amyrin synthase promoter, one with the CypA promoter and two with the Ubi promoter have been analysed for Gus and GFP expression. No GFP expression was observed with any of the lines when examined under a stereo microscope.

When stained for Gus expression a clear pattern of expression was observed. In both the Bas (Sad1) and CypA (AsCYP51H10 gene (Sad2)) lines, gus expression was localised in the root tips and emerging laterals with very little/no expression in the leaves. For the ubiquitin constructs, extensive expression was observed in both the leaves and roots.

For rice, 9 transformed lines with the Bas promoter, 3 with the CypA, 7 with Ubiquitin and 11 with the promoterless vector have been analysed so far. For the Bas lines all expressed Gus in the root tips and emerging lateral roots in young seedlings. Expression was also seen in the leaf nodes (meristems) in some cases in older seedlings.

For CypA strong expression was seen in the root tips. Expression in the shoot meristems has not been investigated yet. For ubiquitin extensive expression was observed in both the roots and shoots.

No expression was seen in the promoterless control lines.

The disclosure of all references cited herein, inasmuch as it may be used by those skilled in the art to carry out the invention, is hereby specifically incorporated herein by cross-reference.

REFERENCES

1. Dixon R A (2001) *Nature* 411:843-847.
2. Field B, Jordán F, Osbourn A (2006) *New Phytologist*, in press.
3. Pichersky E, Gang D R (2000) *Trends Plant Sci* 5:439-445.
4. Hostettmann V, Marston A (1995) *Saponins* (Cambridge Univ Press, Cambridge, UK).
5. Papadopoulou K, Melton R E, Leggett M, Daniels M J, Osbourn A E (1999) *Proc Natl Acad Sci USA* 96:12923-12928.
6. Qi X, Bakht S, Leggett M, Maxwell C, Melton R, Osbourn A (2004) *Proc Natl Acad Sci USA* 101:8233-8238.
7. Chappell J (2002) *Curr Opin Plant Biol* 5:151-157.
8. Haralampidis K, Bryan G, Qi X, Papadopoulou K, Bakht S, Melton R, Osbourn A (2001) *Proc Natl Acad Sci USA* 98:13431-13436.
9. Haralampidis K, Trojanowska M, Osbourn A E (2002) *Adv Biochem Eng Biotechnol* 75:31-49.
10. Aoyama Y, Noshiro M, Gotoh O, Imaoka S, Funae Y, Kurosawa N, Horiuchi T, Yoshida Y (1996) *J Biochem* 119:926-933.
11. Nelson D R, Schuler M A, Paquette S M, Werck-Reichhart D, Bak S (2004) *Plant Physiol* 135: 756-772.
12. Aoyama Y (2005) *Front Biosci* 10:1546-1557.
13. Waterman R, Lepesheva G I (2005) *Biochem Biophys Res Commun* 338: 418-422.
14. Cabello-Hurtado F, Zimmerlin A, Rahier A, Taton M, DeRose R, Nedelkina S, Batard Y, Durst F, Pallett K E, Werck-Reichhart D (1997) *Biochem Biophys Res Commun* 230:381-385.
15. Trojanowska M R, Osbourn A E, Daniels M J, Threlfall D R (2001) *Phytochemistry* 56:121-129.
16. Podust L M, Poulos T L, Waterman M R (2001) *Proc Nat Acad Sci USA* 98:3068-3073.
17. Cabello-Hurtado F, Taton M, Forthoffer N, Kahn R, Bak S, Rahier A, Werck-Reichhart, D. (1999) *Eur J Biochem* 262:435-446.
18. Tajima F (1993) *Genetics* 135:599-607.
19. Gierl A, Frey M (2001) *Planta* 213:493-498.
20. Osbourn A E, Qi X, Townsend B, Qin, B (2003) *New Phytologist* 159: 101-108.
21. Hartmann T, Kutchan T M, Strack D (2005) *Phytochemistry* 1198-1199.
22. Benderoth M, Textor S, Windsor A J, Mitchell-Olds T, Gershenzon J, Kroymann J (2006) *Proc Natl Acad Sci USA* 103:9118-9123.
23. Allouis S, Moore G, Bellec A, Sharp R, Faivre Rampant P, Mortimer K, Pateyron S, Foote T N, Griffiths S, Caboche M, Chalhoub B (2003) *Cereal Res Commun* 31:331-338.

24. Sambrook J, Russell D W (2001) *Molecular Cloning: A Laboratory Manual*. (Cold Spring Harbour Lab. Press, NY, 3rd Ed).
25. Mao G, Buschmann H, Doonan J H, Lloyd C W (2006) *J Cell Sci* 119:753-758.
26. Lepesheva G I, Virus C, Waterman M R (2003) *Biochemistry* 42:9091-9101.
27. Gouet P, Courcelle E, Stuart D I, Metoz F (1999) *Bioinformatics* 15:305-308.
28. Kumar S, Tamura K, Nei M (2004) *Brief Bioinform* 5:150-163.
29. Shi J, Blundell T L, Mizuguchi K (2001) *J Mol Biol* 310:243-257.
30. Marti-Renom M A, Stuart A C, Fiser A, Sanchez R, Melo F, Sali A (2000) *Annu Rev Biophys Biomol Struct* 29:291-325.
31. de Groot B L (1997) *Proteins* 29:240-251.
32. Laurie A T, Jackson R M (2005) *Bioinformatics* 21:1908-1916.

The invention claimed is:

1. An isolated nucleic acid, comprising a root-specific promoter sequence selected from the group consisting of:
   (i) a polynucleotide comprising SEQ ID NO: 182;
   (ii) a variant of the polynucleotide of (i), sharing at least 98% identity with SEQ ID NO: 182, and capable of directing root-specific expression of an operably linked heterologous nucleotide sequence; and
   (iii) a portion of the polynucleotide of (i), the portion being capable of directing root-specific expression of an operably linked heterologous nucleotide sequence.

2. The nucleic acid as claimed in claim 1, wherein the root-specific promoter sequence comprises a fragment of at least at 500, 600, 700, 800, 900, or 1000 contiguous nucleotides of the sequence of nucleotides shown as 1 to 1057 in SEQ ID NO: 182, wherein the fragment is capable of directing root-specific expression of an operably linked heterologous nucleotide sequence.

3. The nucleic acid as claimed in claim 1, wherein the root-specific promoter sequence is formed by way of nucleotide addition, insertion, deletion or substitution.

4. An isolated nucleic acid comprising SEQ ID NO: 182.

5. An isolated polynucleotide comprising a nucleotide sequence which is the complement of the nucleic acid of any one of the preceding claims.

6. The nucleic acid as claimed in claim 1, wherein the promoter is operably linked to a heterologous nucleotide sequence it is desired to transcribe.

7. The nucleic acid as claimed in claim 6, wherein the heterologous nucleotide sequence is selected from a biosynthetic gene associated with pathogen resistance and a gene related to root nodule formation.

8. A recombinant vector which comprises the nucleic acid of claim 6.

9. The recombinant vector as claimed in claim 8 which is a plant vector.

10. A method comprising introducing the vector of claim 9 into a host cell.

11. A host cell containing or transformed with the vector of claim 9.

12. A method for producing a transgenic plant, the method comprising the steps of:
   (a) introducing the vector of claim 9 into a plant cell, and
   (b) regenerating a transgenic plant from the plant cell.

13. A transgenic plant:
   a) obtained by the method of claim 12; or
   b) a clone, or selfed or hybrid progeny or other descendant of said transgenic plant of (a), which in each case includes the nucleic acid.

14. A method for directing root-specific expression of a nucleotide sequence it is desired to transcribe, said method comprising introducing into a plant cell the nucleic acid of claim 6, and regenerating a plant from said plant cell in order to effect said specific expression.

15. The method as claimed in claim 14 wherein the root-specific expression is at the root-tip and lateral root initials.

16. A method of expressing a polypeptide from a nucleotide sequence it is desired to transcribe the method comprising the step of exposing a plant cell comprising the nucleic acid of claim 6 to conditions effective to cause or allow expression of the polypeptide in the plant cell.

17. The method as claimed in claim 16 wherein the plant cell is a root cell.

18. The method as claimed in claim 16 wherein the the nucleic acid is present in a vector.

19. The method of claim 16, wherein the polypeptide is expressed in a plant and results in modified root nodule development.

20. The method of claim 16, wherein the polypeptide is expressed in a plant and results in increased pathogen resistance against a soil borne disease pathogen.

21. The method as claimed in claim 14 wherein the plant is a cereal plant.

22. The method as claimed in claim 14 wherein the plant is not oat.

23. An isolated nucleic acid comprising a sequence from position 1 to position 1057 of SEQ ID NO: 182, the sequence having root-specific promoter activity.

24. A recombinant vector comprising the nucleic acid of claim 23.

25. The plant of claim 13, wherein the nucleic acid is integrated into the genome of the plant cell.

26. A transgenic plant comprising a plant vector comprising the nucleic acid of claim 1 operably linked to a heterologous nucleic acid sequence or progeny or other descendant of said transgenic plant which, in each case comprises the nucleic acid of claim 1 operably linked to the heterologous nucleic acid sequence.

27. The method of claim 10, further comprising causing or allowing recombination between the vector and the host cell genome thereby transforming the host cell with the nucleic acid.

28. The method of claim 19, wherein the modified nodule development results in enhanced nitrogen fixation capability.

* * * * *

SEQUENCE LISTING

```
<160> NUMBER OF SEQ ID NOS: 186

<210> SEQ ID NO 1
<211> LENGTH: 22
<212> TYPE: PRT
<213> ORGANISM: Mycobacterium tuberculosis

<400> SEQUENCE: 1

Ala Tyr Pro Phe Met Thr Pro Ile Phe Gly Glu Gly Val Val Phe Asp
1               5                   10                  15

Ala Ser Pro Glu Arg Arg
            20

<210> SEQ ID NO 2
<211> LENGTH: 13
<212> TYPE: PRT
<213> ORGANISM: Mycobacterium tuberculosis

<400> SEQUENCE: 2

Phe Ala Gly His His Thr Ser Ser Gly Thr Ala Ser Trp
1               5                   10

<210> SEQ ID NO 3
<211> LENGTH: 11
<212> TYPE: PRT
<213> ORGANISM: Mycobacterium tuberculosis

<400> SEQUENCE: 3

His Pro Pro Leu Ile Ile Leu Met Arg Val Ala
1               5                   10

<210> SEQ ID NO 4
<211> LENGTH: 11
<212> TYPE: PRT
<213> ORGANISM: Mycobacterium tuberculosis

<400> SEQUENCE: 4

His Ser Lys Met Val Val Gln Leu Ala Gln Pro
1               5                   10

<210> SEQ ID NO 5
<211> LENGTH: 22
<212> TYPE: PRT
<213> ORGANISM: Mycobacterium avium

<400> SEQUENCE: 5

Ala Tyr Pro Phe Met Thr Pro Ile Phe Gly Lys Gly Val Val Phe Asp
1               5                   10                  15

Ala Ser Pro Glu Arg Arg
            20

<210> SEQ ID NO 6
```

```
<211> LENGTH: 13
<212> TYPE: PRT
<213> ORGANISM: Mycobacterium avium

<400> SEQUENCE: 6

Phe Ala Gly His His Thr Ser Ser Gly Thr Ser Ala Trp
1               5                   10

<210> SEQ ID NO 7
<211> LENGTH: 11
<212> TYPE: PRT
<213> ORGANISM: Mycobacterium avium

<400> SEQUENCE: 7

His Pro Pro Leu Ile Ile Leu Met Arg Val Ala
1               5                   10

<210> SEQ ID NO 8
<211> LENGTH: 11
<212> TYPE: PRT
<213> ORGANISM: Mycobacterium avium

<400> SEQUENCE: 8

His Ser Lys Met Val Val G

```
<211> LENGTH: 22
<212> TYPE: PRT
<213> ORGANISM: Trypanosoma brucei

<400> SEQUENCE: 13

Val Tyr Ser Phe Met Glu Pro Val Phe Gly Glu Gly Val Ala Tyr Ala
1               5                   10                  15

Ala Pro Tyr Pro Arg Met
            20

<210> SEQ ID NO 14
<211> LENGTH: 13
<212> TYPE: PRT
<213> ORGANISM: Trypanosoma brucei

<400> SEQUENCE: 14

Phe Ala Gly Gln His Thr Ser Ser Ile Thr Thr Thr Trp
1               5                   10

<210> SEQ ID NO 15
<211> LENGTH: 11
<212> TYPE: PRT
<213> ORGANISM: Trypanosoma brucei

<400> SEQUENCE: 15

Asp Pro Pro Leu Leu Met Leu Met Arg Lys Val
1               5                   10

<210> SEQ ID NO 16
<211> LENGTH: 11
<212> TYPE: PRT
<213> ORGANISM: Trypanosoma brucei

<400> SEQUENCE: 16

Tyr His Thr Met Val Val Gly Pro Thr Ala Ser
1               5                   10

<210> SEQ ID NO 17
<211> LENGTH: 22
<212> TYPE: PRT
<213> ORGANISM: Trypanosoma cruzi

<400> SEQUENCE: 17

Val Tyr Thr Ile Met Thr Pro Val Phe Gly Glu Gly Val Ala Tyr Ala
1               5                   10                  15

Ala Pro Tyr Pro Arg Met
            20

<210> SEQ ID NO 18
<211> LENGTH: 13
<212> TYPE: PRT
<213> ORGANISM: Trypanosoma cruzi

<400> SEQUENCE: 18

Phe Ala Gly Gln His Thr Ser Thr Ile Thr Thr Ser Trp
1               5                   10

<210> SEQ ID NO 19
<211> LENGTH: 11
<212> TYPE: PRT
<213> ORGANISM: Trypanosoma cruzi

<400> SEQUENCE: 19

Asp Pro Pro Leu Leu Met Val Met Arg Met Val
1               5                   10
```

```
<210> SEQ ID NO 20
<211> LENGTH: 11
<212> TYPE: PRT
<213> ORGANISM: Trypanosoma cruzi

<400> SEQUENCE: 20

Tyr His Thr Met Val Val Gly Pro Thr Leu Asn
1               5                   10

<210> SEQ ID NO 21
<211> LENGTH: 22
<212> TYPE: PRT
<213> ORGANISM: Leishmania major

<400> SEQUENCE: 21

Val Tyr Ser Phe Met Val Pro Val Phe Gly Glu Gly Val Ala Tyr Ala
1               5                   10                  15

Ala Pro Tyr Pro Arg Met
            20

<210> SEQ ID NO 22
<211> LENGTH: 13
<212> TYPE: PRT
<213> ORGANISM: Leishmania major

<400> SEQUENCE: 22

Phe Ala Gly Gln His Thr Ser Thr Ile Thr Thr Thr Trp
1               5                   10

<210> SEQ ID NO 23
<211> LENGTH: 11
<212> TYPE: PRT
<213> ORGANISM: Leishmania major

<400> SEQUENCE: 23

Asp Pro Pro Leu Ile Met Leu Met Arg Lys Val
1               5                   10

<210> SEQ ID NO 24
<211> LENGTH: 11
<212> TYPE: PRT
<213> ORGANISM: Leishmania major

<400> SEQUENCE: 24

Tyr His Thr Met Val Val Gly Pro Thr Ala Ser
1               5                   10

<210> SEQ ID NO 25
<211> LENGTH: 23
<212> TYPE: PRT
<213> ORGANISM: Abudefduf saxatilis

<400> SEQUENCE: 25

Val Tyr Ser Arg Leu Thr Thr Pro Val Phe Gly Lys Gly Val Ala Tyr
1               5                   10                  15

Asp Val Pro Asn Pro Ile Phe
            20

<210> SEQ ID NO 26
<211> LENGTH: 13
<212> TYPE: PRT
<213> ORGANISM: Abudefduf saxatilis

<400> SEQUENCE: 26
```

Leu Ala Gly Gln His Thr Ser Ser Thr Thr Ser Ala Trp
1               5                   10

<210> SEQ ID NO 27
<211> LENGTH: 11
<212> TYPE: PRT
<213> ORGANISM: Abudefduf saxatilis

<400> SEQUENCE: 27

Arg Pro Pro Ile Met Thr Met Met Arg Met Ala
1               5                   10

<210> SEQ ID NO 28
<211> LENGTH: 11
<212> TYPE: PRT
<213> ORGANISM: Abudefduf saxatilis

<400> SEQUENCE: 28

Tyr Thr Thr Met Ile His Thr Pro His Asn Pro
1               5                   10

<210> SEQ ID NO 29
<211> LENGTH: 23
<212> TYPE: PRT
<213> ORGANISM: Fundulus heteroclitus

<400> SEQUENCE: 29

Val Tyr Ser Lys Leu Thr Thr Pro Val Phe Gly Lys Gly Val Ala Tyr
1               5                   10                  15

Asp Val Pro Asn Pro Ile Phe
            20

<210> SEQ ID NO 30
<211> LENGTH: 13
<212> TYPE: PRT
<213> ORGANISM: Fundulus heteroclitus

<400> SEQUENCE: 30

Leu Ala Gly Gln His Thr Ser Ser Thr Thr Ser Ala Trp
1               5                   10

<210> SEQ ID NO 31
<211> LENGTH: 11
<212> TYPE: PRT
<213> ORGANISM: Fundulus heteroclitus

<400> SEQUENCE: 31

Arg Pro Pro Ile Met Thr Met Met Arg Met Ala
1               5                   10

<210> SEQ ID NO 32
<211> LENGTH: 11
<212> TYPE: PRT
<213> ORGANISM: Fundulus heteroclitus

<400> SEQUENCE: 32

Tyr Thr Thr Met Ile His Thr Pro His Asn Pro
1               5                   10

<210> SEQ ID NO 33
<211> LENGTH: 23
<212> TYPE: PRT
<213> ORGANISM: Danio rerio

<400> SEQUENCE: 33

```
Val Tyr Ala Arg Leu Thr Thr Pro Val Phe Gly Lys Gly Val Ala Tyr
1               5                   10                  15

Asp Val Pro Asn Pro Leu Phe
                20
```

<210> SEQ ID NO 34
<211> LENGTH: 13
<212> TYPE: PRT
<213> ORGANISM: Danio rerio

<400> SEQUENCE: 34

```
Leu Ala Gly Gln His Thr Ser Ser Thr Thr Ser Ala Trp
1               5                   10
```

<210> SEQ ID NO 35
<211> LENGTH: 11
<212> TYPE: PRT
<213> ORGANISM: Danio rerio

<400> SEQUENCE: 35

```
Arg Pro Pro Ile Met Thr Met Met Arg Met Ala
1               5                   10
```

<210> SEQ ID NO 36
<211> LENGTH: 11
<212> TYPE: PRT
<213> ORGANISM: Danio rerio

<400> SEQUENCE: 36

```
Tyr Thr Thr Met Ile His Thr Pro His Asn Pro
1               5                   10
```

<210> SEQ ID NO 37
<211> LENGTH: 10
<212> TYPE: PRT
<213> ORGANISM: Homo sapiens

<400> SEQUENCE: 37

```
Val Tyr Ser Arg Leu Thr Thr Pro Val Phe
1               5                   10
```

<210> SEQ ID NO 38
<211> LENGTH: 13
<212> TYPE: PRT
<213> ORGANISM: Homo sapiens

<400> SEQUENCE: 38

```
Leu Ala Gly Gln His Thr Ser Ser Thr Thr Ser Ala Trp
1               5                   10
```

<210> SEQ ID NO 39
<211> LENGTH: 11
<212> TYPE: PRT
<213> ORGANISM: Homo sapiens

<400> SEQUENCE: 39

```
Arg Pro Pro Ile Met Ile Met Met Arg Met Ala
1               5                   10
```

<210> SEQ ID NO 40
<211> LENGTH: 11
<212> TYPE: PRT
<213> ORGANISM: Homo sapiens

<400> SEQUENCE: 40

Tyr Thr Thr Met Ile His Thr Pro Glu Asn Pro
1               5                   10

<210> SEQ ID NO 41
<211> LENGTH: 23
<212> TYPE: PRT
<213> ORGANISM: Rattus sp.

<400> SEQUENCE: 41

Val Tyr Gly Arg Leu Thr Thr Pro Val Phe Gly Lys Gly Val Ala Tyr
1               5                   10                  15

Asp Val Pro Asn Ala Val Phe
            20

<210> SEQ ID NO 42
<211> LENGTH: 13
<212> TYPE: PRT
<213> ORGANISM: Rattus sp.

<400> SEQUENCE: 42

Leu Ala Gly Gln His Thr Ser Ser Thr Thr Ser Ala Trp
1               5                   10

<210> SEQ ID NO 43
<211> LENGTH: 11
<212> TYPE: PRT
<213> ORGANISM: Rattus sp.

<400> SEQUENCE: 43

Arg Pro Pro Ile Met Thr Met Met Arg Met Ala
1               5                   10

<210> SEQ ID NO 44
<211> LENGTH: 11
<212> TYPE: PRT
<213> ORGANISM: Rattus sp.

<400> SEQUENCE: 44

Tyr Thr Thr Met Ile His Thr Pro Glu Asn Pro
1               5                   10

<210> SEQ ID NO 45
<211> LENGTH: 23
<212> TYPE: PRT
<213> ORGANISM: Aspergillus fumigatus

<400> SEQUENCE: 45

Val Tyr Ser Pro Leu Thr Thr Pro Val Phe Gly Ser Asp Val Val Tyr
1               5                   10                  15

Asp Cys Pro Asn Ser Lys Leu
            20

<210> SEQ ID NO 46
<211> LENGTH: 13
<212> TYPE: PRT
<213> ORGANISM: Aspergillus fumigatus

<400> SEQUENCE: 46

Met Ala Gly Gln His Ser Ser Ser Ile Ser Ala Trp
1               5                   10

<210> SEQ ID NO 47
<211> LENGTH: 11
<212> TYPE: PRT

```
<213> ORGANISM: Aspergillus fumigatus

<400> SEQUENCE: 47

His Ser Ser Ile His Ser Ile Met Arg Lys Val
1               5                   10

<210> SEQ ID NO 48
<211> LENGTH: 11
<212> TYPE: PRT
<213> ORGANISM: Aspergillus fumigatus

<400> SEQUENCE: 48

Tyr Ser Ser Leu Phe Ser Gly Pro Met Lys Pro
1               5                   10

<210> SEQ ID NO 49
<211> LENGTH: 23
<212> TYPE: PRT
<213> ORGANISM: Penicillium digitatum

<400> SEQUENCE: 49

Ile Tyr Gly Lys Leu Thr Thr Pro Val Phe Gly Ser Asp Val Val Tyr
1               5                   10                  15

Asp Cys Pro Asn Ser Lys Leu
            20

<210> SEQ ID NO 50
<211> LENGTH: 13
<212> TYPE: PRT
<213> ORGANISM: Penicillium digitatum

<400> SEQUENCE: 50

Met Ala Gly Gln His Ser Ser Ala Ser Ile Ser Cys Trp
1               5                   10

<210> SEQ ID NO 51
<211> LENGTH: 11
<212> TYPE: PRT
<213> ORGANISM: Penicillium digitatum

<400> SEQUENCE: 51

His Ser Ser Ile His Thr Leu Met Arg Lys Val
1               5                   10

<210> SEQ ID NO 52
<211> LENGTH: 11
<212> TYPE: PRT
<213> ORGANISM: Penicillium digitatum

<400> SEQUENCE: 52

Tyr Ser Ser Leu Phe Ser Arg Pro Met Gln Pro
1               5                   10

<210> SEQ ID NO 53
<211> LENGTH: 23
<212> TYPE: PRT
<213> ORGANISM: Monilinia fructicola

<400> SEQUENCE: 53

Ile Tyr Thr Val Leu Thr Thr Pro Val Phe Gly Lys Asp Val Val Tyr
1               5                   10                  15

Asp Cys Pro Asn Ala Lys Leu
            20
```

-continued

```
<210> SEQ ID NO 54
<211> LENGTH: 13
<212> TYPE: PRT
<213> ORGANISM: Monilinia fructicola

<400> SEQUENCE: 54

Met Ala Gly Gln His Ser Ser Ser Ser Ser Ile Ser Trp
1               5                   10

<210> SEQ ID NO 55
<211> LENGTH: 11
<212> TYPE: PRT
<213> ORGANISM: Monilinia fructicola

<400> SEQUENCE: 55

His Thr Pro Ile His Ser Ile Met Arg Lys Val
1               5                   10

<210> SEQ ID NO 56
<211> LENGTH: 11
<212> TYPE: PRT
<213> ORGANISM: Monilinia fructicola

<400> SEQUENCE: 56

Tyr Thr Ser Leu Phe Thr Gly Pro Leu Glu Pro
1               5                   10

<210> SEQ ID NO 57
<211> LENGTH: 23
<212> TYPE: PRT
<213> ORGANISM: Uncinula necator

<400> SEQUENCE: 57

Ile Tyr Thr Asn Leu Thr Thr Pro Val Phe Gly Arg Asp Val Val Tyr
1               5                   10                  15

Asp Cys Pro Asn Ser Lys Leu
            20

<210> SEQ ID NO 58
<211> LENGTH: 13
<212> TYPE: PRT
<213> ORGANISM: Uncinula necator

<400> SEQUENCE: 58

Met Ala Gly Gln His Ser Ser Ser Ser Thr Ser Ser Trp
1               5                   10

<210> SEQ ID NO 59
<211> LENGTH: 11
<212> TYPE: PRT
<213> ORGANISM: Uncinula necator

<400> SEQUENCE: 59

His Ala Pro Ile His Ser Ile Met Arg Lys Val
1               5                   10

<210> SEQ ID NO 60
<211> LENGTH: 11
<212> TYPE: PRT
<213> ORGANISM: Uncinula necator

<400> SEQUENCE: 60

Tyr Ser Ser Leu Phe Ser Met Pro Leu Ala Pro
1               5                   10
```

```
<210> SEQ ID NO 61
<211> LENGTH: 23
<212> TYPE: PRT
<213> ORGANISM: Mycosphaerella graminicola

<400> SEQUENCE: 61

Ile Tyr Ser Pro Leu Thr Thr Pro Val Phe Gly Lys Asp Val Val Tyr
1               5                   10                  15

Asp Cys Pro Asn Ser Lys Leu
            20

<210> SEQ ID NO 62
<211> LENGTH: 13
<212> TYPE: PRT
<213> ORGANISM: Mycosphaerella graminicola

<400> SEQUENCE: 62

Met Ala Gly Gln His Ser Ser Ser Ala Thr Glu Ser Trp
1               5                   10

<210> SEQ ID NO 63
<211> LENGTH: 11
<212> TYPE: PRT
<213> ORGANISM: Mycosphaerella graminicola

<400> SEQUENCE: 63

His Ala Pro Ile His Ser Ile Leu Arg Lys Val
1               5                   10

<210> SEQ ID NO 64
<211> LENGTH: 11
<212> TYPE: PRT
<213> ORGANISM: Mycosphaerella graminicola

<400> SEQUENCE: 64

Tyr Ser Ser Leu Phe Ser Arg Pro Leu Ser Pro
1               5                   10

<210> SEQ ID NO 65
<211> LENGTH: 23
<212> TYPE: PRT
<213> ORGANISM: Venturia nashicola

<400> SEQUENCE: 65

Ile Tyr Ser Pro Leu Thr Thr Pro Val Phe Gly Ser Asp Val Val Tyr
1               5                   10                  15

Asp Cys Pro Asn Ser Lys Leu
            20

<210> SEQ ID NO 66
<211> LENGTH: 13
<212> TYPE: PRT
<213> ORGANISM: Venturia nashicola

<400> SEQUENCE: 66

Met Ala Gly Gln His Ser Ser Ser Ser Thr Ser Ser Trp
1               5                   10

<210> SEQ ID NO 67
<211> LENGTH: 11
<212> TYPE: PRT
<213> ORGANISM: Venturia nashicola

<400> SEQUENCE: 67

His Ser Pro Ile His Ser Ile Leu Arg Ala Val
```

```
1               5                   10

<210> SEQ ID NO 68
<211> LENGTH: 11
<212> TYPE: PRT
<213> ORGANISM: Venturia nashicola

<400> SEQUENCE: 68

Phe Ser Ser Leu Phe Ser Gly Pro Gln Arg Pro
1               5                   10

<210> SEQ ID NO 69
<211> LENGTH: 23
<212> TYPE: PRT
<213> ORGANISM: Schizosaccharomyces pombe

<400> SEQUENCE: 69

Ala Tyr Ser His Leu Thr Thr Pro Val Phe Gly Lys Asp Val Val Tyr
1               5                   10                  15

Asp Ile Pro Asn His Val Phe
            20

<210> SEQ ID NO 70
<211> LENGTH: 13
<212> TYPE: PRT
<213> ORGANISM: Schizosaccharomyces pombe

<400> SEQUENCE: 70

Met Ala Gly Gln His Thr Ser Ala Ala Thr Ile Val Trp
1               5                   10

<210> SEQ ID NO 71
<211> LENGTH: 10
<212> TYPE: PRT
<213> ORGANISM: Schizosaccharomyces pombe

<400> SEQUENCE: 71

His Pro Pro Ile His Ser His Met Arg Lys
1               5                   10

<210> SEQ ID NO 72
<211> LENGTH: 11
<212> TYPE: PRT
<213> ORGANISM: Schizosaccharomyces pombe

<400> SEQUENCE: 72

Tyr Ser Ser Met Val Ala Leu Pro Leu Gly Pro
1               5                   10

<210> SEQ ID NO 73
<211> LENGTH: 23
<212> TYPE: PRT
<213> ORGANISM: Candida albicans

<400> SEQUENCE: 73

Ala Tyr Lys His Leu Thr Thr Pro Val Phe Gly Lys Gly Val Ile Tyr
1               5                   10                  15

Asp Cys Pro Asn Ser Arg Leu
            20

<210> SEQ ID NO 74
<211> LENGTH: 13
<212> TYPE: PRT
<213> ORGANISM: Candida albicans
```

<400> SEQUENCE: 74

Met Gly Gly Gln His Thr Ser Ala Ser Thr Ser Ala Trp
1               5                   10

<210> SEQ ID NO 75
<211> LENGTH: 11
<212> TYPE: PRT
<213> ORGANISM: Candida albicans

<400> SEQUENCE: 75

His Met Pro Leu His Ser Ile Phe Arg Lys Val
1               5                   10

<210> SEQ ID NO 76
<211> LENGTH: 11
<212> TYPE: PRT
<213> ORGANISM: Candida albicans

<400> SEQUENCE: 76

Tyr Ser Ser Met Val Val Leu Pro Thr Glu Pro
1               5                   10

<210> SEQ ID NO 77
<211> LENGTH: 23
<212> TYPE: PRT
<213> ORGANISM: Candida glabrata

<400> SEQUENCE: 77

Ala Tyr Ser His Leu Thr Thr Pro Val Phe Gly Lys Gly Val Ile Tyr
1               5                   10                  15

Asp Cys Pro Asn His Arg Leu
                20

<210> SEQ ID NO 78
<211> LENGTH: 13
<212> TYPE: PRT
<213> ORGANISM: Candida glabrata

<400> SEQUENCE: 78

Met Gly Gly Gln His Thr Ser Ala Ala Thr Ser Ala Trp
1               5                   10

<210> SEQ ID NO 79
<211> LENGTH: 11
<212> TYPE: PRT
<213> ORGANISM: Candida glabrata

<400> SEQUENCE: 79

His His Pro Leu His Ser Leu Phe Arg Lys Val
1               5                   10

<210> SEQ ID NO 80
<211> LENGTH: 11
<212> TYPE: PRT
<213> ORGANISM: Candida glabrata

<400> SEQUENCE: 80

Phe Thr Ser Met Val Thr Leu Pro Thr Ala Pro
1               5                   10

<210> SEQ ID NO 81
<211> LENGTH: 23
<212> TYPE: PRT
<213> ORGANISM: Ashbya gossypii -continued

```
<400> SEQUENCE: 81

Ala Tyr Thr Lys Leu Thr Thr Pro Val Phe Gly Glu Gly Val Val Tyr
1               5                   10                  15

Asp Cys Pro Asn His Arg Leu
            20

<210> SEQ ID NO 82
<211> LENGTH: 13
<212> TYPE: PRT
<213> ORGANISM: Ashbya gossypii

<400> SEQUENCE: 82

Met Gly Gly Gln His Thr Ser Ala Ala Thr Ser Ala Trp
1               5                   10

<210> SEQ ID NO 83
<211> LENGTH: 11
<212> TYPE: PRT
<213> ORGANISM: Ashbya gossypii

<400> SEQUENCE: 83

His His Pro Leu His Ser Leu Phe Arg Lys Val
1               5                   10

<210> SEQ ID NO 84
<211> LENGTH: 11
<212> TYPE: PRT
<213> ORGANISM: Ashbya gossypii

<400> SEQUENCE: 84

Phe Thr Ser Met Val Thr Leu Pro Ser Glu Pro
1               5                   10

<210> SEQ ID NO 85
<211> LENGTH: 23
<212> TYPE: PRT
<213> ORGANISM: Filobasidiella neoformans

<400> SEQUENCE: 85

Ala Tyr Thr His Leu Thr Thr Pro Val Phe Gly Lys Gly Val Val Tyr
1               5                   10                  15

Asp Cys Pro Asn Glu Met Leu
            20

<210> SEQ ID NO 86
<211> LENGTH: 13
<212> TYPE: PRT
<213> ORGANISM: Filobasidiella neoformans

<400> SEQUENCE: 86

Met Ala Gly Gln His Thr Ser Ser Ala Thr Ser Ser Trp
1               5                   10

<210> SEQ ID NO 87
<211> LENGTH: 11
<212> TYPE: PRT
<213> ORGANISM: Filobasidiella neoformans

<400> SEQUENCE: 87

His Ala Pro Ile His Ser Ile Tyr Arg Lys Val
1               5                   10

<210> SEQ ID NO 88
<211> LENGTH: 11
```

```
<212> TYPE: PRT
<213> ORGANISM: Filobasidiella neoformans

<400> SEQUENCE: 88

Tyr Arg Thr Met Ile Val Gln Pro Asn Asn Pro
1               5                   10

<210> SEQ ID NO 89
<211> LENGTH: 23
<212> TYPE: PRT
<213> ORGANISM: Ustilago maydis

<400> SEQUENCE: 89

Ala Tyr Thr His Leu Thr Thr Pro Val Phe Gly Lys Glu Val Val Tyr
1               5                   10                  15

Asp Val Pro Asn Ala Val Phe
            20

<210> SEQ ID NO 90
<211> LENGTH: 13
<212> TYPE: PRT
<213> ORGANISM: Ustilago maydis

<400> SEQUENCE: 90

Met Ala Gly Gln His Thr Ser Ser Ala Thr Ser Ser Trp
1               5                   10

<210> SEQ ID NO 91
<211> LENGTH: 11
<212> TYPE: PRT
<213> ORGANISM: Ustilago maydis

<400> SEQUENCE: 91

His Pro Pro Leu His Ser Ile Met Arg Tyr Val
1               5                   10

<210> SEQ ID NO 92
<211> LENGTH: 11
<212> TYPE: PRT
<213> ORGANISM: Ustilago maydis

<400> SEQUENCE: 92

Tyr Gln Ser Met Val Val Leu Pro Ser Lys Asn
1               5                   10

<210> SEQ ID NO 93
<211> LENGTH: 22
<212> TYPE: PRT
<213> ORGANISM: Chlamydomonas reinhardtii

<400> SEQUENCE: 93

Val Tyr Asp Phe Asn Ile Pro Thr Phe Gly Arg Gly Val Val Phe Asp
1               5                   10                  15

Val Glu Gln Lys Val Arg
            20

<210> SEQ ID NO 94
<211> LENGTH: 13
<212> TYPE: PRT
<213> ORGANISM: Chlamydomonas reinhardtii

<400> SEQUENCE: 94

Phe Ala Gly Gln His Thr Ser Ser Ile Thr Thr Ser Trp
1               5                   10
```

-continued

```
<210> SEQ ID NO 95
<211> LENGTH: 11
<212> TYPE: PRT
<213> ORGANISM: Chlamydomonas reinhardtii

<400> SEQUENCE: 95

His Pro Pro Leu Leu Val Met Arg Tyr Ala
1               5                   10

<210> SEQ ID NO 96
<211> LENGTH: 11
<212> TYPE: PRT
<213> ORGANISM: Chlamydomonas reinhardtii

<400> SEQUENCE: 96

Tyr Glu Ser Met Val Ile Gly Pro Lys Pro Cys
1               5                   10

<210> SEQ ID NO 97
<211> LENGTH: 22
<212> TYPE: PRT
<213> ORGANISM: Lycopersicon esculentum

<400> SEQUENCE: 97

Val Tyr Gln Phe Asn Val Pro Thr Phe Gly Pro Gly Val Val Phe Asp
1               5                   10                  15

Val Asp Tyr Thr Ile Arg
            20

<210> SEQ ID NO 98
<211> LENGTH: 13
<212> TYPE: PRT
<213> ORGANISM: Lycopersicon esculentum

<400> SEQUENCE: 98

Phe Ala Gly Gln His Thr Ser Ser Ile Thr Ser Thr Trp
1               5                   10

<210> SEQ ID NO 99
<211> LENGTH: 11
<212> TYPE: PRT
<213> ORGANISM: Lycopersicon esculentum

<400> SEQUENCE: 99

His Pro Pro Leu Ile Met Leu Leu Arg Ser Ser
1               5                   10

<210> SEQ ID NO 100
<211> LENGTH: 11
<212> TYPE: PRT
<213> ORGANISM: Lycopersicon esculentum

<400> SEQUENCE: 100

Trp Asn Ala Met Val Val Gly Val Lys Gly Glu
1               5                   10

<210> SEQ ID NO 101
<211> LENGTH: 22
<212> TYPE: PRT
<213> ORGANISM: Populus sp.

<400> SEQUENCE: 101

Val Tyr Gln Phe Asn Val Pro Thr Phe Gly Pro Gly Val Val Phe Asp
1               5                   10                  15
```

Val Asp Tyr Ser Ile Arg
            20

<210> SEQ ID NO 102
<211> LENGTH: 13
<212> TYPE: PRT
<213> ORGANISM: Populus sp.

<400> SEQUENCE: 102

Phe Ala Gly Gln His Thr Ser Ser Ile Thr Ser Thr Trp
1               5                   10

<210> SEQ ID NO 103
<211> LENGTH: 11
<212> TYPE: PRT
<213> ORGANISM: Populus sp.

<400> SEQUENCE: 103

His Pro Pro Leu Ile Met Leu Leu Arg Ser Ser
1               5                   10

<210> SEQ ID NO 104
<211> LENGTH: 11
<212> TYPE: PRT
<213> ORGANISM: Populus sp.

<400> SEQUENCE: 104

Trp Asn Ala Met Val Val Gly Val Lys Asp Lys
1               5                   10

<210> SEQ ID NO 105
<211> LENGTH: 22
<212> TYPE: PRT
<213> ORGANISM: Aquilegia sp.

<400> SEQUENCE: 105

Val Tyr Gln Phe Asn Val Pro Thr Phe Gly Pro Gly Val Val Phe Asp
1               5                   10                  15

Val Asp Tyr Ser Val Arg
            20

<210> SEQ ID NO 106
<211> LENGTH: 13
<212> TYPE: PRT
<213> ORGANISM: Aquilegia sp.

<400> SEQUENCE: 106

Phe Ala Gly Gln His Thr Ser Ser Ile Thr Ser Thr Trp
1               5                   10

<210> SEQ ID NO 107
<211> LENGTH: 11
<212> TYPE: PRT
<213> ORGANISM: Aquilegia sp.

<400> SEQUENCE: 107

His Pro Pro Leu Ile Met Leu Leu Arg Ser Ser
1               5                   10

<210> SEQ ID NO 108
<211> LENGTH: 11
<212> TYPE: PRT
<213> ORGANISM: Aquilegia sp.

<400> SEQUENCE: 108

```
Trp Asn Ala Met Val Val Gly Val Lys Gly Lys
1               5                   10
```

<210> SEQ ID NO 109
<211> LENGTH: 22
<212> TYPE: PRT
<213> ORGANISM: Lotus japonicus

<400> SEQUENCE: 109

```
Val Tyr Gln Phe Asn Val Pro Thr Phe Gly Pro Gly Val Val Phe Asp
1               5                   10                  15

Val Asp Tyr Ser Val Arg
            20
```

<210> SEQ ID NO 110
<211> LENGTH: 13
<212> TYPE: PRT
<213> ORGANISM: Lotus japonicus

<400> SEQUENCE: 110

```
Phe Ala Gly Gln His Thr Ser Ser Ile Thr Ser Thr Trp
1               5                   10
```

<210> SEQ ID NO 111
<211> LENGTH: 11
<212> TYPE: PRT
<213> ORGANISM: Lotus japonicus

<400> SEQUENCE: 111

```
His Pro Pro Leu Ile Met Leu Leu Arg Ser Ser
1               5                   10
```

<210> SEQ ID NO 112
<211> LENGTH: 11
<212> TYPE: PRT
<213> ORGANISM: Lotus japonicus

<400> SEQUENCE: 112

```
Trp Asn Ala Met Val Val Gly Val Lys Gly Lys
1               5                   10
```

<210> SEQ ID NO 113
<211> LENGTH: 22
<212> TYPE: PRT
<213> ORGANISM: Arabidopsis thaliana

<400> SEQUENCE: 113

```
Val Tyr Gln Phe Asn Val Pro Thr Phe Gly Pro Gly Val Val Phe Asp
1               5                   10                  15

Val Asp Tyr Ser Val Arg
            20
```

<210> SEQ ID NO 114
<211> LENGTH: 13
<212> TYPE: PRT
<213> ORGANISM: Arabidopsis thaliana

<400> SEQUENCE: 114

```
Phe Ala Gly Gln His Thr Ser Ser Ile Thr Ser Thr Trp
1               5                   10
```

<210> SEQ ID NO 115
<211> LENGTH: 11
<212> TYPE: PRT
<213> ORGANISM: Arabidopsis thaliana

<400> SEQUENCE: 115

His Pro Pro Leu Ile Met Leu Met Arg Ala Ser
1               5                   10

<210> SEQ ID NO 116
<211> LENGTH: 11
<212> TYPE: PRT
<213> ORGANISM: Arabidopsis thaliana

<400> SEQUENCE: 116

Trp Asn Ala Met Val Val Gly Val Lys Gly Asn
1               5                   10

<210> SEQ ID NO 117
<211> LENGTH: 22
<212> TYPE: PRT
<213> ORGANISM: Pinus sp.

<400> SEQUENCE: 117

Val Tyr Gln Phe Asn Val Pro Thr Phe Gly Pro Gly Val Val Phe Asp
1               5                   10                  15

Val Asp Tyr Ser Val Arg
            20

<210> SEQ ID NO 118
<211> LENGTH: 13
<212> TYPE: PRT
<213> ORGANISM: Pinus sp.

<400> SEQUENCE: 118

Phe Ala Gly Gln His Thr Ser Ser Ile Thr Ser Thr Trp
1               5                   10

<210> SEQ ID NO 119
<211> LENGTH: 11
<212> TYPE: PRT
<213> ORGANISM: Pinus sp.

<400> SEQUENCE: 119

His Pro Pro Leu Ile Val Leu Leu Arg Ser Asn
1               5                   10

<210> SEQ ID NO 120
<211> LENGTH: 11
<212> TYPE: PRT
<213> ORGANISM: Pinus sp.

<400> SEQUENCE: 120

Trp Asn Ala Met Val Val Gly Val Lys Asp Lys
1               5                   10

<210> SEQ ID NO 121
<211> LENGTH: 22
<212> TYPE: PRT
<213> ORGANISM: Triticum aestivum

<400> SEQUENCE: 121

Val Tyr Arg Phe Asn Val Pro Thr Phe Gly Pro Gly Val Val Phe Asp
1               5                   10                  15

Val Asp Tyr Gln Val Arg
            20

<210> SEQ ID NO 122

```
<211> LENGTH: 13
<212> TYPE: PRT
<213> ORGANISM: Triticum aestivum

<400> SEQUENCE: 122

Phe Ala Gly Gln His Thr Ser Ser Ile Thr Ser Thr Trp
1               5                   10

<210> SEQ ID NO 123
<211> LENGTH: 11
<212> TYPE: PRT
<213> ORGANISM: Triticum aestivum

<400> SEQUENCE: 123

His Pro Pro Leu Ile Met Leu Leu Arg Gln Ser
1               5                   10

<210> SEQ ID NO 124
<211> LENGTH: 11
<212> TYPE: PRT
<213> ORGANISM: Triticum aestivum

<400> SEQUENCE: 124

Trp Asn Ala Met Val Val Gly Ile Lys Gly Glu
1               5                   10

<210> SEQ ID NO 125
<211> LENGTH: 22
<212> TYPE: PRT
<213> ORGANISM: Sorghum bicolor

<400> SEQUENCE: 125

Val Tyr Arg Phe Asn Val Pro Thr Phe Gly Pro Gly Val Val Phe Asp
1               5                   10                  15

Val Asp Tyr Ser Val Arg
            20

<210> SEQ ID NO 126
<211> LENGTH: 13
<212> TYPE: PRT
<213> ORGANISM: Sorghum bicolor

<400> SEQUENCE: 126

Phe Ala Gly Gln His Thr Ser Ser Ile Thr Ser Thr Trp
1               5                   10

<210> SEQ ID NO 127
<211> LENGTH: 11
<212> TYPE: PRT
<213> ORGANISM: Sorghum bicolor

<400> SEQUENCE: 127

His Pro Pro Leu Ile Met Leu Leu Arg Gln Ser
1               5                   10

<210> SEQ ID NO 128
<211> LENGTH: 11
<212> TYPE: PRT
<213> ORGANISM: Sorghum bicolor

<400> SEQUENCE: 128

Trp Asn Ala Met Val Val Gly Ile Lys Gly Glu
1               5                   10

<210> SEQ ID NO 129
```

```
<211> LENGTH: 22
<212> TYPE: PRT
<213> ORGANISM: Zea mays

<400> SEQUENCE: 129

Val Tyr Arg Phe Asn Val Pro Thr Phe Gly Pro Gly Val Val Phe Asp
1               5                   10                  15

Val Asp Tyr Ser Ile Arg
            20

<210> SEQ ID NO 130
<211> LENGTH: 13
<212> TYPE: PRT
<213> ORGANISM: Zea mays

<400> SEQUENCE: 130

Phe Ala Gly Gln His Thr Ser Ser Ile Thr Ser Thr Trp
1               5                   10

<210> SEQ ID NO 131
<211> LENGTH: 11
<212> TYPE: PRT
<213> ORGANISM: Zea mays

<400> SEQUENCE: 131

His Pro Pro Leu Ile Met Leu Leu Arg Gln Ser
1               5                   10

<210> SEQ ID NO 132
<211> LENGTH: 11
<212> TYPE: PRT
<213> ORGANISM: Zea mays

<400> SEQUENCE: 132

Trp Asn Ala Met Val Val Gly Ile Lys Gly Glu
1               5                   10

<210> SEQ ID NO 133
<211> LENGTH: 22
<212> TYPE: PRT
<213> ORGANISM: Oryza sativa

<400> SEQUENCE: 133

Val Tyr Lys Phe Asn Val Pro Thr Phe Gly Pro Gly Val Val Phe Asp
1               5                   10                  15

Val Asp Tyr Ser Val Arg
            20

<210> SEQ ID NO 134
<211> LENGTH: 13
<212> TYPE: PRT
<213> ORGANISM: Oryza sativa

<400> SEQUENCE: 134

Phe Ala Gly Gln His Thr Ser Ser Ile Thr Ser Thr Trp
1               5                   10

<210> SEQ ID NO 135
<211> LENGTH: 11
<212> TYPE: PRT
<213> ORGANISM: Oryza sativa

<400> SEQUENCE: 135

His Pro Pro Leu Ile Met Leu Leu Arg Gln Ser
1               5                   10
```

<210> SEQ ID NO 136
<211> LENGTH: 11
<212> TYPE: PRT
<213> ORGANISM: Oryza sativa

<400> SEQUENCE: 136

Trp Lys Ala Met Val Val Gly Ile Lys Asp Glu
1               5                   10

<210> SEQ ID NO 137
<211> LENGTH: 22
<212> TYPE: PRT
<213> ORGANISM: Avena strigosa

<400> SEQUENCE: 137

Val Tyr Arg Phe Asn Val Pro Thr Phe Gly Pro Gly Val Val Phe Asp
1               5                   10                  15

Val Asp Tyr Leu Val Arg
            20

<210> SEQ ID NO 138
<211> LENGTH: 13
<212> TYPE: PRT
<213> ORGANISM: Avena strigosa

<400> SEQUENCE: 138

Phe Ala Gly Gln His Thr Ser Ser Ile Thr Ser Thr Trp
1               5                   10

<210> SEQ ID NO 139
<211> LENGTH: 11
<212> TYPE: PRT
<213> ORGANISM: Avena strigosa

<400> SEQUENCE: 139

His Pro Pro Leu Ile Met Leu Leu Arg Gln Ser
1               5                   10

<210> SEQ ID NO 140
<211> LENGTH: 11
<212> TYPE: PRT
<213> ORGANISM: Avena strigosa

<400> SEQUENCE: 140

Trp Asn Ala Met Val Val Gly Ile Lys Gly Glu
1               5                   10

<210> SEQ ID NO 141
<211> LENGTH: 22
<212> TYPE: PRT
<213> ORGANISM: Avena strigosa

<400> SEQUENCE: 141

Phe Asn Glu Phe Thr Val Pro Met Phe Gly Lys Glu Asn Gly Tyr Ala
1               5                   10                  15

Val Glu Tyr Ala Thr Arg
            20

<210> SEQ ID NO 142
<211> LENGTH: 13
<212> TYPE: PRT
<213> ORGANISM: Avena strigosa

<400> SEQUENCE: 142

```
Phe Ala Gly Lys His Thr Ser Thr Ile Thr Ala Ser Trp
1               5                   10
```

<210> SEQ ID NO 143
<211> LENGTH: 11
<212> TYPE: PRT
<213> ORGANISM: Avena strigosa

<400> SEQUENCE: 143

```
Tyr Pro Ala Ala Pro Val Leu Leu Arg Lys Thr
1               5                   10
```

<210> SEQ ID NO 144
<211> LENGTH: 11
<212> TYPE: PRT
<213> ORGANISM: Avena strigosa

<400> SEQUENCE: 144

```
Trp Ser Lys Phe Ile Ile Glu Pro Lys Gly Lys
1               5                   10
```

<210> SEQ ID NO 145
<211> LENGTH: 451
<212> TYPE: PRT
<213> ORGANISM: Mycobacterium tuberculosis

<400> SEQUENCE: 145

```
Met Ser Ala Val Ala Leu Pro Arg Val Ser Gly Gly His Asp Glu His
1               5                   10                  15

Gly His Leu Glu Glu Phe Arg Thr Asp Pro Ile Gly Leu Met Gln Arg
            20                  25                  30

Val Arg Asp Glu Cys Gly Asp Val Gly Thr Phe Gln Leu Ala Gly Lys
        35                  40                  45

Gln Val Val Leu Leu Ser Gly Ser His Ala Asn Glu Phe Phe Phe Arg
    50                  55                  60

Ala Gly Asp Asp Asp Leu Asp Gln Ala Lys Ala Tyr Pro Phe Met Thr
65                  70                  75                  80

Pro Ile Phe Gly Glu Gly Val Val Phe Asp Ala Ser Pro Glu Arg Arg
                85                  90                  95

Lys Glu Met Leu His Asn Ala Ala Leu Arg Gly Glu Gln Met Lys Gly
            100                 105                 110

His Ala Ala Thr Ile Glu Asp Gln Val Arg Arg Met Ile Ala Asp Trp
        115                 120                 125

Gly Glu Ala Gly Glu Ile Asp Leu Leu Asp Phe Phe Ala Glu Leu Thr
    130                 135                 140

Ile Tyr Thr Ser Ser Ala Cys Leu Ile Gly Lys Lys Phe Arg Asp Gln
145                 150                 155                 160

Leu Asp Gly Arg Phe Ala Lys Leu Tyr His Glu Leu Glu Arg Gly Thr
                165                 170                 175

Asp Pro Leu Ala Tyr Val Asp Pro Tyr Leu Pro Ile Glu Ser Phe Arg
            180                 185                 190

Arg Arg Asp Glu Ala Arg Asn Gly Leu Val Ala Leu Val Ala Asp Ile
        195                 200                 205

Met Asn Gly Arg Ile Ala Asn Pro Pro Thr Asp Lys Ser Asp Arg Asp
    210                 215                 220

Met Leu Asp Val Leu Ile Ala Val Lys Ala Glu Thr Gly Thr Pro Arg
225                 230                 235                 240

Phe Ser Ala Asp Glu Ile Thr Gly Met Phe Ile Ser Met Met Phe Ala
```

```
                      245                 250                 255
Gly His His Thr Ser Ser Gly Thr Ala Ser Trp Thr Leu Ile Glu Leu
            260                 265                 270

Met Arg His Arg Asp Ala Tyr Ala Val Ile Asp Glu Leu Asp Glu
        275                 280                 285

Leu Tyr Gly Asp Gly Arg Ser Val Ser Phe His Ala Leu Arg Gln Ile
        290                 295                 300

Pro Gln Leu Glu Asn Val Leu Lys Glu Thr Leu Arg Leu His Pro Pro
305                 310                 315                 320

Leu Ile Ile Leu Met Arg Val Ala Lys Gly Glu Phe Glu Val Gln Gly
                325                 330                 335

His Arg Ile His Glu Gly Asp Leu Val Ala Ala Ser Pro Ala Ile Ser
            340                 345                 350

Asn Arg Ile Pro Glu Asp Phe Pro Asp Pro His Asp Phe Val Pro Ala
        355                 360                 365

Arg Tyr Glu Gln Pro Arg Gln Glu Asp Leu Leu Asn Arg Trp Thr Trp
        370                 375                 380

Ile Pro Phe Gly Ala Gly Arg His Arg Cys Val Gly Ala Ala Phe Ala
385                 390                 395                 400

Ile Met Gln Ile Lys Ala Ile Phe Ser Val Leu Leu Arg Glu Tyr Glu
                405                 410                 415

Phe Glu Met Ala Gln Pro Pro Glu Ser Tyr Arg Asn Asp His Ser Lys
            420                 425                 430

Met Val Val Gln Leu Ala Gln Pro Ala Cys Val Arg Tyr Arg Arg
        435                 440                 445

Thr Gly Val
        450

<210> SEQ ID NO 146
<211> LENGTH: 451
<212> TYPE: PRT
<213> ORGANISM: Mycobacterium avium

<400> SEQUENCE: 146

Met Thr Thr Ser Thr Val Val Pro Arg Val Ser Gly Gly Glu Glu Glu
1               5                   10                  15

His Gly His Leu Glu Glu Phe Arg Thr Asp Pro Ile Gly Leu Met Gln
            20                  25                  30

Arg Val Arg Asp Glu Cys Gly Asp Val Gly Trp Phe Gln Leu Val Asp
        35                  40                  45

Lys His Val Ile Leu Leu Ser Gly Ala Gln Ala Asn Glu Phe Phe Phe
    50                  55                  60

Arg Ser Ala Asp Glu Asp Leu Asp Gln Ala Glu Ala Tyr Pro Phe Met
65                  70                  75                  80

Thr Pro Ile Phe Gly Lys Gly Val Val Phe Asp Ala Ser Pro Glu Arg
                85                  90                  95

Arg Lys Glu Met Leu His Asn Ser Ala Leu Arg Gly Glu Gln Met Lys
            100                 105                 110

Gly His Ala Ser Thr Ile Glu Gly Glu Val Lys Lys Met Ile Ala Asp
        115                 120                 125

Trp Gly Asp Glu Gly Glu Ile Glu Leu Leu Asp Phe Phe Ala Glu Leu
    130                 135                 140

Thr Ile Tyr Thr Ser Thr Ala Cys Leu Ile Gly Leu Lys Phe Arg Glu
145                 150                 155                 160

Gln Leu Asp His Arg Phe Ala Glu Tyr Tyr His Asp Leu Glu Arg Gly
```

```
                    165                 170                 175
Thr Asp Pro Leu Cys Tyr Val Asp Pro Tyr Leu Pro Ile Glu Ser Phe
                180                 185                 190
Lys Arg Arg Asp Glu Ala Arg Val Lys Leu Val Ala Leu Val Gln Glu
            195                 200                 205
Ile Met Asp Gln Arg Leu Ala Asn Pro Pro Lys Asp Lys Ala Asp Arg
        210                 215                 220
Asp Met Leu Asp Val Leu Val Ser Ile Lys Asp Glu Asp Gly Lys Pro
225                 230                 235                 240
Arg Phe Ser Ala Asp Glu Ile Thr Gly Met Phe Ile Ser Leu Met Phe
                245                 250                 255
Ala Gly His His Thr Ser Ser Gly Thr Ser Ala Trp Thr Leu Ile Glu
            260                 265                 270
Leu Ile Arg His Pro Asp Val Tyr Ala Glu Val Leu Ala Glu Leu Glu
        275                 280                 285
Glu Leu Tyr Ala Asp Gly Gln Glu Val Ser Phe His Ala Leu Arg Ser
        290                 295                 300
Ile Pro Lys Leu Asp Asn Val Val Lys Glu Thr Leu Arg Leu His Pro
305                 310                 315                 320
Pro Leu Ile Ile Leu Met Arg Val Ala Lys Gly Glu Phe Glu Val Glu
                325                 330                 335
Gly Phe Pro Ile His Glu Gly Asp Tyr Val Ala Ala Ser Pro Ala Ile
            340                 345                 350
Ser Asn Arg Ile Pro Glu Asp Phe Pro Asp Pro Asp Ala Phe Lys Pro
        355                 360                 365
Asp Arg Tyr Asn Lys Pro Glu Gln Ala Asp Ile Val Asn Arg Trp Thr
    370                 375                 380
Trp Ile Pro Phe Gly Ala Gly Arg His Arg Cys Val Gly Ala Ala Phe
385                 390                 395                 400
Ala Gln Met Gln Ile Lys Ala Ile Phe Ser Val Leu Leu Arg Glu Tyr
                405                 410                 415
Asp Phe Glu Met Ala Gln Pro Ala Asp Ser Tyr Arg Asn Asp His Ser
            420                 425                 430
Lys Met Val Val Gln Leu Ala Arg Pro Ala Lys Val Arg Tyr Arg Lys
        435                 440                 445
Arg Asn Ala
    450

<210> SEQ ID NO 147
<211> LENGTH: 452
<212> TYPE: PRT
<213> ORGANISM: Mycobacterium vanbaalenii

<400> SEQUENCE: 147

Met Thr Ala Val Lys Glu Val Pro Arg Val Ser Gly Gly Glu Glu
1               5                   10                  15

His Gly His Leu Glu Glu Phe Arg Thr Asp Pro Ile Gly Leu Met Lys
                20                  25                  30

Arg Val Arg Glu Glu Cys Gly Asp Val Gly Trp Phe Gln Leu Ala Asp
            35                  40                  45

Lys Gln Val Ile Leu Leu Ser Gly Ala Glu Ala Asn Glu Phe Phe Phe
        50                  55                  60

Arg Ser Ser Asp Ser Glu Leu Asn Gln Ala Glu Ala Tyr Pro Phe Met
65                  70                  75                  80

Thr Pro Ile Phe Gly Glu Gly Val Val Phe Asp Ala Asp Pro Glu Arg
```

```
                85                  90                  95
Arg Ala Glu Met Leu His Asn Thr Ala Leu Arg Gly Glu His Met Lys
            100                 105                 110
Gly His Ala Thr Thr Ile Glu Ala Glu Val Arg Lys Met Ile Glu Gly
            115                 120                 125
Trp Gly Glu Ser Gly Glu Ile Asp Leu Leu Glu Phe Phe Ala Glu Leu
            130                 135                 140
Thr Ile Tyr Thr Ser Thr Ala Cys Leu Ile Gly Leu Lys Phe Arg Asn
145                 150                 155                 160
Gln Leu Asp Ser Arg Phe Ala Asn Tyr Tyr His Leu Leu Glu Arg Gly
                165                 170                 175
Thr Asp Pro Leu Cys Tyr Val Asp Pro Tyr Leu Pro Ile Glu Ser Phe
                180                 185                 190
Arg Ile Arg Asp Glu Ala Arg Ala Gly Leu Val Glu Leu Val Gln Asp
                195                 200                 205
Val Met His Gly Arg Ile Ala Asn Pro Pro Lys Asp Lys Ser Asp Arg
            210                 215                 220
Asp Met Leu Asp Val Leu Val Ser Ile Lys Asp Glu Asp Gly Asn Pro
225                 230                 235                 240
Arg Phe Thr Ala Asn Glu Ile Thr Gly Met Phe Ile Ser Leu Met Phe
                245                 250                 255
Ala Gly His His Thr Ser Ser Gly Thr Ser Ser Trp Thr Leu Ile Glu
                260                 265                 270
Leu Leu Arg His Pro Glu Phe Tyr Ala Lys Val Gln Gln Glu Leu Asp
            275                 280                 285
Asp Leu Tyr Ala Asp Gly Gln Glu Val Ser Phe His Ala Leu Arg Gln
            290                 295                 300
Ile Pro Ser Leu Asp Asn Ala Leu Lys Glu Thr Leu Arg Leu His Pro
305                 310                 315                 320
Pro Leu Ile Ile Leu Met Arg Val Ala Gln Asp Glu Phe Glu Val Ala
                325                 330                 335
Gly Tyr Pro Ile His Lys Gly Gln Met Val Ala Ala Ser Pro Ala Ile
            340                 345                 350
Ser Asn Arg Ile Pro Glu Asp Phe Pro Asn Pro Asp Asp Phe Asp Pro
            355                 360                 365
Asp Arg Tyr Glu Lys Pro Arg Gln Glu Asp Leu Ile Asn Arg Trp Thr
            370                 375                 380
Trp Ile Pro Phe Gly Ala Gly Lys His Arg Cys Val Gly Ala Ala Phe
385                 390                 395                 400
Ala Gln Met Gln Ile Lys Ala Ile Phe Ser Val Leu Leu Arg Glu Tyr
                405                 410                 415
Glu Phe Glu Met Ala Gln Pro Pro Glu Ser Tyr Gln Asn Asp His Ser
            420                 425                 430
Lys Met Val Val Gln Leu Ala Arg Pro Ala Lys Val Arg Tyr Arg Arg
            435                 440                 445
Arg Val Arg Asp
    450

<210> SEQ ID NO 148
<211> LENGTH: 481
<212> TYPE: PRT
<213> ORGANISM: Trypanosoma brucei

<400> SEQUENCE: 148

Met Leu Leu Glu Val Ala Ile Phe Leu Leu Thr Ala Leu Ala Leu Tyr
```

-continued

```
1               5                   10                  15
Ser Phe Tyr Phe Val Lys Ser Phe Asn Val Thr Arg Pro Thr Asp Pro
                20                  25                  30

Pro Val Tyr Pro Val Thr Val Pro Ile Leu Gly His Ile Ile Gln Phe
                35                  40                  45

Gly Lys Ser Pro Leu Gly Phe Met Gln Glu Cys Lys Arg Gln Leu Lys
            50                  55                  60

Ser Gly Ile Phe Thr Ile Asn Ile Val Gly Lys Arg Val Thr Ile Val
65                  70                  75                  80

Gly Asp Pro His Glu His Ser Arg Phe Phe Leu Pro Arg Asn Glu Val
                    85                  90                  95

Leu Ser Pro Arg Glu Val Tyr Ser Phe Met Glu Pro Val Phe Gly Glu
                100                 105                 110

Gly Val Ala Tyr Ala Ala Pro Tyr Pro Arg Met Arg Glu Gln Leu Asn
                115                 120                 125

Phe Leu Ala Glu Glu Leu Thr Ile Ala Lys Phe Gln Asn Phe Val Pro
            130                 135                 140

Ala Ile Gln His Glu Val Arg Lys Phe Met Ala Ala Asn Trp Asp Lys
145                 150                 155                 160

Asp Glu Gly Glu Ile Asn Leu Leu Glu Asp Cys Ser Thr Met Ile Ile
                    165                 170                 175

Asn Thr Ala Cys Gln Cys Leu Phe Gly Glu Asp Leu Arg Lys Arg Leu
                180                 185                 190

Asp Ala Arg Arg Phe Ala Gln Leu Leu Ala Lys Met Glu Ser Ser Leu
            195                 200                 205

Ile Pro Ala Ala Val Phe Leu Pro Ile Leu Lys Leu Pro Leu Pro
            210                 215                 220

Gln Ser Ala Arg Cys His Glu Ala Arg Thr Glu Leu Gln Lys Ile Leu
225                 230                 235                 240

Ser Glu Ile Ile Ile Ala Arg Lys Glu Glu Val Asn Lys Asp Ser
                    245                 250                 255

Ser Thr Ser Asp Leu Leu Ser Gly Leu Leu Ser Ala Val Tyr Arg Asp
                260                 265                 270

Gly Thr Pro Met Ser Leu His Glu Val Cys Gly Met Ile Val Ala Ala
            275                 280                 285

Met Phe Ala Gly Gln His Thr Ser Ser Ile Thr Thr Thr Trp Ser Met
            290                 295                 300

Leu His Leu Met His Pro Ala Asn Val Lys His Leu Glu Ala Leu Arg
305                 310                 315                 320

Lys Glu Ile Glu Glu Phe Pro Ala Gln Leu Asn Tyr Asn Asn Val Met
                325                 330                 335

Asp Glu Met Pro Phe Ala Glu Arg Cys Ala Arg Glu Ser Ile Arg Arg
            340                 345                 350

Asp Pro Pro Leu Leu Met Leu Met Arg Lys Val Met Ala Asp Val Lys
            355                 360                 365

Val Gly Ser Tyr Val Val Pro Lys Gly Asp Ile Ile Ala Cys Ser Pro
        370                 375                 380

Leu Leu Ser His His Asp Glu Glu Ala Phe Pro Glu Pro Arg Arg Trp
385                 390                 395                 400

Asp Pro Glu Arg Asp Glu Lys Val Glu Gly Ala Phe Ile Gly Phe Gly
                    405                 410                 415

Ala Gly Val His Lys Cys Ile Gly Gln Lys Phe Gly Leu Leu Gln Val
                420                 425                 430
```

```
Lys Thr Ile Leu Ala Thr Ala Phe Arg Ser Tyr Asp Phe Gln Leu Leu
            435                 440                 445

Arg Asp Glu Val Pro Asp Pro Asp Tyr His Thr Met Val Val Gly Pro
450                 455                 460

Thr Ala Ser Gln Cys Arg Val Lys Tyr Ile Arg Arg Lys Ala Ala Ala
465                 470                 475                 480

Ala

<210> SEQ ID NO 149
<211> LENGTH: 481
<212> TYPE: PRT
<213> ORGANISM: Trypanosoma cruzi

<400> SEQUENCE: 149

Met Phe Ile Glu Ala Ile Val Leu Ala Leu Thr Ala Leu Ile Leu Tyr
1               5                   10                  15

Ser Val Tyr Ser Val Lys Ser Phe Asn Thr Thr Arg Pro Thr Asp Pro
            20                  25                  30

Pro Val Tyr Pro Val Thr Val Pro Phe Leu Gly His Ile Val Gln Phe
            35                  40                  45

Gly Lys Asn Pro Leu Glu Phe Met Gln Arg Cys Lys Arg Asp Leu Lys
50                  55                  60

Ser Gly Val Phe Thr Ile Ser Ile Gly Gly Gln Arg Val Thr Ile Val
65                  70                  75                  80

Gly Asp Pro His Glu His Ser Arg Phe Ser Pro Arg Asn Glu Ile
                85                  90                  95

Leu Ser Pro Arg Glu Val Tyr Thr Ile Met Thr Pro Val Phe Gly Glu
            100                 105                 110

Gly Val Ala Tyr Ala Ala Pro Tyr Pro Arg Met Arg Glu Gln Leu Asn
            115                 120                 125

Phe Leu Ala Glu Glu Leu Thr Ile Ala Lys Phe Gln Asn Phe Val Pro
130                 135                 140

Ala Ile Gln His Glu Val Arg Lys Phe Met Ala Glu Asn Trp Lys Glu
145                 150                 155                 160

Asp Glu Gly Val Ile Asn Leu Leu Glu Asp Cys Gly Ala Met Ile Ile
                165                 170                 175

Asn Thr Ala Cys Gln Cys Leu Phe Gly Glu Asp Leu Arg Lys Arg Leu
            180                 185                 190

Asn Ala Arg His Phe Ala Gln Leu Leu Ser Lys Met Glu Ser Ser Leu
            195                 200                 205

Ile Pro Ala Ala Val Phe Met Pro Trp Leu Leu Arg Leu Pro Leu Pro
210                 215                 220

Gln Ser Ala Arg Cys Arg Glu Ala Arg Ala Glu Leu Gln Lys Ile Leu
225                 230                 235                 240

Gly Glu Ile Ile Val Ala Arg Glu Lys Glu Glu Ala Ser Lys Asp Asn
                245                 250                 255

Asn Thr Ser Asp Leu Leu Gly Gly Leu Leu Lys Ala Val Tyr Arg Asp
            260                 265                 270

Gly Thr Arg Met Ser Leu His Glu Val Cys Gly Met Ile Val Ala Ala
            275                 280                 285

Met Phe Ala Gly Gln His Thr Ser Thr Ile Thr Ser Trp Ser Met
290                 295                 300

Leu His Leu Met His Pro Lys Asn Lys Lys Trp Leu Asp Lys Leu His
305                 310                 315                 320

Lys Glu Ile Asp Glu Phe Pro Ala Gln Leu Asn Tyr Asp Asn Val Met
```

```
              325                 330                 335
Asp Glu Met Pro Phe Ala Glu Arg Cys Val Arg Glu Ser Ile Arg Arg
            340                 345                 350

Asp Pro Pro Leu Leu Met Val Met Arg Met Val Lys Ala Glu Val Lys
            355                 360                 365

Val Gly Ser Tyr Val Val Pro Lys Gly Asp Ile Ile Ala Cys Ser Pro
            370                 375                 380

Leu Leu Ser His His Asp Glu Glu Ala Phe Pro Asn Pro Arg Leu Trp
385                 390                 395                 400

Asp Pro Glu Arg Asp Glu Lys Val Asp Gly Ala Phe Ile Gly Phe Gly
            405                 410                 415

Ala Gly Val His Lys Cys Ile Gly Gln Lys Phe Ala Leu Leu Gln Val
            420                 425                 430

Lys Thr Ile Leu Ala Thr Ala Phe Arg Glu Tyr Asp Phe Gln Leu Leu
            435                 440                 445

Arg Asp Glu Val Pro Asp Pro Asp Tyr His Thr Met Val Val Gly Pro
450                 455                 460

Thr Leu Asn Gln Cys Leu Val Lys Tyr Thr Arg Lys Lys Leu Pro
465                 470                 475                 480

Ser

<210> SEQ ID NO 150
<211> LENGTH: 479
<212> TYPE: PRT
<213> ORGANISM: Leishmania major

<400> SEQUENCE: 150

Met Ile Gly Glu Phe Phe Leu Leu Thr Ala Gly Leu Ala Leu Tyr
1               5                   10                  15

Gly Trp Tyr Phe Cys Lys Ser Phe Asn Thr Thr Arg Pro Thr Asp Pro
                20                  25                  30

Pro Val Val His Gly Ala Met Pro Phe Val Gly His Ile Ile Gln Phe
            35                  40                  45

Gly Lys Asp Pro Leu Asp Phe Met Leu Asn Ala Lys Lys Lys Tyr Gly
        50                  55                  60

Gly Val Phe Thr Met Asn Ile Cys Gly Asn Arg Val Thr Val Val Gly
65                  70                  75                  80

Asp Val His Gln His Asn Lys Phe Phe Thr Pro Arg Asn Glu Ile Leu
                85                  90                  95

Ser Pro Arg Glu Val Tyr Ser Phe Met Val Pro Val Phe Gly Glu Gly
            100                 105                 110

Val Ala Tyr Ala Ala Pro Tyr Pro Arg Met Arg Glu Gln Leu Asn Phe
        115                 120                 125

Leu Ala Glu Glu Leu Thr Val Ala Lys Phe Gln Asn Phe Ala Pro Ser
130                 135                 140

Ile Gln His Glu Val Arg Lys Phe Met Lys Ala Asn Trp Asn Lys Asp
145                 150                 155                 160

Glu Gly Glu Ile Asn Ile Leu Asp Asp Cys Ser Ala Met Ile Ile Asn
                165                 170                 175

Thr Ala Cys Gln Cys Leu Phe Gly Glu Asp Leu Arg Lys Arg Leu Asp
            180                 185                 190

Ala Arg Gln Phe Ala Gln Leu Leu Ala Lys Met Glu Ser Cys Leu Ile
        195                 200                 205

Pro Ala Ala Val Phe Leu Pro Trp Ile Leu Lys Leu Pro Leu Pro Gln
210                 215                 220
```

Ser Tyr Arg Cys Arg Asp Ala Arg Ala Glu Leu Gln Asp Ile Leu Ser
225                 230                 235                 240

Glu Ile Ile Ile Ala Arg Glu Lys Glu Ala Gln Lys Asp Ser Asn
            245                 250                 255

Thr Ser Asp Leu Leu Ala Ser Leu Leu Gly Ala Val Tyr Arg Asp Gly
        260                 265                 270

Thr Arg Met Ser Gln His Glu Val Cys Gly Met Ile Val Ala Ala Met
            275                 280                 285

Phe Ala Gly Gln His Thr Ser Thr Ile Thr Thr Trp Ser Leu Leu
        290                 295                 300

His Leu Met Asp Pro Arg Asn Lys Arg His Leu Ala Lys Leu His Gln
305                 310                 315                 320

Glu Ile Asp Glu Phe Pro Ala Gln Leu Asn Tyr Asp Asn Val Met Glu
                325                 330                 335

Glu Met Pro Phe Ala Glu Gln Cys Ala Arg Glu Ser Ile Arg Arg Asp
            340                 345                 350

Pro Pro Leu Ile Met Leu Met Arg Lys Val Leu Lys Pro Val Gln Val
        355                 360                 365

Gly Lys Cys Val Val Pro Glu Gly Asp Ile Ile Ala Cys Ser Pro Leu
    370                 375                 380

Leu Ser His Gln Asp Glu Glu Ala Phe Pro Asn Pro Arg Glu Trp Asn
385                 390                 395                 400

Pro Glu Arg Asn Met Lys Leu Val Asp Gly Ala Phe Cys Gly Phe Gly
                405                 410                 415

Ala Gly Val His Lys Cys Ile Gly Glu Lys Phe Gly Leu Leu Gln Val
            420                 425                 430

Lys Thr Val Leu Ala Thr Val Leu Arg Asp Tyr Asp Phe Glu Leu Leu
        435                 440                 445

Gly Pro Leu Pro Glu Pro Asn Tyr His Thr Met Val Val Gly Pro Thr
    450                 455                 460

Ala Ser Gln Cys Arg Val Lys Tyr Ile Arg Lys Lys Ala Ala Ala
465                 470                 475

<210> SEQ ID NO 151
<211> LENGTH: 497
<212> TYPE: PRT
<213> ORGANISM: Abudefduf saxatilis
<220> FEATURE:
<221> NAME/KEY: MISC_FEATURE
<222> LOCATION: (383)..(383)
<223> OTHER INFORMATION: Xaa is unknown

<400> SEQUENCE: 151

Met His Phe Tyr Gln Ile Gly Ser Lys Leu Leu Gly Asp Thr Val Glu
1               5                   10                  15

Arg Met Asn Asp Asn Leu Thr Ser Val Val Leu Ala Ala Ser Val Ile
                20                  25                  30

Thr Leu Thr Leu Ala Tyr Val Ser Lys Leu Leu Leu Lys Gln Thr Pro
            35                  40                  45

Asp Lys Asp Gln Lys Tyr Pro Pro Tyr Ile Pro Ser Ser Ile Pro Phe
        50                  55                  60

Leu Gly His Ala Ile Ala Phe Gly Lys Ser Pro Ile Glu Phe Leu Glu
65                  70                  75                  80

Asn Ala Tyr Asp Lys Tyr Gly Pro Val Phe Ser Phe Thr Met Val Gly
                85                  90                  95

Lys Thr Phe Thr Tyr Leu Leu Gly Ser Glu Ala Ala Thr Leu Leu Phe

```
                100              105                110
Asn Ser Lys Asn Glu Asp Leu Asn Ala Glu Asp Val Tyr Ser Arg Leu
            115                 120             125

Thr Thr Pro Val Phe Gly Lys Gly Val Ala Tyr Asp Val Pro Asn Pro
130                     135             140

Ile Phe Leu Glu Gln Lys Lys Met Leu Lys Thr Gly Leu Asn Ile Ala
145                 150                 155                 160

His Phe Lys Glu His Val Lys Ile Ile Glu Ala Glu Thr Ile Glu Tyr
                165                 170                 175

Phe Gln Arg Trp Gly Asp Ser Gly Glu Arg Asn Leu Phe Glu Ala Leu
            180                 185             190

Ser Glu Leu Ile Ile Leu Thr Ala Ser Ser Cys Leu His Gly Lys Glu
        195                 200             205

Ile Arg Ser Met Leu Asp Glu Arg Val Ala Gln Leu Tyr Ala Asp Leu
        210                 215             220

Asp Gly Gly Phe Ser His Ala Ala Trp Leu Leu Pro Gly Trp Leu Pro
225                 230             235                 240

Leu Pro Ser Phe Arg Lys Arg Asp Lys Ala His Met Glu Ile Lys Asn
                245                 250                 255

Ile Phe Tyr Glu Val Thr Gln Lys Arg Arg Arg Ser Gly Glu Lys Val
                260             265                 270

Asp Asp Ile Leu Gln Thr Leu Ile Asp Ala Thr Tyr Lys Asp Gly Arg
        275                 280             285

Pro Leu Asn Asp Asp Glu Ile Ala Gly Met Leu Ile Gly Leu Leu Leu
        290                 295             300

Ala Gly Gln His Thr Ser Ser Thr Thr Ser Ala Trp Met Gly Phe Phe
305                 310                 315                 320

Leu Ala Arg Asp Lys Ala Leu Gln Glu Arg Cys Tyr Ala Glu Gln Lys
                325             330                 335

Ala Met Cys Gly Asp Asp Leu Pro Ser Leu Asp Phe Asp Gln Leu Lys
                340                 345             350

Asp Leu Ser Leu Leu Glu Arg Cys Leu Lys Glu Thr Leu Arg Leu Arg
        355                 360             365

Pro Pro Ile Met Thr Met Met Arg Met Ala Arg Ser Pro Gln Xaa Ala
370                 375                 380

Ala Gly Tyr Thr Ile Pro Val Gly His Gln Val Cys Val Ser Pro Thr
385                 390             395                 400

Val Asn His Arg Leu His Asp Thr Trp Ala Glu Arg Met Glu Phe Lys
                405                 410                 415

Pro Asp Arg Tyr Leu Asn Asp Asn Pro Ala Ala Gly Glu Lys Phe Ala
                420             425                 430

Tyr Val Pro Phe Gly Ala Gly Arg His Arg Cys Ile Gly Glu Asn Phe
            435                 440             445

Ala Tyr Val Gln Ile Lys Thr Ile Trp Ser Thr Leu Leu Arg Leu Tyr
            450                 455             460

Asp Phe Asp Leu Val Asp Gly Tyr Phe Pro Thr Ile Asn Tyr Thr Thr
465                 470                 475                 480

Met Ile His Thr Pro His Asn Pro Val Ile Arg Tyr Lys Arg Arg Lys
                485                 490                 495

Gln

<210> SEQ ID NO 152
<211> LENGTH: 499
<212> TYPE: PRT
```

<213> ORGANISM: Fundulus heteroclitus

<400> SEQUENCE: 152

Met Ser Thr His Phe Tyr Asn Met Gly Thr Lys Leu Leu Val Asp Thr
1               5                   10                  15

Val Ser Lys Met Asn Glu Asn Leu Thr Ser Leu Val Leu Ala Ala Ser
            20                  25                  30

Val Phe Thr Leu Thr Val Gly Tyr Val Ser Lys Arg Leu Leu Gln Gln
        35                  40                  45

Ser Ala Asp Lys Asp Ala Lys Tyr Pro Pro Phe Ile Pro Ser Ser Ile
    50                  55                  60

Pro Phe Leu Gly His Ala Ile Ala Phe Gly Lys Ser Pro Ile Glu Phe
65                  70                  75                  80

Leu Glu Asn Ala Tyr Glu Lys Tyr Gly Pro Val Phe Ser Phe Thr Met
                85                  90                  95

Val Gly Lys Thr Phe Thr Tyr Leu Leu Gly Ser Glu Ala Ala Thr Leu
            100                 105                 110

Met Phe Asn Ser Lys Asn Glu Asp Leu Asn Ala Glu Asp Val Tyr Ser
        115                 120                 125

Lys Leu Thr Thr Pro Val Phe Gly Lys Gly Val Ala Tyr Asp Val Pro
    130                 135                 140

Asn Pro Ile Phe Leu Glu Gln Lys Lys Met Leu Lys Thr Gly Leu Asn
145                 150                 155                 160

Ile Ala Arg Phe Lys Glu His Val Arg Leu Ile Glu Ser Glu Thr Ile
                165                 170                 175

Glu Tyr Phe Lys Arg Trp Gly Asp Ser Gly Glu Arg Asn Leu Phe Glu
            180                 185                 190

Ala Leu Ser Glu Leu Ile Ile Leu Thr Ala Ser Ser Cys Leu His Gly
        195                 200                 205

Lys Glu Ile Arg Ser Met Leu Asn Glu Arg Val Ala Gln Leu Tyr Ala
    210                 215                 220

Asp Leu Asp Gly Gly Phe Ser His Ala Ala Trp Leu Leu Pro Thr Trp
225                 230                 235                 240

Val Pro Leu Pro Ser Phe Arg Lys Arg Asp Lys Ala His Arg Glu Ile
                245                 250                 255

Lys Asn Ile Phe Phe Lys Val Ile Glu Lys Arg Arg Ser Gly Glu
            260                 265                 270

Thr Pro Asp Asp Ile Leu Gln Thr Leu Ile Asp Ala Thr Tyr Lys Asp
        275                 280                 285

Gly Arg Ser Leu Thr Asp Asp Glu Ile Ala Gly Met Leu Ile Gly Leu
    290                 295                 300

Leu Leu Ala Gly Gln His Thr Ser Ser Thr Thr Ser Ala Trp Met Gly
305                 310                 315                 320

Phe Phe Leu Ala Arg Asp Lys Ala Leu Gln Asp Arg Cys Tyr Ala Glu
                325                 330                 335

Gln Lys Ala Val Cys Gly Glu Gly Leu Pro Pro Leu Asp Phe Asp Gln
            340                 345                 350

Leu Lys Asp Leu Asn Leu Leu Glu Arg Cys Leu Lys Glu Thr Leu Arg
        355                 360                 365

Leu Arg Pro Pro Ile Met Thr Met Met Arg Met Ala Arg Thr Pro Gln
    370                 375                 380

Thr Ala Ala Gly Tyr Thr Ile Pro Val Gly His Gln Val Cys Val Ser
385                 390                 395                 400

Pro Thr Val Asn His Arg Leu Gln Asp Ala Trp Val Gly Arg Met Glu

```
                    405                 410                 415
Phe Asn Pro Glu Arg Tyr Leu Asn Asp Asn Pro Ala Ala Gly Glu Lys
            420                 425                 430

Phe Ala Tyr Ile Pro Phe Gly Ala Gly Arg His Arg Cys Ile Gly Glu
            435                 440                 445

Asn Phe Ala Tyr Val Gln Ile Lys Thr Ile Trp Ser Thr Met Leu Arg
            450                 455                 460

Met Tyr Glu Phe Asp Leu Val Asp Gly Tyr Phe Pro Thr Ile Asn Tyr
465                 470                 475                 480

Thr Thr Met Ile His Thr Pro His Asn Pro Val Ile Arg Tyr Lys Arg
                485                 490                 495

Arg Lys Gln

<210> SEQ ID NO 153
<211> LENGTH: 499
<212> TYPE: PRT
<213> ORGANISM: Danio rerio

<400> SEQUENCE: 153

Met Thr Ile Leu Glu Val Gly Ser Gln Leu Ile Glu Ser Ala Val Leu
1               5                   10                  15

Gln Met Ser Leu Thr Ser Val Leu Leu Thr Ala Ser Val Phe Thr Leu
            20                  25                  30

Thr Leu Gly Tyr Ile Ser Lys Leu Leu Phe Thr Gln His Ser Ser Glu
        35                  40                  45

His Thr Lys Tyr Pro Pro His Ile Pro Ser Ser Leu Pro Phe Leu Gly
    50                  55                  60

Gln Ala Val Ala Phe Gly Arg Ser Pro Ile Glu Phe Leu Glu Lys Ala
65                  70                  75                  80

Tyr Glu Gln Tyr Gly Pro Val Val Ser Phe Thr Met Val Gly Lys Thr
                85                  90                  95

Phe Thr Tyr Leu Leu Gly Ser Asp Ala Ala Ala Leu Met Phe Asn Ser
            100                 105                 110

Lys Asn Glu Asp Leu Asn Ala Glu Asp Val Tyr Ala Arg Leu Thr Thr
        115                 120                 125

Pro Val Phe Gly Lys Gly Val Ala Tyr Asp Val Pro Asn Pro Leu Phe
    130                 135                 140

Leu Glu Gln Lys Lys Met Leu Lys Thr Gly Leu Asn Ile Ala Gln Phe
145                 150                 155                 160

Lys Gln His Val Glu Ile Ile Glu Glu Glu Thr Lys Asp Tyr Phe Arg
                165                 170                 175

Arg Trp Gly Glu Ser Gly Glu Arg Asn Leu Phe Asp Ala Leu Ser Glu
            180                 185                 190

Leu Ile Ile Leu Thr Ala Ser Arg Cys Leu His Gly Cys Glu Ile Arg
        195                 200                 205

Ser Leu Leu Asp Glu Arg Val Ala Gln Leu Tyr Ala Asp Leu Asp Gly
    210                 215                 220

Gly Phe Thr His Ala Ala Trp Leu Leu Pro Gly Trp Leu Pro Leu Pro
225                 230                 235                 240

Ser Phe Arg Arg Arg Asp Arg Ala His Leu Glu Ile Lys Lys Ile Phe
                245                 250                 255

Tyr Asn Val Ile Lys Lys Arg Arg Glu Asp Thr Glu Lys His Asp Asp
            260                 265                 270

Ile Leu Gln Thr Leu Ile Asp Ala Thr Tyr Lys Asp Gly Arg Pro Leu
        275                 280                 285
```

-continued

Ser Asp Asp Glu Ile Ala Gly Met Leu Ile Gly Leu Leu Ala Gly
    290                 295                 300

Gln His Thr Ser Ser Thr Thr Ser Ala Trp Met Gly Phe Phe Leu Ala
305                 310                 315                 320

Arg Asp Arg Ala Leu Gln Glu Arg Cys Tyr Ser Glu Gln Lys Ser Val
                325                 330                 335

Cys Gly Glu Glu Leu Pro Pro Leu His Tyr Asp Gln Leu Lys Asp Leu
            340                 345                 350

Ser Leu Leu Asp Arg Cys Leu Lys Glu Thr Leu Arg Leu Arg Pro Pro
        355                 360                 365

Ile Met Thr Met Met Arg Met Ala Lys Thr Pro Gln Lys Val Gly Glu
370                 375                 380

Tyr Thr Ile Pro Pro Gly His Gln Val Cys Val Ser Pro Thr Val Asn
385                 390                 395                 400

His Arg Leu Gln Asp Thr Trp Ala Glu Arg Leu Asp Phe Asp Pro Asp
                405                 410                 415

Arg Tyr Leu His Asp Asn Pro Ala Ala Gly Glu Lys Phe Ala Tyr Ile
            420                 425                 430

Pro Phe Gly Ala Gly Arg His Arg Cys Ile Gly Glu Asn Phe Ala Tyr
        435                 440                 445

Val Gln Ile Lys Thr Ile Trp Ser Thr Leu Leu Arg Met Phe Asp Phe
    450                 455                 460

Glu Leu Val Asp Gly His Phe Pro Pro Val Asn Tyr Thr Thr Met Ile
465                 470                 475                 480

His Thr Pro His Asn Pro Ile Ile Arg Tyr Thr Arg Arg Asn Ala Gln
                485                 490                 495

Pro Gln Gln

<210> SEQ ID NO 154
<211> LENGTH: 503
<212> TYPE: PRT
<213> ORGANISM: Homo sapiens

<400> SEQUENCE: 154

Met Leu Leu Leu Gly Leu Leu Gln Ala Gly Gly Ser Val Leu Gly Gln
1               5                   10                  15

Ala Met Glu Lys Val Thr Gly Gly Asn Leu Leu Ser Met Leu Leu Ile
                20                  25                  30

Ala Cys Ala Phe Thr Leu Ser Leu Val Tyr Leu Ile Arg Leu Ala Ala
            35                  40                  45

Gly His Leu Val Gln Leu Pro Ala Gly Val Lys Ser Pro Pro Tyr Ile
        50                  55                  60

Phe Ser Pro Ile Pro Phe Leu Gly His Ala Ile Ala Phe Gly Lys Ser
65                  70                  75                  80

Pro Ile Glu Phe Leu Glu Asn Ala Tyr Glu Lys Tyr Gly Pro Val Phe
                85                  90                  95

Ser Phe Thr Met Val Gly Lys Thr Phe Thr Tyr Leu Leu Gly Ser Asp
            100                 105                 110

Ala Ala Ala Leu Leu Phe Asn Ser Lys Asn Glu Asp Leu Asn Ala Glu
        115                 120                 125

Asp Val Tyr Ser Arg Leu Thr Thr Pro Val Phe Gly Lys Gly Val Ala
    130                 135                 140

Tyr Asp Val Pro Asn Pro Val Phe Leu Glu Gln Lys Lys Met Leu Lys
145                 150                 155                 160

```
Ser Gly Leu Asn Ile Ala His Phe Lys Gln His Val Ser Ile Ile Glu
            165                 170                 175

Lys Glu Thr Lys Glu Tyr Phe Glu Ser Trp Gly Glu Ser Gly Glu Lys
        180                 185                 190

Asn Val Phe Glu Ala Leu Ser Glu Leu Ile Ile Leu Thr Ala Ser His
    195                 200                 205

Cys Leu His Gly Lys Glu Ile Arg Ser Gln Leu Asn Glu Lys Val Ala
210                 215                 220

Gln Leu Tyr Ala Asp Leu Asp Gly Phe Ser His Ala Ala Trp Leu
225                 230                 235                 240

Leu Pro Gly Trp Leu Pro Leu Pro Ser Phe Arg Arg Arg Asp Arg Ala
                245                 250                 255

His Arg Glu Ile Lys Asp Ile Phe Tyr Lys Ala Ile Gln Lys Arg Arg
            260                 265                 270

Gln Ser Gln Glu Lys Ile Asp Asp Ile Leu Gln Thr Leu Leu Asp Ala
        275                 280                 285

Thr Tyr Lys Asp Gly Arg Pro Leu Thr Asp Asp Glu Val Ala Gly Met
    290                 295                 300

Leu Ile Gly Leu Leu Ala Gly Gln His Thr Ser Ser Thr Thr Ser
305                 310                 315                 320

Ala Trp Met Gly Phe Phe Leu Ala Arg Asp Lys Thr Leu Gln Lys Lys
                325                 330                 335

Cys Tyr Leu Glu Gln Lys Thr Val Cys Gly Glu Asn Leu Pro Pro Leu
            340                 345                 350

Thr Tyr Asp Gln Leu Lys Asp Leu Asn Leu Leu Asp Arg Cys Ile Lys
        355                 360                 365

Glu Thr Leu Arg Leu Arg Pro Pro Ile Met Ile Met Met Arg Met Ala
    370                 375                 380

Arg Thr Pro Gln Thr Val Ala Gly Tyr Thr Ile Pro Pro Gly His Gln
385                 390                 395                 400

Val Cys Val Ser Pro Thr Val Asn Gln Arg Leu Lys Asp Ser Trp Val
                405                 410                 415

Glu Arg Leu Asp Phe Asn Pro Asp Arg Tyr Leu Gln Asp Asn Pro Ala
            420                 425                 430

Ser Gly Glu Lys Phe Ala Tyr Val Pro Phe Gly Ala Gly Arg His Arg
        435                 440                 445

Cys Ile Gly Glu Asn Phe Ala Tyr Val Gln Ile Lys Thr Ile Trp Ser
    450                 455                 460

Thr Met Leu Arg Leu Tyr Glu Phe Asp Leu Ile Asp Gly Tyr Phe Pro
465                 470                 475                 480

Thr Val Asn Tyr Thr Thr Met Ile His Thr Pro Glu Asn Pro Val Ile
                485                 490                 495

Arg Tyr Lys Arg Arg Ser Lys
            500

<210> SEQ ID NO 155
<211> LENGTH: 503
<212> TYPE: PRT
<213> ORGANISM: Rattus sp.

<400> SEQUENCE: 155

Met Val Leu Leu Gly Leu Leu Gln Ser Gly Gly Ser Val Leu Gly Gln
1               5                   10                  15

Ala Met Glu Gln Val Thr Gly Gly Asn Leu Leu Ser Thr Leu Leu Ile
            20                  25                  30
```

```
Ala Cys Ala Phe Thr Leu Ser Leu Val Tyr Leu Phe Arg Leu Ala Val
         35                  40                  45

Gly His Met Val Gln Leu Pro Ala Gly Ala Lys Ser Pro Pro Tyr Ile
 50                  55                  60

Tyr Ser Pro Ile Pro Phe Leu Gly His Ala Ile Ala Phe Gly Lys Ser
 65                  70                  75                  80

Pro Ile Glu Phe Leu Glu Asn Ala Tyr Glu Lys Tyr Gly Pro Val Phe
                     85                  90                  95

Ser Phe Thr Met Val Gly Lys Thr Phe Thr Tyr Leu Leu Gly Ser Asp
                100                 105                 110

Ala Ala Ala Leu Leu Phe Asn Ser Lys Asn Glu Asp Leu Asn Ala Glu
                115                 120                 125

Glu Val Tyr Gly Arg Leu Thr Thr Pro Val Phe Gly Lys Gly Val Ala
        130                 135                 140

Tyr Asp Val Pro Asn Ala Val Phe Leu Glu Gln Lys Lys Ile Leu Lys
145                 150                 155                 160

Ser Gly Leu Asn Ile Ala His Phe Lys Gln Tyr Val Ser Ile Glu
                165                 170                 175

Lys Glu Ala Lys Glu Tyr Phe Lys Ser Trp Gly Glu Ser Gly Glu Arg
            180                 185                 190

Asn Val Phe Glu Ala Leu Ser Glu Leu Ile Ile Leu Thr Ala Ser His
        195                 200                 205

Cys Leu His Gly Lys Glu Ile Arg Ser Gln Leu Asn Glu Lys Val Ala
210                 215                 220

Gln Leu Tyr Ala Asp Leu Asp Gly Gly Phe Ser His Ala Ala Trp Leu
225                 230                 235                 240

Leu Pro Gly Trp Leu Pro Leu Pro Ser Phe Arg Arg Arg Asp Arg Ala
                245                 250                 255

His Arg Glu Ile Lys Asn Ile Phe Tyr Lys Ala Ile Gln Lys Arg Arg
                260                 265                 270

Leu Ser Lys Glu Pro Ala Glu Asp Ile Leu Gln Thr Leu Leu Asp Ser
            275                 280                 285

Thr Tyr Lys Asp Gly Arg Pro Leu Thr Asp Glu Ile Ala Gly Met
290                 295                 300

Leu Ile Gly Leu Leu Leu Ala Gly Gln His Thr Ser Ser Thr Thr Ser
305                 310                 315                 320

Ala Trp Met Gly Phe Phe Leu Ala Arg Asp Lys Pro Leu Gln Asp Lys
                325                 330                 335

Cys Tyr Leu Glu Gln Lys Thr Val Cys Gly Glu Asp Leu Pro Pro Leu
            340                 345                 350

Thr Tyr Glu Gln Leu Lys Asp Leu Asn Leu Leu Asp Arg Cys Ile Lys
            355                 360                 365

Glu Thr Leu Arg Leu Arg Pro Pro Ile Met Thr Met Met Arg Met Ala
370                 375                 380

Lys Thr Pro Gln Thr Val Ala Gly Tyr Thr Ile Pro Pro Gly His Gln
385                 390                 395                 400

Val Cys Val Ser Pro Thr Val Asn Gln Arg Leu Lys Asp Ser Trp Val
                405                 410                 415

Glu Arg Leu Asp Phe Asn Pro Asp Arg Tyr Leu Gln Asp Asn Pro Ala
            420                 425                 430

Ser Gly Glu Lys Phe Ala Tyr Val Pro Phe Gly Ala Gly Arg His Arg
            435                 440                 445

Cys Ile Gly Glu Asn Phe Ala Tyr Val Gln Ile Lys Thr Ile Trp Ser
450                 455                 460
```

```
Thr Met Leu Arg Leu Tyr Glu Phe Asp Leu Ile Asn Gly Tyr Phe Pro
465                 470                 475                 480

Ser Val Asn Tyr Thr Thr Met Ile His Thr Pro Glu Asn Pro Val Ile
                485                 490                 495

Arg Tyr Lys Arg Arg Ser Lys
                500
```

<210> SEQ ID NO 156
<211> LENGTH: 515
<212> TYPE: PRT
<213> ORGANISM: Aspergillus fumigatus

<400> SEQUENCE: 156

```
Met Val Pro Met Leu Trp Leu Thr Ala Tyr Met Ala Val Ala Val Leu
1               5                   10                  15

Thr Ala Ile Leu Leu Asn Val Val Tyr Gln Leu Phe Phe Arg Leu Trp
                20                  25                  30

Asn Arg Thr Glu Pro Pro Met Val Phe His Trp Val Pro Phe Leu Gly
            35                  40                  45

Ser Thr Ile Ser Tyr Gly Ile Asp Pro Tyr Lys Phe Phe Phe Ala Cys
50                  55                  60

Arg Glu Lys Tyr Gly Asp Ile Phe Thr Phe Ile Leu Leu Gly Gln Lys
65                  70                  75                  80

Thr Thr Val Tyr Leu Gly Val Gln Gly Asn Glu Phe Ile Leu Asn Gly
                85                  90                  95

Lys Leu Lys Asp Val Asn Ala Glu Glu Val Tyr Ser Pro Leu Thr Thr
                100                 105                 110

Pro Val Phe Gly Ser Asp Val Val Tyr Asp Cys Pro Asn Ser Lys Leu
            115                 120                 125

Met Glu Gln Lys Lys Phe Ile Lys Tyr Gly Leu Thr Gln Ser Ala Leu
130                 135                 140

Glu Ser His Val Pro Leu Ile Glu Lys Glu Val Leu Asp Tyr Leu Arg
145                 150                 155                 160

Asp Ser Pro Asn Phe Gln Gly Ser Ser Gly Arg Met Asp Ile Ser Ala
                165                 170                 175

Ala Met Ala Glu Ile Thr Ile Phe Thr Ala Ala Arg Ala Leu Gln Gly
            180                 185                 190

Gln Glu Val Arg Ser Lys Leu Thr Ala Glu Phe Ala Asp Leu Tyr His
        195                 200                 205

Asp Leu Asp Lys Gly Phe Thr Pro Ile Asn Phe Met Leu Pro Trp Ala
210                 215                 220

Pro Leu Pro His Asn Lys Lys Arg Asp Ala Ala His Ala Arg Met Arg
225                 230                 235                 240

Ser Ile Tyr Val Asp Ile Ile Asn Gln Arg Arg Leu Asp Gly Asp Lys
                245                 250                 255

Asp Ser Gln Lys Ser Asp Met Ile Trp Asn Leu Met Asn Cys Thr Tyr
            260                 265                 270

Lys Asn Gly Gln Gln Val Pro Asp Lys Glu Ile Ala His Met Met Ile
        275                 280                 285

Thr Leu Leu Met Ala Gly Gln His Ser Ser Ser Ser Ile Ser Ala Trp
290                 295                 300

Ile Met Leu Arg Leu Ala Ser Gln Pro Lys Val Leu Glu Glu Leu Tyr
305                 310                 315                 320

Gln Glu Gln Leu Ala Asn Leu Gly Pro Ala Gly Pro Asp Gly Ser Leu
                325                 330                 335
```

```
Pro Pro Leu Gln Tyr Lys Asp Leu Asp Lys Leu Pro Phe His Gln His
            340                 345                 350

Val Ile Arg Glu Thr Leu Arg Ile His Ser Ser Ile His Ser Ile Met
            355                 360                 365

Arg Lys Val Lys Ser Pro Leu Pro Val Pro Gly Thr Pro Tyr Met Ile
370                 375                 380

Pro Pro Gly Arg Val Leu Leu Ala Ser Pro Gly Val Thr Ala Leu Ser
385                 390                 395                 400

Asp Glu His Phe Pro Asn Ala Gly Cys Trp Asp Pro His Arg Trp Glu
            405                 410                 415

Asn Gln Ala Thr Lys Glu Gln Glu Asn Asp Glu Val Val Asp Tyr Gly
            420                 425                 430

Tyr Gly Ala Val Ser Lys Gly Thr Ser Ser Pro Tyr Leu Pro Phe Gly
            435                 440                 445

Ala Gly Arg His Arg Cys Ile Gly Glu Lys Phe Ala Tyr Val Asn Leu
        450                 455                 460

Gly Val Ile Leu Ala Thr Ile Val Arg His Leu Arg Leu Phe Asn Val
465                 470                 475                 480

Asp Gly Lys Lys Gly Val Pro Glu Thr Asp Tyr Ser Ser Leu Phe Ser
            485                 490                 495

Gly Pro Met Lys Pro Ser Ile Ile Gly Trp Glu Lys Arg Ser Lys Asn
            500                 505                 510

Thr Ser Lys
        515

<210> SEQ ID NO 157
<211> LENGTH: 516
<212> TYPE: PRT
<213> ORGANISM: Penicillium digitatum

<400> SEQUENCE: 157

Met Asp Leu Val Pro Leu Val Thr Gly Gln Ile Lys Cys Ile Ala Tyr
1               5                   10                  15

Tyr Thr Thr Gly Leu Val Leu Ala Ser Ile Val Leu Asn Val Ile Lys
            20                  25                  30

Gln Leu Val Phe Tyr Asn Arg Lys Glu Pro Pro Val Val Phe His Trp
        35                  40                  45

Ile Pro Phe Ile Gly Ser Thr Val Ala Tyr Gly Met Asp Pro Tyr Gln
    50                  55                  60

Phe Phe Phe Ala Ser Arg Ala Lys Tyr Gly Asn Ile Phe Thr Phe Ile
65                  70                  75                  80

Leu Leu Gly Lys Lys Thr Thr Val Tyr Leu Gly Val Glu Gly Asn Glu
            85                  90                  95

Phe Ile Leu Asn Gly Lys Leu Lys Asp Val Asn Ala Glu Glu Ile Tyr
            100                 105                 110

Gly Lys Leu Thr Thr Pro Val Phe Gly Ser Asp Val Val Tyr Asp Cys
        115                 120                 125

Pro Asn Ser Lys Leu Met Glu Gln Lys Phe Ile Lys Tyr Gly Leu
    130                 135                 140

Ser Gln Glu Ala Leu Glu Ser Tyr Val Pro Leu Ile Ala Asp Glu Ile
145                 150                 155                 160

Ser Ser Tyr Ile Lys Ser Ser Pro Ser Phe Lys Gly Gln Ser Gly Thr
            165                 170                 175

Ile Asp Leu Val Pro Ala Met Ala Glu Ile Thr Thr Phe Thr Ala Ala
            180                 185                 190
```

```
Arg Thr Leu Gln Gly Glu Glu Val Arg Ser Lys Leu Thr Thr Glu Phe
            195                 200                 205

Ala Lys Leu Phe His Asp Leu Asp Leu Gly Phe Thr Pro Ile Asn Phe
    210                 215                 220

Met Leu Pro Trp Ala Pro Leu Pro Gln Asn Arg Lys Arg Asp Arg Ala
225                 230                 235                 240

His Arg Arg Met Arg Glu Ile Tyr Val Asp Ile Ile Gln Ala Arg Arg
                245                 250                 255

Glu Ala Gly Glu Glu Ala Asn Asp Asn Gly Arg Asp Lys Thr Lys Gly
            260                 265                 270

Thr Asp Met Ile Ser Asn Leu Met Arg Cys Val Tyr Arg Asp Gly Thr
        275                 280                 285

Pro Ile Pro Asp Lys Glu Ile Ala His Leu Met Ile Thr Leu Leu Met
        290                 295                 300

Ala Gly Gln His Ser Ser Ala Ser Ile Ser Cys Trp Ile Leu Leu Arg
305                 310                 315                 320

Leu Ala Ser Gln Pro Glu Met Thr Glu Lys Leu Phe Ala Glu Gln Val
                325                 330                 335

Asn Asn Leu Gly Ala Asp Leu Pro Pro Leu Gln Tyr Lys Asp Leu Asp
            340                 345                 350

Lys Leu Pro Leu His Arg Asn Val Ile Lys Glu Thr Leu Arg Leu His
        355                 360                 365

Ser Ser Ile His Thr Leu Met Arg Lys Val Lys Asn Pro Met Pro Val
    370                 375                 380

Pro Gly Thr Asp Phe Val Ile Pro Pro Ser His Thr Leu Leu Ser Ser
385                 390                 395                 400

Pro Gly Val Thr Ala Arg Asp Glu Arg His Phe Arg Asp Pro Leu Arg
                405                 410                 415

Trp Asp Pro His Arg Trp Glu Ser Arg Val Glu Ala Glu Asp Ser Ser
            420                 425                 430

Asp Thr Val Asp Tyr Gly Tyr Gly Ala Val Ser Lys Gly Thr Arg Ser
        435                 440                 445

Pro Tyr Leu Pro Phe Gly Ala Gly Arg His Arg Cys Ile Gly Glu Lys
    450                 455                 460

Phe Ala Tyr Leu Asn Leu Gly Val Ile Ile Ala Thr Leu Val Arg Glu
465                 470                 475                 480

Phe Arg Phe Phe Asn Pro Glu Gly Met Glu Gly Val Pro Asp Thr Asp
                485                 490                 495

Tyr Ser Ser Leu Phe Ser Arg Pro Met Gln Pro Ala Thr Val Arg Trp
            500                 505                 510

Glu Val Arg Ser
        515

<210> SEQ ID NO 158
<211> LENGTH: 522
<212> TYPE: PRT
<213> ORGANISM: Monilinia fructicola

<400> SEQUENCE: 158

Met Gly Val Leu Glu Thr Ile Ala Gly Pro Leu Ala Gln Glu Ile Ser
1               5                   10                  15

Gln Arg Ser Thr Gly Thr Ile Ile Ala Ala Gly Val Ala Ala Phe Val
            20                  25                  30

Val Leu Ala Val Val Leu Asn Val Leu Asn Gln Val Leu Phe Ala Asn
        35                  40                  45
```

-continued

Pro Asn Glu Pro Pro Val Val Phe His Trp Leu Pro Ile Ile Gly Ser
    50                  55                  60

Thr Ile Thr Tyr Gly Ile Asp Pro Tyr Arg Phe Phe Asp Cys Arg
65                  70                  75                  80

Ala Lys Tyr Gly Asp Val Phe Thr Phe Ile Leu Leu Gly Lys Lys Thr
                    85                  90                  95

Thr Val Tyr Leu Gly Arg Lys Gly Asn Asp Phe Ile Leu Asn Gly Lys
                100                 105                 110

His Lys Asp Leu Asn Ala Glu Glu Ile Tyr Thr Val Leu Thr Thr Pro
            115                 120                 125

Val Phe Gly Lys Asp Val Val Tyr Asp Cys Pro Asn Ala Lys Leu Met
        130                 135                 140

Glu Gln Lys Lys Phe Met Lys Ile Gly Leu Ser Thr Glu Ala Phe Arg
145                 150                 155                 160

Ser Tyr Val Pro Ile Ile Gln Met Glu Val Glu Asn Phe Met Lys Arg
                165                 170                 175

Ser Ser Ala Phe Lys Gly Gln Lys Gly Thr Ala Asn Ile Pro Pro Ala
                180                 185                 190

Met Ala Glu Ile Thr Ile Tyr Thr Ala Ser His Thr Leu Gln Gly Lys
            195                 200                 205

Glu Val Arg Asp Arg Phe Asp Thr Ser Phe Ala Ser Leu Tyr His Asp
        210                 215                 220

Leu Asp Met Gly Phe Ser Pro Ile Asn Phe Met Leu His Trp Ala Pro
225                 230                 235                 240

Leu Pro His Asn Arg Ala Arg Asp His Ala Gln Arg Thr Val Ala Ser
                245                 250                 255

Thr Tyr Met Asp Ile Ile Gln Lys Arg Arg Ala Gln Ala Thr Glu Ala
                260                 265                 270

Glu Phe Lys Ser Asp Ile Met Trp Gln Leu Met Arg Ser Ser Tyr Lys
            275                 280                 285

Asp Gly Thr Pro Val Pro Asp Lys Glu Ile Ala Asn Met Met Ile Ala
        290                 295                 300

Leu Leu Met Ala Gly Gln His Ser Ser Ser Ser Ile Ser Trp Ile
305                 310                 315                 320

Met Leu Arg Leu Ala Ala Arg Pro Asp Ile Met Glu Glu Leu Tyr Gln
                325                 330                 335

Glu Gln Ile Glu Val Leu Gly Ala Asp Leu Pro Asp Leu Lys Tyr Glu
                340                 345                 350

Asp Leu Ser Lys Leu Thr Leu His Gln Asn Ile Leu Lys Glu Thr Leu
            355                 360                 365

Arg Leu His Thr Pro Ile His Ser Ile Met Arg Lys Val Thr Thr Pro
        370                 375                 380

Met Pro Val Ser Gly Thr Lys Tyr Val Ile Pro Thr Ser His Thr Leu
385                 390                 395                 400

Met Ala Ser Pro Gly Cys Thr Ser Arg Asp Ala Glu Tyr Phe Pro Glu
                405                 410                 415

Pro Leu Glu Trp Asp Pro His Arg Trp Asp Ile Gly Ser Gly Arg Val
                420                 425                 430

Ile Gly Asn Asp Gln Asp Glu Glu Phe Gln Asp Tyr Gly Tyr Gly Met
            435                 440                 445

Ile Ser Lys Gly Ala Ser Ser Pro Tyr Leu Pro Phe Gly Ala Gly Ser
        450                 455                 460

His Arg Cys Ile Gly Glu Gln Phe Ala Asn Val Gln Leu Ile Thr Ile

```
                    465                 470                 475                 480
        Met Ala Thr Val Val Arg Leu Phe Lys Phe Lys Asn Pro Asp Gly Ser
                            485                 490                 495

Lys Asp Val Ile Gly Thr Asp Tyr Thr Ser Leu Phe Thr Gly Pro Leu
                            500                 505                 510

Glu Pro Ala Val Val Ala Trp Glu Arg Arg
                            515                 520

<210> SEQ ID NO 159
<211> LENGTH: 524
<212> TYPE: PRT
<213> ORGANISM: Uncinula necator

<400> SEQUENCE: 159

Met Tyr Ile Ala Asp Ile Leu Ser Asp Leu Leu Thr Gln Gln Thr Thr
        1               5                   10                  15

Arg Tyr Gly Trp Ile Phe Met Val Thr Ser Ile Ala Phe Ser Ile Ile
                        20                  25                  30

Leu Leu Ala Val Gly Leu Asn Val Leu Ser Gln Leu Leu Phe Arg Arg
                    35                  40                  45

Pro Tyr Glu Pro Pro Val Val Phe His Trp Phe Pro Ile Ile Gly Ser
        50                  55                  60

Thr Ile Ser Tyr Gly Ile Asp Pro Tyr Lys Phe Tyr Phe Asp Cys Arg
        65                  70                  75                  80

Ala Lys Tyr Gly Asp Ile Phe Thr Phe Ile Leu Leu Gly Lys Lys Val
                        85                  90                  95

Thr Val Tyr Leu Gly Leu Gln Gly Asn Asn Phe Ile Leu Asn Gly Lys
                        100                 105                 110

Leu Lys Asp Val Asn Ala Glu Glu Ile Tyr Thr Asn Leu Thr Thr Pro
                    115                 120                 125

Val Phe Gly Arg Asp Val Val Tyr Asp Cys Pro Asn Ser Lys Leu Met
                130                 135                 140

Glu Gln Lys Lys Phe Met Lys Thr Ala Leu Thr Ile Glu Ala Phe His
        145                 150                 155                 160

Ser Tyr Val Thr Ile Ile Gln Asn Glu Val Glu Ala Tyr Ile Asn Asn
                        165                 170                 175

Cys Val Ser Phe Gln Gly Glu Ser Gly Thr Val Asn Ile Ser Lys Val
                        180                 185                 190

Met Ala Glu Ile Thr Ile Tyr Thr Ala Ser His Ala Leu Gln Gly Glu
                    195                 200                 205

Glu Val Arg Glu Asn Phe Asp Ser Ser Phe Ala Ala Leu Tyr His Asp
                210                 215                 220

Leu Asp Met Gly Phe Thr Pro Ile Asn Phe Thr Phe Tyr Trp Ala Pro
        225                 230                 235                 240

Leu Pro Trp Asn Arg Ala Arg Asp His Ala Gln Arg Thr Val Ala Arg
                        245                 250                 255

Thr Tyr Met Asn Ile Ile Gln Ala Arg Arg Glu Glu Lys Arg Ser Gly
                        260                 265                 270

Glu Asn Lys His Asp Ile Met Trp Glu Leu Met Arg Ser Thr Tyr Lys
                    275                 280                 285

Asp Gly Thr Pro Val Pro Asp Arg Glu Ile Ala His Met Met Ile Ala
                290                 295                 300

Leu Leu Met Ala Gly Gln His Ser Ser Ser Thr Ser Ser Trp Ile
        305                 310                 315                 320

Met Leu Trp Leu Ala Ala Arg Pro Asp Ile Met Glu Glu Leu Tyr Glu
```

```
            325                 330                 335
Glu Gln Leu Arg Ile Phe Gly Ser Glu Lys Pro Phe Pro Leu Gln
            340                 345                 350

Tyr Glu Asp Leu Ser Lys Leu Gln Leu His Gln Asn Val Leu Lys Glu
        355                 360                 365

Val Leu Arg Leu His Ala Pro Ile His Ser Ile Met Arg Lys Val Lys
    370                 375                 380

Asn Pro Met Ile Val Pro Gly Thr Lys Tyr Val Ile Pro Thr Ser His
385                 390                 395                 400

Val Leu Ile Ser Ser Pro Gly Cys Thr Ser Gln Asp Ala Thr Phe Phe
                405                 410                 415

Pro Asp Pro Leu Lys Trp Asp Pro His Arg Trp Asp Ile Gly Ser Gly
            420                 425                 430

Lys Val Leu Gly Asn Asp Ala Val Asp Glu Lys Tyr Asp Tyr Gly Tyr
        435                 440                 445

Gly Leu Thr Ser Thr Gly Ala Ser Ser Pro Tyr Leu Pro Phe Gly Ala
    450                 455                 460

Gly Arg His Arg Cys Ile Gly Glu Gln Phe Ala Thr Leu Gln Leu Val
465                 470                 475                 480

Thr Ile Met Ala Thr Met Val Arg Phe Phe Arg Phe Arg Asn Ile Asp
                485                 490                 495

Gly Lys Gln Gly Val Val Lys Thr Asp Tyr Ser Ser Leu Phe Ser Met
            500                 505                 510

Pro Leu Ala Pro Ala Leu Ile Gly Trp Glu Lys Arg
        515                 520

<210> SEQ ID NO 160
<211> LENGTH: 540
<212> TYPE: PRT
<213> ORGANISM: Mycosphaerella graminicola

<400> SEQUENCE: 160

Met Gly Leu Leu Gln Glu Val Leu Ala Gln Phe Asp Ala Gln Phe Gly
1               5                   10                  15

Gln Thr Ser Leu Trp Lys Leu Val Gly Leu Gly Phe Leu Ala Phe Ser
            20                  25                  30

Thr Leu Ala Ile Leu Leu Asn Val Leu Ser Gln Leu Leu Phe Arg Gly
        35                  40                  45

Lys Leu Ser Asp Pro Pro Leu Val Phe His Trp Val Pro Phe Ile Gly
    50                  55                  60

Ser Thr Ile Thr Tyr Gly Ile Asp Pro Tyr Lys Phe Phe Phe Ser Cys
65                  70                  75                  80

Arg Glu Lys Tyr Gly Asp Val Phe Thr Phe Ile Leu Leu Gly Lys Lys
                85                  90                  95

Thr Thr Val Cys Leu Gly Thr Lys Gly Asn Asp Phe Ile Leu Asn Gly
            100                 105                 110

Lys Leu Lys Asp Val Asn Ala Glu Glu Ile Tyr Ser Pro Leu Thr Thr
        115                 120                 125

Pro Val Phe Gly Lys Asp Val Val Tyr Asp Cys Pro Asn Ser Lys Leu
    130                 135                 140

Met Glu Gln Lys Lys Phe Val Lys Tyr Gly Leu Thr Thr Ser Ala Leu
145                 150                 155                 160

Gln Ser Tyr Val Thr Leu Ile Ala Ala Glu Thr Arg Gln Phe Phe Asp
                165                 170                 175

Arg Asn Asn Pro His Lys Lys Phe Ala Ser Thr Ser Gly Thr Ile Asp
```

```
                    180                 185                 190
Leu Pro Pro Ala Leu Ala Glu Leu Thr Ile Tyr Thr Ala Ser Arg Ser
            195                 200                 205

Leu Gln Gly Lys Glu Val Arg Glu Gly Phe Asp Ser Ser Phe Ala Asp
        210                 215                 220

Leu Tyr His Tyr Leu Asp Met Gly Phe Thr Pro Ile Asn Phe Met Leu
225                 230                 235                 240

Pro Trp Ala Pro Leu Pro Gln Asn Arg Arg Asp Tyr Ala Gln Lys
                    245                 250                 255

Lys Met Ser Glu Thr His Met Ser Ile Ile Gln Lys Arg Arg Glu Ser
                260                 265                 270

Lys Arg Ala Asn Met Arg Lys Thr Thr Ser Arg Cys Lys Tyr Lys Asp
            275                 280                 285

Gly Asn Ala Ile Pro Asp Lys Glu Ile Ala His Met Met Ile Ala Leu
        290                 295                 300

Leu Met Ala Gly Gln His Ser Ser Ser Ala Thr Glu Ser Trp Ile Thr
305                 310                 315                 320

Leu Arg Leu Ala Ser Arg Pro Asp Ile Gln Asp Glu Leu Leu Gln Glu
                    325                 330                 335

Gln Lys Asp Met Leu Gly Val Asn Ala Asp Gly Ser Ile Lys Glu Leu
                340                 345                 350

Thr Tyr Ala Asn Leu Ser Lys Leu Thr Leu Leu Asn Gln Val Val Lys
            355                 360                 365

Glu Thr Leu Cys Ile His Ala Pro Ile His Ser Ile Leu Arg Lys Val
        370                 375                 380

Lys Ser Pro Met Pro Ile Glu Gly Thr Ala Tyr Ile Ile Pro Thr Thr
385                 390                 395                 400

His Thr Leu Leu Ala Ala Pro Gly Thr Thr Ser Arg Met Asp Glu His
                    405                 410                 415

Phe Pro Asp Cys Leu His Trp Glu Pro His Arg Trp Asp Glu Ser Pro
                420                 425                 430

Ser Glu Lys Tyr Lys His Leu Ser Pro Thr Thr Ala Leu Gly Ser Ile
            435                 440                 445

Ala Glu Glu Lys Glu Asp Tyr Gly Tyr Gly Leu Val Ser Lys Gly Ala
        450                 455                 460

Ala Ser Pro Tyr Leu Pro Phe Gly Ala Gly Arg His Arg Cys Ile Gly
465                 470                 475                 480

Glu Gln Phe Ala Tyr Val Gln Leu Gln Thr Ile Thr Ala Thr Met Val
                    485                 490                 495

Arg Asp Phe Lys Phe Tyr Asn Val Asp Gly Ser Asp Asn Val Val Gly
                500                 505                 510

Thr Asp Tyr Ser Ser Leu Phe Ser Arg Pro Leu Ser Pro Ala Val Val
            515                 520                 525

Lys Trp Glu Arg Arg Glu Glu Lys Glu Glu Lys Asn
        530                 535                 540

<210> SEQ ID NO 161
<211> LENGTH: 526
<212> TYPE: PRT
<213> ORGANISM: Venturia nashicola

<400> SEQUENCE: 161

Met Gly Leu Leu Ser Ala Leu Leu Ala Pro Leu Ala Gly Ser Asp Arg
1               5                   10                  15

Gly Trp Leu Phe Tyr Thr Leu Ala Ser Phe Gly Phe Thr Val Ala Ile
```

```
                    20                  25                  30
Val Val Ala Asn Val Leu Lys Gln Val Leu Leu Lys Asn Pro Asn Glu
            35                  40                  45

Pro Pro Val Val Phe His Trp Phe Pro Phe Phe Gly Asn Thr Val Val
        50                  55                  60

Tyr Gly Ile Asp Pro Ile Lys Phe Phe Ala Glu Cys Lys Glu Lys His
65                  70                  75                  80

Gly Asp Ile Phe Thr Phe Ile Leu Leu Gly Arg Lys Thr Thr Val Tyr
                    85                  90                  95

Ile Gly Thr Lys Gly Tyr Glu Phe Ile Leu Asn Gly Lys Gln Ser His
            100                 105                 110

Val Asn Ala Glu Glu Ile Tyr Ser Pro Leu Thr Thr Pro Val Phe Gly
        115                 120                 125

Ser Asp Val Val Tyr Asp Cys Pro Asn Ser Lys Leu Met Glu Gln Lys
        130                 135                 140

Lys Phe Val Lys Tyr Gly Leu Thr Thr Glu Ala Leu Lys Ser Tyr Val
145                 150                 155                 160

Thr Leu Ile Gln Arg Glu Val Glu Asp Tyr Ala Lys Arg Tyr Ser Gln
                    165                 170                 175

Phe Lys Gly Glu Lys Gly Ser Phe Asp Val Cys Ala Thr Met Gly Glu
                    180                 185                 190

Ile Thr Ile Phe Thr Ala Ser Arg Ser Leu Gln Gly Lys Glu Val Arg
            195                 200                 205

Asp Lys Phe Asp Ala Ser Phe Ala Asp Leu Phe His Asp Leu Asp Met
        210                 215                 220

Gly Phe Ser Pro Ile Asn Phe Met Leu Pro Trp Ala Pro Leu Pro His
225                 230                 235                 240

Asn Arg Arg Arg Asp Ala Ala Asn Lys Lys Met Thr Glu Thr Tyr Leu
                    245                 250                 255

Glu Ile Ile Arg Ser Arg Lys Val Glu Gly Ala Lys Lys Asp Ser Glu
                    260                 265                 270

Asp Met Ile Trp Asn Leu Met Gln Cys Val Tyr Lys Asn Gly Thr Pro
            275                 280                 285

Ile Pro Asp Asn Glu Ile Ala His Met Met Ile Ala Leu Leu Met Ala
        290                 295                 300

Gly Gln His Ser Ser Ser Ser Thr Ser Ser Trp Met Leu Phe Arg Leu
305                 310                 315                 320

Ala Thr Arg Pro Asp Ile Gln Glu Glu Leu Tyr Gln Glu Gln Ile Arg
                    325                 330                 335

Val Cys Gly Ala Asp Leu Pro Pro Leu Lys Tyr Asp Asp Leu Ala Arg
                    340                 345                 350

Met Pro Leu His Asn Gln Gln Ile Ile Lys Glu Thr Leu Arg Met His
            355                 360                 365

Ser Pro Ile His Ser Ile Leu Arg Ala Val Lys Gln Pro Met Pro Ile
        370                 375                 380

Glu Gly Thr Pro Tyr Thr Ile Pro Thr Ser His Val Leu Leu Ala Ala
385                 390                 395                 400

Pro Ile Ala Ser Gly Gly Ser Pro Met Tyr Phe Pro Ala Pro Glu Lys
                    405                 410                 415

Trp Glu Pro His Arg Trp Asp Glu Gly Ser Gly Thr Asn Ile Ser
                    420                 425                 430

Gly Gly Asp Asn Gly Asp Glu Glu Lys Glu Asp Tyr Gly Tyr Gly Leu
            435                 440                 445
```

```
Ile Thr Lys Gly Ala Ser Ser Pro Tyr Leu Pro Phe Gly Ala Gly Arg
    450                 455                 460

His Arg Cys Ile Gly Glu Gln Phe Ala Tyr Met Gln Leu Asn Thr Val
465                 470                 475                 480

Leu Ala Thr Gln Val Arg Glu Phe Lys Phe Ser Phe Arg Glu Gly Glu
                    485                 490                 495

Ser Phe Pro Lys Thr Asp Phe Ser Ser Leu Phe Ser Gly Pro Gln Arg
                500                 505                 510

Pro Ala Trp Leu Asn Trp Glu Arg Arg Glu Lys Ser Ser Ser
            515                 520                 525

<210> SEQ ID NO 162
<211> LENGTH: 495
<212> TYPE: PRT
<213> ORGANISM: Schizosaccharomyces pombe

<400> SEQUENCE: 162

Met Ala Phe Ser Leu Val Ser Ile Leu Ser Ile Ala Leu Ala Trp
1               5                   10                  15

Tyr Val Gly Tyr Ile Ile Asn Gln Leu Thr Ser Arg Asn Ser Lys Arg
                20                  25                  30

Pro Pro Ile Val Phe His Trp Ile Pro Phe Val Gly Ser Ala Val Ala
                35                  40                  45

Tyr Gly Met Asp Pro Tyr Val Phe Phe Arg Glu Cys Arg Ala Lys Tyr
        50                  55                  60

Gly Asp Val Phe Thr Phe Val Cys Met Gly Arg Lys Met Thr Ala Phe
65                  70                  75                  80

Leu Gly Val Gln Gly Asn Asp Phe Leu Phe Asn Gly Lys Leu Ala Asp
                85                  90                  95

Leu Asn Ala Glu Glu Ala Tyr Ser His Leu Thr Thr Pro Val Phe Gly
                100                 105                 110

Lys Asp Val Val Tyr Asp Ile Pro Asn His Val Phe Met Glu His Lys
                115                 120                 125

Lys Phe Ile Lys Ser Gly Leu Gly Phe Ser Gln Phe Arg Ser Tyr Val
    130                 135                 140

Pro Leu Ile Leu Asn Glu Met Asp Ala Phe Leu Ser Thr Ser Pro Asp
145                 150                 155                 160

Phe Gly Pro Gly Lys Glu Gly Val Ala Asp Leu Leu Lys Thr Met Pro
                165                 170                 175

Val Met Thr Ile Tyr Thr Ala Ser Arg Thr Leu Gln Gly Ala Glu Val
                180                 185                 190

Arg Lys Gly Phe Asp Ala Gly Phe Ala Asp Leu Tyr His Asp Leu Asp
    195                 200                 205

Gln Gly Phe Ser Pro Val Asn Phe Val Phe Pro Trp Leu Pro Leu Pro
    210                 215                 220

Arg Asn Arg Arg Arg Asp Arg Ala His Lys Ile Met Gln Lys Thr Tyr
225                 230                 235                 240

Leu Lys Ile Ile Lys Asp Arg Arg Ser Ser Thr Glu Asn Pro Gly Thr
                245                 250                 255

Asp Met Ile Trp Thr Leu Met Ser Cys Lys Tyr Arg Asp Gly Arg Pro
                260                 265                 270

Leu Lys Glu His Glu Ile Ala Gly Met Met Ile Ala Leu Leu Met Ala
    275                 280                 285

Gly Gln His Thr Ser Ala Ala Thr Ile Val Trp Val Leu Ala Leu Leu
    290                 295                 300
```

```
Gly Ser Lys Pro Glu Ile Ile Glu Met Leu Trp Glu Glu Gln Lys Arg
305                 310                 315                 320

Val Val Gly Glu Asn Leu Glu Leu Lys Phe Asp Gln Tyr Lys Asp Met
                325                 330                 335

Pro Leu Leu Asn Tyr Val Ile Gln Glu Thr Leu Arg Leu His Pro Pro
            340                 345                 350

Ile His Ser His Met Arg Lys Val Lys Arg Asp Leu Pro Val Pro Gly
        355                 360                 365

Ser Lys Ile Val Ile Pro Ala Asn Asn Tyr Leu Leu Ala Ala Pro Gly
370                 375                 380

Leu Thr Ala Thr Glu Glu Glu Tyr Phe Thr His Ala Thr Asp Phe Asp
385                 390                 395                 400

Pro Lys Arg Trp Asn Asp Arg Val Asn Glu Asp Glu Asn Ala Glu Gln
            405                 410                 415

Ile Asp Tyr Gly Tyr Gly Leu Val Thr Lys Gly Ala Ala Ser Pro Tyr
        420                 425                 430

Leu Pro Phe Gly Ala Gly Arg His Arg Cys Ile Gly Glu Gln Phe Ala
    435                 440                 445

Tyr Met His Leu Ser Thr Ile Ile Ser Lys Phe Val His Asp Tyr Thr
450                 455                 460

Trp Thr Leu Ile Gly Lys Val Pro Asn Val Asp Tyr Ser Ser Met Val
465                 470                 475                 480

Ala Leu Pro Leu Gly Pro Val Lys Ile Ala Trp Lys Arg Arg Asn
            485                 490                 495

<210> SEQ ID NO 163
<211> LENGTH: 528
<212> TYPE: PRT
<213> ORGANISM: Candida albicans

<400> SEQUENCE: 163

Met Ala Ile Val Glu Thr Val Ile Asp Gly Ile Asn Tyr Phe Leu Ser
1               5                   10                  15

Leu Ser Val Thr Gln Gln Ile Ser Ile Leu Leu Gly Val Pro Phe Val
                20                  25                  30

Tyr Asn Leu Val Trp Gln Tyr Leu Tyr Ser Leu Arg Lys Asp Arg Ala
            35                  40                  45

Pro Leu Val Phe Tyr Trp Ile Pro Trp Phe Gly Ser Ala Ala Ser Tyr
    50                  55                  60

Gly Gln Gln Pro Tyr Glu Phe Phe Glu Ser Cys Arg Gln Lys Tyr Gly
65                  70                  75                  80

Asp Val Phe Ser Phe Met Leu Leu Gly Lys Ile Met Thr Val Tyr Leu
                85                  90                  95

Gly Pro Lys Gly His Glu Phe Val Phe Asn Ala Lys Leu Ser Asp Val
            100                 105                 110

Ser Ala Glu Asp Ala Tyr Lys His Leu Thr Thr Pro Val Phe Gly Lys
        115                 120                 125

Gly Val Ile Tyr Asp Cys Pro Asn Ser Arg Leu Met Glu Gln Lys Lys
    130                 135                 140

Phe Ala Lys Phe Ala Leu Thr Thr Asp Ser Phe Lys Arg Tyr Val Pro
145                 150                 155                 160

Lys Ile Arg Glu Glu Ile Leu Asn Tyr Phe Val Thr Asp Glu Ser Phe
                165                 170                 175

Lys Leu Lys Glu Lys Thr His Gly Val Ala Asn Val Met Lys Thr Gln
            180                 185                 190
```

```
Pro Glu Ile Thr Ile Phe Thr Ala Ser Arg Ser Leu Phe Gly Asp Glu
        195                 200                 205

Met Arg Arg Ile Phe Asp Arg Ser Phe Ala Gln Leu Tyr Ser Asp Leu
    210                 215                 220

Asp Lys Gly Phe Thr Pro Ile Asn Phe Val Phe Pro Asn Leu Pro Leu
225                 230                 235                 240

Pro His Tyr Trp Arg Arg Asp Ala Ala Gln Lys Lys Ile Ser Ala Thr
                245                 250                 255

Tyr Met Lys Glu Ile Lys Ser Arg Arg Glu Arg Gly Asp Ile Asp Pro
            260                 265                 270

Asn Arg Asp Leu Ile Asp Ser Leu Leu Ile His Ser Thr Tyr Lys Asp
        275                 280                 285

Gly Val Lys Met Thr Asp Gln Glu Ile Ala Asn Leu Leu Ile Gly Ile
    290                 295                 300

Leu Met Gly Gly Gln His Thr Ser Ala Ser Thr Ser Ala Trp Phe Leu
305                 310                 315                 320

Leu His Leu Gly Glu Lys Pro His Leu Gln Asp Val Ile Tyr Gln Glu
                325                 330                 335

Val Val Glu Leu Leu Lys Glu Lys Gly Gly Asp Leu Asn Asp Leu Thr
            340                 345                 350

Tyr Glu Asp Leu Gln Lys Leu Pro Ser Val Asn Asn Thr Ile Lys Glu
        355                 360                 365

Thr Leu Arg Met His Met Pro Leu His Ser Ile Phe Arg Lys Val Thr
370                 375                 380

Asn Pro Leu Arg Ile Pro Glu Thr Asn Tyr Ile Val Pro Lys Gly His
385                 390                 395                 400

Tyr Val Leu Val Ser Pro Gly Tyr Ala His Thr Ser Glu Arg Tyr Phe
                405                 410                 415

Asp Asn Pro Glu Asp Phe Asp Pro Thr Arg Trp Asp Thr Ala Ala Ala
            420                 425                 430

Lys Ala Asn Ser Val Ser Phe Asn Ser Ser Asp Glu Val Asp Tyr Gly
        435                 440                 445

Phe Gly Lys Val Ser Lys Gly Val Ser Ser Pro Tyr Leu Pro Phe Gly
    450                 455                 460

Gly Gly Arg His Arg Cys Ile Gly Glu Gln Phe Ala Tyr Val Gln Leu
465                 470                 475                 480

Gly Thr Ile Leu Thr Thr Phe Val Tyr Asn Leu Arg Trp Thr Ile Asp
                485                 490                 495

Gly Tyr Lys Val Pro Asp Pro Asp Tyr Ser Ser Met Val Val Leu Pro
            500                 505                 510

Thr Glu Pro Ala Glu Ile Ile Trp Glu Lys Arg Glu Thr Cys Met Phe
        515                 520                 525

<210> SEQ ID NO 164
<211> LENGTH: 533
<212> TYPE: PRT
<213> ORGANISM: Candida glabrata

<400> SEQUENCE: 164

Met Ser Thr Glu Asn Thr Ser Leu Val Val Glu Leu Leu Glu Tyr Val
1               5                   10                  15

Lys Leu Gly Leu Ser Tyr Phe Gln Ala Leu Pro Leu Ala Gln Arg Val
            20                  25                  30

Ser Ile Met Val Ala Leu Pro Phe Val Tyr Thr Ile Thr Trp Gln Leu
        35                  40                  45
```

```
Leu Tyr Ser Leu Arg Lys Asp Arg Pro Pro Leu Val Phe Tyr Trp Ile
 50                  55                  60

Pro Trp Val Gly Ser Ala Ile Pro Tyr Gly Thr Lys Pro Tyr Glu Phe
 65                  70                  75                  80

Phe Glu Asp Cys Gln Lys Lys Tyr Gly Asp Ile Phe Ser Phe Met Leu
                 85                  90                  95

Leu Gly Arg Ile Met Thr Val Tyr Leu Gly Pro Lys Gly His Glu Phe
            100                 105                 110

Ile Phe Asn Ala Lys Leu Ala Asp Val Ser Ala Glu Ala Ala Tyr Ser
            115                 120                 125

His Leu Thr Thr Pro Val Phe Gly Lys Gly Val Ile Tyr Asp Cys Pro
130                 135                 140

Asn His Arg Leu Met Glu Gln Lys Lys Phe Val Lys Gly Ala Leu Thr
145                 150                 155                 160

Lys Glu Ala Phe Val Arg Tyr Val Pro Leu Ile Ala Glu Glu Ile Tyr
                165                 170                 175

Lys Tyr Phe Arg Asn Ser Lys Asn Phe Lys Ile Asn Glu Asn Asn Ser
            180                 185                 190

Gly Ile Val Asp Val Met Val Ser Gln Pro Glu Met Thr Ile Phe Thr
            195                 200                 205

Ala Ser Arg Ser Leu Leu Gly Lys Glu Met Arg Asp Lys Leu Asp Thr
210                 215                 220

Asp Phe Ala Tyr Leu Tyr Ser Asp Leu Asp Lys Gly Phe Thr Pro Ile
225                 230                 235                 240

Asn Phe Val Phe Pro Asn Leu Pro Leu Glu His Tyr Arg Lys Arg Asp
                245                 250                 255

His Ala Gln Gln Ala Ile Ser Gly Thr Tyr Met Ser Leu Ile Lys Glu
            260                 265                 270

Arg Arg Glu Lys Asn Asp Ile Gln Asn Arg Asp Leu Ile Asp Glu Leu
            275                 280                 285

Met Lys Asn Ser Thr Tyr Lys Asp Gly Thr Lys Met Thr Asp Gln Glu
290                 295                 300

Ile Ala Asn Leu Leu Ile Gly Val Leu Met Gly Gly Gln His Thr Ser
305                 310                 315                 320

Ala Ala Thr Ser Ala Trp Cys Leu Leu His Leu Ala Glu Arg Pro Asp
                325                 330                 335

Val Gln Glu Glu Leu Tyr Gln Glu Gln Met Arg Val Leu Asn Asn Asp
            340                 345                 350

Thr Lys Glu Leu Thr Tyr Asp Asp Leu Gln Asn Met Pro Leu Leu Asn
            355                 360                 365

Gln Met Ile Lys Glu Thr Leu Arg Leu His His Pro Leu His Ser Leu
370                 375                 380

Phe Arg Lys Val Met Arg Asp Val Ala Ile Pro Asn Thr Ser Tyr Val
385                 390                 395                 400

Val Pro Arg Asp Tyr His Val Leu Val Ser Pro Gly Tyr Thr His Leu
                405                 410                 415

Gln Glu Glu Phe Phe Pro Lys Pro Asn Glu Phe Asn Ile His Arg Trp
            420                 425                 430

Asp Gly Asp Ala Ala Ser Ser Ala Ala Gly Gly Asp Glu Val Asp
            435                 440                 445

Tyr Gly Phe Gly Ala Ile Ser Lys Gly Val Ser Ser Pro Tyr Leu Pro
450                 455                 460

Phe Gly Gly Gly Arg His Arg Cys Ile Gly Glu Leu Phe Ala Tyr Cys
465                 470                 475                 480
```

```
Gln Leu Gly Val Leu Met Ser Ile Phe Ile Arg Thr Met Lys Trp Arg
                485                 490                 495

Tyr Pro Thr Glu Gly Glu Thr Val Pro Pro Ser Asp Phe Thr Ser Met
            500                 505                 510

Val Thr Leu Pro Thr Ala Pro Ala Lys Ile Tyr Trp Glu Lys Arg His
        515                 520                 525

Pro Glu Gln Lys Tyr
        530

<210> SEQ ID NO 165
<211> LENGTH: 529
<212> TYPE: PRT
<213> ORGANISM: Ashbya gossypii

<400> SEQUENCE: 165

Met Ser Glu Ser Leu Leu Gln Thr Val Val Ala Tyr Val Glu Leu Val
1               5                   10                  15

Leu His His Phe Met Ala Leu Ser Trp Thr Gln Leu Ser Ile Val
            20                  25                  30

Ile Val Ala Pro Phe Ile Tyr Ser Leu Val Trp Gln Thr Leu Tyr Ser
            35                  40                  45

Phe Arg Lys Asp Arg Val Pro Leu Val Pro Phe Met Val Pro Trp Val
50                  55                  60

Gly Ser Ala Leu Ala Tyr Gly Arg Ala Pro Tyr Glu Phe Phe Gly Lys
65                  70                  75                  80

Cys Gln Gln Lys Tyr Gly Asp Val Phe Ala Phe Met Leu Leu Gly Arg
                85                  90                  95

Val Met Thr Val Tyr Leu Gly Thr Lys Gly His Glu Phe Ile Leu Asn
            100                 105                 110

Ala Lys Leu Ala Glu Val Ser Ala Glu Glu Ala Tyr Thr Lys Leu Thr
            115                 120                 125

Thr Pro Val Phe Gly Glu Gly Val Val Tyr Asp Cys Pro Asn His Arg
        130                 135                 140

Leu Met Glu Gln Lys Lys Phe Cys Lys Asn Ala Leu Ser Thr Glu Ala
145                 150                 155                 160

Phe Arg Arg Tyr Val Pro Met Val Met Asp Glu Val Arg Lys Tyr Leu
                165                 170                 175

Arg Thr Ser Lys His Phe Met Met Asn Glu Arg Ser Ser Gly Val Val
            180                 185                 190

Asn Val Met Glu Thr Gln Pro Glu Met Thr Ile Phe Thr Ala Ser Arg
            195                 200                 205

Ser Leu Leu Gly Ala Glu Met His Ser Met Leu Asp Ala Asp Phe Ala
        210                 215                 220

Tyr Leu Tyr Ala Asp Leu Asp Lys Gly Phe Thr Pro Leu Asn Phe Val
225                 230                 235                 240

Phe Arg Asp Leu Pro Leu Asp Asn Tyr Arg Arg Asp Asn Ala Gln
                245                 250                 255

Arg Thr Ile Ser Ser Thr Tyr Met Lys Val Ile Glu Arg Arg Lys
            260                 265                 270

Asn Asn Asp Val Gln Asp Arg Asp Leu Ile Asp Ala Leu Met Thr Ser
            275                 280                 285

Ala Gln Tyr Lys Asp Gly Val Lys Met Thr Asp Gln Gln Ile Ala Asn
        290                 295                 300

Leu Leu Ile Gly Val Leu Met Gly Gly Gln His Thr Ser Ala Ala Thr
305                 310                 315                 320
```

```
Ser Ala Trp Val Leu Leu His Leu Ala Glu Arg Pro Asp Ile Gln Glu
                325                 330                 335

Glu Leu Tyr Glu Glu Gln Met Arg Val Leu Asp Gly Gly Ala Lys Glu
            340                 345                 350

Leu Thr Tyr Glu Leu Leu Gln Glu Met Pro Leu Leu Asn Gln Val Ile
        355                 360                 365

Lys Glu Thr Leu Arg Met His His Pro Leu His Ser Leu Phe Arg Lys
    370                 375                 380

Val Thr Arg Asp Met Pro Val Pro Asn Thr Ser Tyr Val Ile Pro Lys
385                 390                 395                 400

Asp His Tyr Val Leu Ala Ser Pro Gly Phe Cys His Leu Ser Glu Glu
                405                 410                 415

Tyr Phe Pro Asn Ala Lys Glu Phe Asn Pro His Arg Trp Asp Asn Asp
            420                 425                 430

Ala Ala Ser Ser Val Ser Thr Gly Glu Lys Val Asp Tyr Gly Phe Gly
        435                 440                 445

Ala Ile Ser Lys Gly Val Ser Ser Pro Tyr Leu Pro Phe Gly Gly Gly
    450                 455                 460

Arg His Arg Cys Ile Gly Glu Gly Phe Ala Tyr Met Gln Leu Gly Thr
465                 470                 475                 480

Ile Phe Ser Val Val Arg Ser Met Lys Trp His Phe Pro Ala Asp
                485                 490                 495

Met Lys Gly Val Pro Asn Pro Asp Phe Thr Ser Met Val Thr Leu Pro
            500                 505                 510

Ser Glu Pro Cys Arg Ile Ala Trp Glu Arg Arg Val Pro Asp Gln Ile
        515                 520                 525

Ile

<210> SEQ ID NO 166
<211> LENGTH: 550
<212> TYPE: PRT
<213> ORGANISM: Filobasidiella neoformans

<400> SEQUENCE: 166

Met Ser Ala Ile Ile Pro Gln Val Gln Gln Leu Leu Gly Gln Val Ala
1               5                   10                  15

Gln Phe Phe Pro Pro Trp Phe Ala Ala Leu Pro Thr Ser Leu Lys Val
            20                  25                  30

Ala Ile Ala Val Val Gly Ile Pro Ala Leu Ile Ile Gly Leu Asn Val
        35                  40                  45

Phe Gln Gln Leu Cys Leu Pro Arg Arg Lys Asp Leu Pro Pro Val Val
    50                  55                  60

Phe His Tyr Ile Pro Trp Phe Gly Ser Ala Ala Tyr Tyr Gly Glu Asp
65                  70                  75                  80

Pro Tyr Lys Phe Leu Phe Glu Cys Arg Asp Lys Tyr Gly Asp Leu Phe
                85                  90                  95

Thr Phe Ile Leu Met Gly Arg Arg Ile Thr Val Ala Leu Gly Pro Lys
            100                 105                 110

Gly Asn Asn Leu Ser Leu Gly Gly Lys Ile Ser Gln Val Ser Ala Glu
        115                 120                 125

Glu Ala Tyr Thr His Leu Thr Thr Pro Val Phe Gly Lys Gly Val Val
    130                 135                 140

Tyr Asp Cys Pro Asn Glu Met Leu Met Gln Gln Lys Lys Phe Ile Lys
145                 150                 155                 160
```

```
Ser Gly Leu Thr Thr Glu Ser Leu Gln Ser Tyr Pro Pro Met Ile Thr
            165                 170                 175

Ser Glu Cys Glu Asp Phe Phe Thr Lys Glu Val Gly Ile Ser Pro Gln
        180                 185                 190

Lys Pro Ser Ala Thr Leu Asp Leu Leu Lys Ala Met Ser Glu Leu Ile
    195                 200                 205

Ile Leu Thr Ala Ser Arg Thr Leu Gln Gly Lys Glu Val Arg Glu Ser
210                 215                 220

Leu Asn Gly Gln Phe Ala Lys Tyr Tyr Glu Asp Leu Asp Gly Gly Phe
225                 230                 235                 240

Thr Pro Leu Asn Phe Met Phe Pro Asn Leu Pro Leu Pro Ser Tyr Lys
                245                 250                 255

Arg Arg Asp Glu Ala Gln Lys Ala Met Ser Asp Phe Tyr Leu Lys Ile
            260                 265                 270

Met Glu Asn Arg Arg Lys Gly Glu Ser Asp His Glu His Asp Met Ile
        275                 280                 285

Glu Asn Leu Gln Ser Cys Lys Tyr Arg Asn Gly Val Pro Leu Ser Asp
    290                 295                 300

Arg Asp Ile Ala His Ile Met Ile Ala Leu Leu Met Ala Gly Gln His
305                 310                 315                 320

Thr Ser Ser Ala Thr Ser Ser Trp Thr Leu Leu His Leu Ala Asp Arg
                325                 330                 335

Pro Asp Val Val Glu Ala Leu Tyr Gln Glu Gln Lys Gln Lys Leu Gly
            340                 345                 350

Asn Pro Asp Gly Thr Phe Arg Asp Tyr Arg Tyr Glu Asp Leu Lys Glu
        355                 360                 365

Leu Pro Ile Met Asp Ser Ile Ile Arg Glu Thr Leu Arg Met His Ala
    370                 375                 380

Pro Ile His Ser Ile Tyr Arg Lys Val Leu Ser Asp Ile Pro Val Pro
385                 390                 395                 400

Pro Ser Leu Ser Ala Pro Ser Glu Asn Gly Gln Tyr Ile Ile Pro Lys
                405                 410                 415

Gly His Tyr Ile Met Ala Ala Pro Gly Val Ser Gln Met Asp Pro Arg
            420                 425                 430

Ile Trp Gln Asp Ala Lys Val Trp Asn Pro Ala Arg Trp His Asp Glu
        435                 440                 445

Lys Gly Phe Ala Ala Ala Met Val Gln Tyr Thr Lys Ala Glu Gln
    450                 455                 460

Val Asp Tyr Gly Phe Gly Ser Val Ser Lys Gly Thr Glu Ser Pro Tyr
465                 470                 475                 480

Gln Pro Phe Gly Ala Gly Arg His Arg Cys Val Gly Glu Gln Phe Ala
                485                 490                 495

Tyr Thr Gln Leu Ser Thr Ile Phe Thr Tyr Val Val Arg Asn Phe Thr
            500                 505                 510

Leu Lys Leu Ala Val Pro Lys Phe Pro Glu Thr Asn Tyr Arg Thr Met
        515                 520                 525

Ile Val Gln Pro Asn Asn Pro Leu Val Thr Phe Thr Leu Arg Asn Ala
    530                 535                 540

Glu Val Lys Gln Glu Val
545                 550

<210> SEQ ID NO 167
<211> LENGTH: 561
<212> TYPE: PRT
<213> ORGANISM: Ustilago maydis
```

<400> SEQUENCE: 167

```
Met Val Ala Ser Ser Ser Ala Thr Ala Ser Leu Leu Asp Gln Leu
1               5                   10                  15

Phe Ala Leu Thr Pro Leu Ala Asp Ser Ser Ala Trp Ile Lys Thr Ile
                20                  25                  30

Thr Val Leu Val Leu Leu Pro Leu Leu Ala Val Val Leu Asn Val Ala
                35                  40                  45

Ser Gln Leu Leu Leu Ala Thr Pro Lys Asn His Pro Pro Val Val Phe
        50                  55                  60

His Phe Val Pro Val Ile Gly Ser Ala Ile Tyr Tyr Gly Ile Asp Pro
65                  70                  75                  80

Tyr Lys Phe Phe Phe Glu Cys Arg Glu Lys Tyr Gly Asp Val Phe Thr
                85                  90                  95

Phe Val Leu Leu Gly Arg Lys Ile Thr Val Ala Leu Gly Pro Lys Gly
                100                 105                 110

Ser Asn Leu Val Phe Asn Ala Lys His Gln Gln Val Thr Ala Glu Asp
            115                 120                 125

Ala Tyr Thr His Leu Thr Thr Pro Val Phe Gly Lys Glu Val Val Tyr
    130                 135                 140

Asp Val Pro Asn Ala Val Phe Met Glu Gln Lys Lys Phe Val Lys Val
145                 150                 155                 160

Gly Leu Ser Ile Glu Asn Phe Arg Val Tyr Val Pro Gln Ile Val Asp
                165                 170                 175

Glu Val Arg Glu Tyr Ile Lys Ser Asp Ala Arg Phe Ser Ala Leu Lys
                180                 185                 190

Thr Arg Lys Thr Ile Thr Val Asp Ile Phe Gln Ala Met Ser Glu Leu
                195                 200                 205

Ile Ile Leu Thr Ala Ser Arg Thr Leu Gln Gly Lys Glu Val Arg Gln
        210                 215                 220

Gly Leu Asp Lys Ser Phe Ala Gln Leu Tyr His Asp Leu Asp Ser Gly
225                 230                 235                 240

Phe Thr Pro Ile Asn Phe Val Ile Pro Asn Leu Pro Leu Pro Ser Asn
                245                 250                 255

Phe Lys Arg Asp Arg Ala Gln Lys Lys Met Ser Gln Phe Tyr Gln Asp
                260                 265                 270

Ile Val Ala Lys Arg Arg Ala Ala Gly Ala Ser Thr Ser Ala Asp Asp
                275                 280                 285

Ala Ser Gly Glu Asn Asp Met Ile Ala Ala Leu Ile Glu Gln Lys Tyr
        290                 295                 300

Lys Asn Gly Arg Ala Leu Ser Gly Val Glu Ile Ala His Met Met Ile
305                 310                 315                 320

Ala Leu Leu Met Ala Gly Gln His Thr Ser Ser Ala Thr Ser Ser Trp
                325                 330                 335

Ala Phe Leu Arg Leu Ala Ser Arg Pro Glu Ile Ile Glu Glu Leu Tyr
                340                 345                 350

Glu Glu Gln Leu Asn Val Tyr Ser Asp Gly His Gly Gly Leu Arg Glu
            355                 360                 365

Leu Asp Tyr Glu Thr Gln Lys Thr Ser Val Pro Leu Leu Asp Ala Val
    370                 375                 380

Val Lys Glu Thr Leu Arg Leu His Pro Pro Leu His Ser Ile Met Arg
385                 390                 395                 400

Tyr Val Lys Ser Asp Leu Ala Val Pro Pro Thr Leu Ser Ser Pro Thr
                405                 410                 415
```

```
Ser Thr Lys Ser Glu Pro Asp Ala His Tyr Val Ile Pro Lys Gly His
            420                 425                 430

Tyr Ile Met Ala Ala Pro Gly Val Ser Gln Val Asp Pro Gln Ile Trp
        435                 440                 445

Lys Ser Ser Asp Gln Phe Asp Pro His Arg Trp Leu Asp Ala Thr Thr
450                 455                 460

Ala Ala Ala Met Gln Asp Ser Gly Glu Asp Lys Gln Asp Phe Gly Phe
465                 470                 475                 480

Gly Met Ile Ser Thr Gly Ala Asn Ser Pro Tyr Leu Pro Phe Gly Ala
                485                 490                 495

Gly Arg His Arg Cys Ile Gly Glu Gln Phe Ala Tyr Leu Gln Ile Gly
                500                 505                 510

Val Ile Leu Ala Thr Phe Val Arg Ile Phe Lys Trp His Leu Asp Ser
            515                 520                 525

Lys Phe Pro Asp Pro Asp Tyr Gln Ser Met Val Leu Pro Ser Lys
530                 535                 540

Asn Gly Cys Ala Ile Val Leu Thr Pro Arg Ala Glu Ser Leu His Leu
545                 550                 555                 560

Asp
```

<210> SEQ ID NO 168
<211> LENGTH: 495
<212> TYPE: PRT
<213> ORGANISM: Chlamydomonas reinhardtii

<400> SEQUENCE: 168

```
Met Asp Leu Pro Pro Glu Leu Ala Val Leu Ala Asp Lys Val Leu Ser
1               5                   10                  15

Leu Ser Pro Val Val Leu Val Ala Leu Gly Ser Ala Val Leu Ile Leu
                20                  25                  30

Ala Leu Ala Val Gly Arg Val Leu Phe Asn Leu Pro Ser Lys Arg
            35                  40                  45

Pro Pro Val Trp Glu Gly Leu Pro Phe Ile Gly Gly Leu Leu Lys Phe
        50                  55                  60

Thr Gly Gly Pro Trp Lys Leu Leu Glu Asn Gly Tyr Ala Lys Phe Gly
65                  70                  75                  80

Glu Cys Phe Thr Val Pro Val Ala His Arg Arg Val Thr Phe Leu Ile
                85                  90                  95

Gly Pro Gly Val Ser Pro His Phe Lys Ala Gly Asp Asp Glu Met
            100                 105                 110

Ser Gln Ser Glu Val Tyr Asp Phe Asn Ile Pro Thr Phe Gly Arg Gly
        115                 120                 125

Val Val Phe Asp Val Glu Gln Lys Val Arg Thr Glu Gln Phe Arg Met
130                 135                 140

Phe Thr Glu Ala Leu Thr Lys Asn Arg Leu Lys Ser Tyr Val Pro His
145                 150                 155                 160

Phe Asn Lys Glu Ala Glu Glu Tyr Phe Ala Lys Trp Gly Glu Thr Gly
                165                 170                 175

Val Val Asp Phe Lys Asp Glu Phe Ser Lys Leu Ile Thr Leu Thr Ala
            180                 185                 190

Ala Arg Thr Leu Leu Gly Arg Glu Val Arg Glu Gln Leu Phe Asp Glu
        195                 200                 205

Val Ala Asp Leu Leu His Gly Leu Asp Glu Gly Met Val Pro Leu Ser
    210                 215                 220
```

```
Val Phe Phe Pro Tyr Ala Pro Ile Pro Val His Phe Lys Arg Asp Arg
225                 230                 235                 240

Cys Arg Lys Asp Leu Ala Ala Ile Phe Ala Lys Ile Ile Arg Ala Arg
            245                 250                 255

Arg Glu Ser Gly Arg Arg Glu Glu Asp Val Leu Gln Gln Phe Ile Asp
        260                 265                 270

Ala Arg Tyr Gln Asn Val Asn Gly Gly Arg Ala Leu Thr Glu Glu Glu
    275                 280                 285

Ile Thr Gly Leu Leu Ile Ala Val Leu Phe Ala Gly Gln His Thr Ser
290                 295                 300

Ser Ile Thr Thr Ser Trp Thr Gly Ile Phe Met Ala Ala Asn Lys Glu
305                 310                 315                 320

His Tyr Asn Lys Ala Ala Glu Glu Gln Gln Asp Ile Ile Arg Lys Phe
                325                 330                 335

Gly Asn Glu Leu Ser Phe Glu Thr Leu Ser Glu Met Glu Val Leu His
            340                 345                 350

Arg Asn Ile Thr Glu Ala Leu Arg Met His Pro Pro Leu Leu Leu Val
        355                 360                 365

Met Arg Tyr Ala Lys Lys Pro Phe Ser Val Thr Thr Ser Thr Gly Lys
370                 375                 380

Ser Tyr Val Ile Pro Lys Gly Asp Val Val Ala Ala Ser Pro Asn Phe
385                 390                 395                 400

Ser His Met Leu Pro Gln Cys Phe Asn Asn Pro Lys Ala Tyr Asp Pro
                405                 410                 415

Asp Arg Phe Ala Pro Pro Arg Glu Glu Gln Asn Lys Pro Tyr Ala Phe
            420                 425                 430

Ile Gly Phe Gly Ala Gly Arg His Ala Cys Ile Gly Gln Asn Phe Ala
        435                 440                 445

Tyr Leu Gln Ile Lys Ser Ile Trp Ser Val Leu Leu Arg Asn Phe Glu
450                 455                 460

Phe Glu Leu Leu Asp Pro Val Pro Glu Ala Asp Tyr Glu Ser Met Val
465                 470                 475                 480

Ile Gly Pro Lys Pro Cys Arg Val Arg Tyr Thr Arg Arg Lys Leu
                485                 490                 495

<210> SEQ ID NO 169
<211> LENGTH: 486
<212> TYPE: PRT
<213> ORGANISM: Lycopersicon esculentum

<400> SEQUENCE: 169

Met Glu Leu Gly Asp Asn Lys Ile Leu Asn Val Gly Leu Leu Leu Val
1               5                   10                  15

Ala Thr Leu Leu Val Ala Lys Leu Ile Ser Ala Leu Ile Met Pro Arg
            20                  25                  30

Ser Lys Lys Arg Leu Pro Pro Val Val Lys Ala Trp Pro Ile Val Gly
        35                  40                  45

Gly Leu Ile Arg Phe Leu Lys Gly Pro Val Val Met Leu Arg Gln Glu
    50                  55                  60

Tyr Pro Lys Leu Gly Ser Val Phe Thr Leu Asn Leu Leu Asn Lys Asn
65                  70                  75                  80

Ile Thr Phe Phe Ile Gly Pro Glu Val Ser Ala His Phe Phe Lys Ala
                85                  90                  95

Pro Glu Thr Asp Leu Ser Gln Gln Glu Val Tyr Gln Phe Asn Val Pro
            100                 105                 110
```

```
Thr Phe Gly Pro Gly Val Val Phe Asp Val Asp Tyr Thr Ile Arg Gln
        115                 120                 125

Glu Gln Phe Arg Phe Thr Glu Ala Leu Arg Val Thr Lys Leu Lys
    130                 135                 140

Gly Tyr Val Asp Gln Met Val Thr Glu Ala Glu Tyr Phe Ser Lys
145                 150                 155                 160

Trp Gly Ser Gly Glu Val Asp Leu Lys Tyr Glu Leu His Leu
                165                 170                 175

Ile Ile Leu Thr Ala Ser Arg Cys Leu Leu Gly Glu Val Arg Asn
                180                 185                 190

Lys Leu Phe Asp Asp Val Ser Ala Leu Phe His Asp Leu Asp Asn Gly
        195                 200                 205

Met Leu Pro Ile Ser Val Ile Phe Pro Tyr Leu Pro Ile Pro Ala His
        210                 215                 220

Arg Arg Arg Asp Asn Ala Arg Lys Leu Ala Glu Ile Phe Ala Asn
225                 230                 235                 240

Ile Ile Asn Ser Arg Lys Arg Thr Gly Lys Ala Glu Asn Asp Met Leu
                245                 250                 255

Gln Cys Phe Ile Asp Ser Lys Tyr Lys Asp Gly Arg Pro Thr Thr Glu
        260                 265                 270

Gly Glu Ile Thr Gly Leu Leu Ile Ala Ala Leu Phe Ala Gly Gln His
        275                 280                 285

Thr Ser Ser Ile Thr Ser Thr Trp Thr Gly Ser Tyr Leu Leu Thr Asn
290                 295                 300

Asp Lys Tyr Met Ser Ala Val Val Asp Glu Gln Lys Asn Leu Met Lys
305                 310                 315                 320

Asn Thr Gly Met Val Asp His Asp Ile Leu Ser Glu Met Glu Val Leu
                325                 330                 335

Tyr Arg Cys Ile Lys Glu Ala Leu Arg Leu His Pro Pro Leu Ile Met
            340                 345                 350

Leu Leu Arg Ser Ser His Ser Glu Phe Ser Val Thr Thr Arg Glu Gly
        355                 360                 365

Lys Glu Tyr Asp Ile Pro Lys Gly His Ile Val Ala Thr Ser Pro Ala
    370                 375                 380

Phe Ala Asn Arg Leu Pro His Ile Phe Lys Asn Pro Asp Thr Tyr Asp
385                 390                 395                 400

Pro Asp Arg Phe Gly Pro Gly Arg Glu Glu Asp Lys Ala Ala Gly Ala
                405                 410                 415

Phe Ser Tyr Ile Ser Phe Gly Gly Arg His Gly Cys Leu Gly Glu
                420                 425                 430

Pro Phe Ala Tyr Leu Gln Ile Lys Ala Ile Trp Ser His Leu Leu Arg
        435                 440                 445

Asn Phe Glu Phe Glu Leu Ile Ser Pro Phe Pro Glu Ile Asp Trp Asn
    450                 455                 460

Ala Met Val Val Gly Val Lys Gly Glu Val Met Val Lys Tyr Lys Arg
465                 470                 475                 480

Arg Lys Leu Ser Val Glu
                485

<210> SEQ ID NO 170
<211> LENGTH: 488
<212> TYPE: PRT
<213> ORGANISM: Populus sp.

<400> SEQUENCE: 170
```

```
Met Thr Lys Asp Thr Asp Asn Lys Phe Leu Asn Val Gly Leu Leu Ile
1               5                   10                  15
Leu Ala Thr Leu Leu Val Ala Lys Leu Ile Ser Ala Leu Ile Met Pro
            20                  25                  30
Arg Ser Gln Lys Arg Leu Pro Pro Val Met Lys Gly Trp Pro Leu Ile
        35                  40                  45
Gly Gly Leu Ile Arg Phe Leu Lys Gly Pro Ile Val Met Leu Arg Glu
    50                  55                  60
Glu Tyr Pro Lys Leu Gly Ser Val Phe Thr Val Asn Leu Ala Asn Trp
65                  70                  75                  80
Lys Ile Thr Phe Leu Ile Gly Pro Glu Val Ser Ala His Phe Phe Lys
                85                  90                  95
Ala Ser Glu Ala Asp Leu Ser Gln Gln Glu Val Tyr Gln Phe Asn Val
            100                 105                 110
Pro Thr Phe Gly Pro Gly Val Val Phe Asp Val Asp Tyr Ser Ile Arg
        115                 120                 125
Gln Glu Gln Phe Arg Phe Phe Thr Glu Ala Leu Arg Val Ser Lys Leu
    130                 135                 140
Lys Gly Tyr Val Asp Gln Met Val Val Glu Thr Glu Gly Tyr Phe Ser
145                 150                 155                 160
Lys Trp Gly Asp Ser Gly Val Val Asp Ile Lys Tyr Glu Leu Glu His
                165                 170                 175
Leu Ile Ile Leu Thr Ala Ser Arg Cys Leu Leu Gly Arg Glu Val Arg
            180                 185                 190
Asp Lys Leu Phe Asp Asp Val Ser Ala Leu Phe His Asp Leu Asp Asn
        195                 200                 205
Gly Met Leu Pro Ile Ser Val Leu Phe Pro Tyr Leu Pro Ile Pro Ala
    210                 215                 220
His Arg Arg Arg Asp Arg Ala Arg Lys Lys Leu Ala Glu Ile Phe Ala
225                 230                 235                 240
Ser Ile Ile Asn Ser Arg Lys Leu Ala Gly Lys Ser Glu Asn Asp Met
                245                 250                 255
Leu Gln Cys Phe Ile Asp Ser Lys Tyr Lys Asp Gly Arg Pro Thr Thr
            260                 265                 270
Glu Ser Glu Ile Thr Gly Leu Leu Ile Ala Ala Leu Phe Ala Gly Gln
        275                 280                 285
His Thr Ser Ser Ile Thr Ser Thr Trp Thr Gly Ala Tyr Leu Leu Arg
    290                 295                 300
His Asn Glu Tyr Leu Ser Ala Val Leu Glu Glu Gln Lys Ile Leu Met
305                 310                 315                 320
Lys Lys His Gly Asn Lys Val Asp Gln Asp Ile Leu Ser Glu Met Asp
                325                 330                 335
Val Leu His Arg Cys Ile Lys Glu Ala Leu Arg Leu His Pro Pro Leu
            340                 345                 350
Ile Met Leu Leu Arg Ser Ser His Ser Asp Phe Ser Val Thr Thr Arg
        355                 360                 365
Asp Gly Lys Glu Tyr Asp Ile Pro Lys Gly His Ile Val Ala Thr Ser
    370                 375                 380
Pro Ala Phe Ala Asn Arg Leu Pro His Val Phe Lys Asp Pro Glu Arg
385                 390                 395                 400
Tyr Asp Pro Asp Arg Phe Ala Ala Gly Arg Glu Glu Asp Lys Ala Ala
                405                 410                 415
Gly Ala Phe Ser Tyr Ile Ser Phe Gly Gly Gly Arg His Gly Cys Leu
            420                 425                 430
```

```
Gly Glu Pro Phe Ala Tyr Leu Gln Ile Lys Ala Ile Trp Ser His Leu
        435                 440                 445

Leu Arg Asn Phe Glu Phe Glu Leu Ile Ser Pro Phe Pro Glu Thr Asp
    450                 455                 460

Trp Asn Ala Met Val Val Gly Val Lys Asp Lys Val Met Val Arg Tyr
465                 470                 475                 480

Lys Arg Arg Glu Leu Ser Val Asn
                485

<210> SEQ ID NO 171
<211> LENGTH: 496
<212> TYPE: PRT
<213> ORGANISM: Aquilegia sp.

<400> SEQUENCE: 171

Met Asp Met Glu Asn Thr Thr Gln Met Thr Asp Leu Lys Glu Asn Lys
1               5                   10                  15

Phe Leu Asn Val Gly Leu Leu Ile Leu Ala Thr Leu Val Ile Ala Lys
            20                  25                  30

Leu Leu Ser Ala Leu Leu Ile Pro Gln Ser Lys Lys Arg Leu Pro Pro
        35                  40                  45

Thr Val Thr Ala Trp Pro Val Leu Gly Gly Leu Leu Arg Phe Met Lys
    50                  55                  60

Gly Pro Ile Val Met Ile Arg Glu Glu Tyr Pro Lys Leu Gly Ser Val
65                  70                  75                  80

Phe Thr Leu Asn Leu Val Asn Lys Asn Ile Thr Phe Phe Ile Gly Pro
                85                  90                  95

Glu Val Ser Ala His Phe Phe Lys Ala Pro Glu Ser Asp Leu Ser Gln
            100                 105                 110

Gln Glu Val Tyr Gln Phe Asn Val Pro Thr Phe Gly Pro Gly Val Val
        115                 120                 125

Phe Asp Val Asp Tyr Ser Val Arg Gln Glu Gln Phe Arg Phe Phe Thr
    130                 135                 140

Glu Ser Leu Arg Val Thr Lys Leu Lys Gly Tyr Val Asp Gln Met Val
145                 150                 155                 160

Thr Glu Ala Glu Asp Tyr Phe Ala Lys Trp Gly Asp Ser Gly Glu Val
                165                 170                 175

Asp Leu Lys Tyr Glu Leu Glu His Leu Ile Ile Leu Thr Ala Ser Arg
            180                 185                 190

Cys Leu Leu Gly Arg Glu Val Arg Asp Lys Leu Phe Asp Asp Val Ser
        195                 200                 205

Ala Leu Phe His Asp Leu Asp Asn Gly Met Leu Pro Ile Ser Val Ile
    210                 215                 220

Phe Pro Tyr Leu Pro Ile Pro Ala His Arg Arg Asp Arg Ala Arg
225                 230                 235                 240

Lys Lys Leu Ser Glu Ile Phe Ala Asn Ile Ile Ser Ser Arg Glu
                245                 250                 255

Thr Gly Lys Thr Glu Asn Asp Met Leu Gln Cys Phe Ile Asp Ser Lys
            260                 265                 270

Tyr Lys Asp Gly Arg Pro Thr Thr Asp Val Glu Val Thr Gly Leu Leu
        275                 280                 285

Ile Ala Ala Leu Phe Ala Gly Gln His Thr Ser Ser Ile Thr Ser Thr
    290                 295                 300

Trp Thr Gly Ala Tyr Leu Leu Arg His Lys Glu Tyr Leu Ser Ala Val
305                 310                 315                 320
```

Leu Asp Glu Gln Lys Ser Leu Met Lys Met His Gly Ser Thr Ile Asp
                325                 330                 335

His Asp Ile Leu Ser Glu Met Asp Val Leu Tyr Arg Cys Ile Lys Glu
            340                 345                 350

Ala Leu Arg Leu His Pro Pro Leu Ile Met Leu Leu Arg Ser Ser His
        355                 360                 365

Ser Glu Phe Ser Val Thr Thr Arg Glu Gly Lys Glu Tyr Asp Ile Pro
370                 375                 380

Lys Gly His Ile Val Ala Thr Ser Pro Ala Phe Ala Asn Arg Leu Pro
385                 390                 395                 400

His Ile Phe Lys Asp Pro Asp Thr Tyr Asp Pro Asp Arg Phe Ala Ala
                405                 410                 415

Gly Arg Glu Glu Asp Lys Ala Ala Gly Ala Phe Ser Tyr Ile Ser Phe
            420                 425                 430

Gly Gly Gly Arg His Gly Cys Leu Gly Glu Pro Phe Ala Tyr Leu Gln
        435                 440                 445

Ile Lys Ala Ile Trp Ser His Leu Leu Arg Asn Phe Glu Leu Glu Leu
    450                 455                 460

Ile Ser Pro Phe Pro Glu Ile Asp Trp Asn Ala Met Val Val Gly Val
465                 470                 475                 480

Lys Gly Lys Val Met Val Arg Phe Lys Arg Arg Gln Leu Ser Ile Asp
                485                 490                 495

<210> SEQ ID NO 172
<211> LENGTH: 491
<212> TYPE: PRT
<213> ORGANISM: Lotus japonicus

<400> SEQUENCE: 172

Met Glu Ile Ile Asp Gly Gly Gly Asn Lys Phe Leu Asn Thr Val Leu
1               5                   10                  15

Leu Leu Phe Ala Thr Val Ala Val Ala Lys Leu Ile Ile Thr Phe Ile
            20                  25                  30

Ile Pro Lys Pro Lys Lys Asn Leu Pro Pro Ile Leu Gly Gly Phe Pro
        35                  40                  45

Leu Ile Gly Gly Leu Ile Arg Phe Leu Lys Gly Pro Ile Val Met Leu
    50                  55                  60

Arg Glu Glu Tyr Pro Lys Leu Gly Ser Val Phe Thr Val Lys Leu Phe
65                  70                  75                  80

His Trp Asn Val Thr Phe Leu Ile Gly Pro Glu Val Ser Ala His Phe
                85                  90                  95

Phe Lys Ala Ser Glu Ser Asp Leu Ser Gln Gln Glu Val Tyr Gln Phe
            100                 105                 110

Asn Val Pro Thr Phe Gly Pro Gly Val Val Phe Asp Val Asp Tyr Ser
        115                 120                 125

Val Arg Gln Glu Gln Phe Arg Phe Thr Glu Ala Leu Arg Val Asn
    130                 135                 140

Lys Leu Lys Ser Tyr Val Asn Gln Met Val Ala Glu Ala Glu Asp Tyr
145                 150                 155                 160

Phe Ser Lys Trp Gly Ser Ser Gly Glu Val Asp Leu Lys Tyr Glu Leu
                165                 170                 175

Glu His Leu Ile Ile Leu Thr Ala Ser Arg Ser Leu Leu Gly Arg Glu
            180                 185                 190

Val Arg Asp Lys Leu Phe Asp Asp Val Ser Ala Leu Phe His Asp Leu
        195                 200                 205

```
Asp Asn Gly Met Leu Pro Ile Ser Val Leu Phe Pro Tyr Leu Pro Ile
    210                 215                 220

Pro Ala His Lys Arg Arg Asp Gln Ala Arg Lys Lys Leu Ser Glu Ile
225                 230                 235                 240

Phe Glu Lys Ile Ile Val Ser Arg Lys Ser Ala Asn Lys Ser Glu Asp
                245                 250                 255

Asp Met Leu Gln Cys Phe Ile Asp Ser Lys Tyr Lys Asp Gly Arg Pro
            260                 265                 270

Thr Thr Glu Gly Glu Val Thr Gly Leu Leu Ile Ala Ala Leu Phe Ala
        275                 280                 285

Gly Gln His Thr Ser Ser Ile Thr Ser Thr Trp Thr Gly Ala Tyr Leu
    290                 295                 300

Met Cys Asn Asn Lys Tyr Leu Ser Ala Val Val Glu Glu Gln Lys Val
305                 310                 315                 320

Leu Met Glu Lys His Gly Asp Arg Val Asp His Asp Val Leu Ala Glu
                325                 330                 335

Met Asp Val Leu Tyr Arg Cys Ile Lys Glu Ala Leu Arg Leu His Pro
            340                 345                 350

Pro Leu Ile Met Leu Arg Ser Ser His Ser Asp Phe Ser Val Thr
        355                 360                 365

Thr Arg Glu Gly Lys Glu Tyr Asp Ile Pro Lys Gly His Ile Val Ala
    370                 375                 380

Thr Ser Pro Ala Phe Ala Asn Arg Leu Pro His Ile Phe Lys Asp Pro
385                 390                 395                 400

Asp Thr Tyr Asp Pro Asp Arg Phe Ala Val Gly Arg Glu Glu Asp Lys
                405                 410                 415

Ala Ala Gly Ala Phe Ser Tyr Ile Ser Phe Gly Gly Arg His Gly
            420                 425                 430

Cys Leu Gly Glu Pro Phe Ala Tyr Leu Gln Ile Lys Ala Ile Trp Thr
        435                 440                 445

His Leu Leu Arg Asn Phe Glu Leu Glu Leu Val Ser Pro Phe Pro Glu
    450                 455                 460

Ile Asp Trp Asn Ala Met Val Val Gly Val Lys Gly Lys Val Met Val
465                 470                 475                 480

Arg Tyr Lys Arg Arg Val Leu Ser Ala Asn Gln
                485                 490

<210> SEQ ID NO 173
<211> LENGTH: 488
<212> TYPE: PRT
<213> ORGANISM: Arabidopsis thaliana

<400> SEQUENCE: 173

Met Glu Leu Asp Ser Glu Asn Lys Leu Leu Lys Thr Gly Leu Val Ile
1               5                   10                  15

Val Ala Thr Leu Val Ile Ala Lys Leu Ile Phe Ser Phe Phe Thr Ser
                20                  25                  30

Asp Ser Lys Lys Lys Arg Leu Pro Pro Thr Leu Lys Ala Trp Pro Pro
            35                  40                  45

Leu Val Gly Ser Leu Ile Lys Phe Leu Lys Gly Pro Ile Ile Met Leu
        50                  55                  60

Arg Glu Glu Tyr Pro Lys Leu Gly Ser Val Phe Thr Val Asn Leu Val
65                  70                  75                  80

His Lys Lys Ile Thr Phe Leu Ile Gly Pro Glu Val Ser Ala His Phe
                85                  90                  95
```

Phe Lys Ala Ser Glu Ser Asp Leu Ser Gln Gln Glu Val Tyr Gln Phe
            100                 105                 110

Asn Val Pro Thr Phe Gly Pro Gly Val Val Phe Asp Val Asp Tyr Ser
            115                 120                 125

Val Arg Gln Glu Gln Phe Arg Phe Phe Thr Glu Ala Leu Arg Val Asn
        130                 135                 140

Lys Leu Lys Gly Tyr Val Asp Met Met Val Thr Glu Ala Glu Asp Tyr
145                 150                 155                 160

Phe Ser Lys Trp Gly Glu Ser Gly Glu Val Asp Ile Lys Val Glu Leu
                165                 170                 175

Glu Arg Leu Ile Ile Leu Thr Ala Ser Arg Cys Leu Leu Gly Arg Glu
            180                 185                 190

Val Arg Asp Gln Leu Phe Asp Asp Val Ser Ala Leu Phe His Asp Leu
        195                 200                 205

Asp Asn Gly Met Leu Pro Ile Ser Val Leu Phe Pro Tyr Leu Pro Ile
    210                 215                 220

Pro Ala His Arg Arg Arg Asp Arg Ala Arg Glu Lys Leu Ser Glu Ile
225                 230                 235                 240

Phe Ala Lys Ile Ile Gly Ser Arg Lys Arg Ser Gly Lys Thr Glu Asn
                245                 250                 255

Asp Met Leu Gln Cys Phe Ile Glu Ser Lys Tyr Lys Asp Gly Arg Gln
            260                 265                 270

Thr Thr Glu Ser Glu Val Thr Gly Leu Leu Ile Ala Ala Leu Phe Ala
        275                 280                 285

Gly Gln His Thr Ser Ser Ile Thr Ser Thr Trp Thr Gly Ala Tyr Leu
    290                 295                 300

Met Arg Tyr Lys Glu Tyr Phe Ser Ala Ala Leu Asp Glu Gln Lys Asn
305                 310                 315                 320

Leu Ile Ala Lys His Gly Asp Lys Ile Asp His Asp Ile Leu Ser Glu
                325                 330                 335

Met Asp Val Leu Tyr Arg Cys Ile Lys Glu Ala Leu Arg Leu His Pro
            340                 345                 350

Pro Leu Ile Met Leu Met Arg Ala Ser His Ser Asp Phe Ser Val Thr
        355                 360                 365

Ala Arg Asp Gly Lys Thr Tyr Asp Ile Pro Lys Gly His Ile Val Ala
    370                 375                 380

Thr Ser Pro Ala Phe Ala Asn Arg Leu Pro His Ile Phe Lys Asp Pro
385                 390                 395                 400

Asp Thr Tyr Asp Pro Glu Arg Phe Ser Pro Arg Glu Glu Asp Lys
                405                 410                 415

Ala Ala Gly Ala Phe Ser Tyr Ile Ala Phe Gly Gly Gly Arg His Gly
            420                 425                 430

Cys Leu Gly Glu Pro Phe Ala Tyr Leu Gln Ile Lys Ala Ile Trp Ser
        435                 440                 445

His Leu Leu Arg Asn Phe Glu Leu Glu Leu Val Ser Pro Phe Pro Glu
    450                 455                 460

Ile Asp Trp Asn Ala Met Val Val Gly Val Lys Gly Asn Val Met Val
465                 470                 475                 480

Arg Tyr Lys Arg Arg Gln Leu Ser
                485

<210> SEQ ID NO 174
<211> LENGTH: 487
<212> TYPE: PRT

<213> ORGANISM: Pinus sp.

<400> SEQUENCE: 174

```
Met Asp Phe Ile Gln Asn Ile Tyr Val Gln Ala Gly Leu Leu Ile Leu
1               5                   10                  15

Ala Thr Leu Val Leu Ala Lys Ile Val Ser Ser Ile Leu Gly Phe Gly
            20                  25                  30

Ser Ser Lys Asn Leu Pro Pro Met Val Pro Ala Trp Pro Ile Val Gly
        35                  40                  45

Gly Leu Met Lys Phe Leu Lys Gly Pro Ile Val Met Leu Arg Glu Glu
    50                  55                  60

Tyr Pro Lys Leu Gly Asn Val Phe Thr Ile Lys Leu Leu Ile Lys Asn
65                  70                  75                  80

Val Thr Phe Leu Ile Gly Pro Glu Val Ser Gln His Phe Phe Lys Ala
                85                  90                  95

Pro Glu Ser Asp Leu Ser Gln Gln Glu Val Tyr Gln Phe Asn Val Pro
            100                 105                 110

Thr Phe Gly Pro Gly Val Val Phe Asp Val Asp Tyr Ser Val Arg Gln
        115                 120                 125

Glu Gln Phe Arg Phe Phe Thr Glu Ser Leu Arg Val Asn Lys Leu Arg
    130                 135                 140

Ser Tyr Val Asp Gln Met Ile Leu Glu Ala Glu Ser Tyr Phe Ala Asn
145                 150                 155                 160

Trp Gly Glu Glu Gly Val Val Asp Leu Lys Tyr Glu Leu Glu His Leu
                165                 170                 175

Ile Ile Leu Thr Ala Ser Arg Cys Leu Leu Gly Arg Glu Val Arg Asp
            180                 185                 190

Gln Leu Phe Glu Asp Val Ser Ala Leu Phe His Asp Leu Asp Ser Gly
        195                 200                 205

Met Leu Pro Ile Ser Val Val Phe Pro Tyr Leu Pro Ile Pro Ala His
    210                 215                 220

Arg Arg Arg Asp Lys Ala Arg Lys Leu Ala Glu Ile Phe Thr Arg
225                 230                 235                 240

Ile Ile Gln Gly Arg Lys Gln Ser Gly Asn Val Glu Ser Asp Met Leu
                245                 250                 255

Gln Ser Phe Ile Asp Ser Lys Tyr Lys Asp Gly Arg Pro Thr Thr Glu
            260                 265                 270

Ser Glu Val Thr Gly Leu Leu Ile Ala Ala Leu Phe Ala Gly Gln His
        275                 280                 285

Thr Ser Ser Ile Thr Ser Thr Trp Thr Gly Ala Tyr Leu Leu Thr His
    290                 295                 300

Lys Lys Tyr Leu Ser Ala Val Val Glu Glu Gln Lys Asp Val Lys Lys
305                 310                 315                 320

Arg His Gly Asp Lys Leu Asp His Asp Val Leu Ala Glu Met Asp Val
                325                 330                 335

Leu Tyr Arg Cys Ile Lys Glu Ala Leu Arg Leu His Pro Pro Leu Ile
            340                 345                 350

Val Leu Leu Arg Ser Asn His Arg Asp Phe Thr Val Thr Ala Lys Asp
        355                 360                 365

Gly Lys Asp Tyr Val Ile Pro Lys Gly His Val Ala Thr Ser Pro
    370                 375                 380

Ala Phe Ala Asn Arg Leu Pro His Ile Phe Lys Asn Pro Asp Thr Tyr
385                 390                 395                 400

Asp Pro Asp Arg Phe Val Pro Gly Arg Glu Glu Asp Lys Val Gly Gly
```

```
                   405                 410                 415
Ala Phe Ser Tyr Ile Ser Phe Gly Gly Gly Arg His Gly Cys Leu Gly
            420                 425                 430

Glu Pro Phe Ala Tyr Leu Gln Ile Lys Ala Ile Trp Thr His Leu Leu
            435                 440                 445

Arg Asn Phe Glu Leu Glu Leu Ile Ser Pro Phe Pro Glu Ile Asp Trp
            450                 455                 460

Asn Ala Met Val Val Gly Val Lys Asp Lys Val Met Val Arg Tyr Arg
465                 470                 475                 480

Arg Arg Pro Leu Ser Val Asp
                485

<210> SEQ ID NO 175
<211> LENGTH: 490
<212> TYPE: PRT
<213> ORGANISM: Triticum aestivum

<400> SEQUENCE: 175

Met Asp Leu Leu Ala Asp Ala Gln Pro Gln Trp Leu Leu Ala Gly Ala
1               5                   10                  15

Ala Leu Leu Leu Ala Thr Val Ala Phe Leu Arg Ile Leu Leu Gly Pro
                20                  25                  30

Gly Gly Gly Gly Arg Arg Pro Pro Thr Ile Pro Gly Ala Pro Val
            35                  40                  45

Val Gly Gly Leu Leu Arg Phe Leu Arg Gly Pro Ile Pro Leu Ile Arg
        50                  55                  60

Ala Glu Tyr Ala Arg Leu Gly Pro Val Phe Thr Val Pro Ile Leu Thr
65                  70                  75                  80

Arg Arg Ile Thr Phe Leu Ile Gly Pro Asp Val Ser Ala His Phe Phe
                85                  90                  95

Lys Ser Asn Glu Ser Asp Met Ser Gln Gln Glu Val Tyr Arg Phe Asn
            100                 105                 110

Val Pro Thr Phe Gly Pro Gly Val Phe Asp Val Asp Tyr Gln Val
        115                 120                 125

Arg Gln Glu Gln Phe Arg Phe Phe Thr Glu Ala Leu Arg Ala Asn Lys
            130                 135                 140

Leu Arg Ser Tyr Val Asp Gln Met Val Ala Glu Ala Glu Tyr Phe
145                 150                 155                 160

Ser Lys Trp Gly Glu Ser Gly Thr Val Asp Leu Lys Tyr Glu Leu Glu
                165                 170                 175

His Leu Ile Ile Leu Thr Ala Ser Arg Cys Leu Leu Gly Arg Glu Val
            180                 185                 190

Arg Glu Lys Leu Phe Asp Asp Val Ser Ala Leu Phe His Asp Leu Asp
            195                 200                 205

Asn Gly Met Gln Pro Ile Ser Val Ile Phe Pro Tyr Leu Pro Ile Pro
            210                 215                 220

Ala His Arg Arg Asp Gln Ala Arg Thr Arg Leu Ala Glu Ile Phe
225                 230                 235                 240

Ala Thr Ile Ile Lys Ser Arg Lys Ala Ser Gly Gln Ser Glu Glu Asp
                245                 250                 255

Met Leu Gln Cys Phe Ile Asp Ser Lys Tyr Lys Asn Gly Arg Gln Thr
            260                 265                 270

Thr Glu Ser Glu Val Thr Gly Leu Leu Ile Ala Ala Leu Phe Ala Gly
            275                 280                 285

Gln His Thr Ser Ser Ile Thr Ser Thr Trp Thr Gly Ala Tyr Leu Leu
```

```
                290                 295                 300
Lys Phe Gln Gln Tyr Phe Ala Glu Ala Val Glu Glu Gln Lys Glu Val
305                 310                 315                 320

Met Lys Arg His Gly Asp Lys Ile Asp His Asp Ile Leu Ala Glu Met
                325                 330                 335

Asp Val Leu Tyr Arg Cys Ile Lys Glu Ala Leu Arg Leu His Pro Pro
                340                 345                 350

Leu Ile Met Leu Leu Arg Gln Ser His Ser Asp Phe Ser Val Thr Thr
                355                 360                 365

Arg Glu Gly Lys Glu Phe Asp Ile Pro Lys Gly His Ile Val Ala Thr
370                 375                 380

Ser Pro Ala Phe Ala Asn Arg Leu Pro His Ile Phe Lys Asn Pro Asp
385                 390                 395                 400

Ser Tyr Asp Pro Asp Arg Phe Ala Ala Gly Arg Glu Glu Asp Lys Val
                405                 410                 415

Ala Gly Ala Phe Ser Tyr Ile Ser Phe Gly Gly Arg His Gly Cys
                420                 425                 430

Leu Gly Glu Pro Phe Ala Tyr Leu Gln Ile Lys Ala Ile Trp Thr His
                435                 440                 445

Leu Leu Arg Asn Phe Glu Phe Glu Leu Val Ser Pro Phe Pro Glu Asn
450                 455                 460

Asp Trp Asn Ala Met Val Gly Ile Lys Gly Glu Val Met Val Asn
465                 470                 475                 480

Tyr Lys Arg Arg Lys Leu Ile Val Asp Asn
                485                 490

<210> SEQ ID NO 176
<211> LENGTH: 492
<212> TYPE: PRT
<213> ORGANISM: Sorghum bicolor

<400> SEQUENCE: 176

Met Asp Leu Ala Asp Ile Pro Gln Gln Arg Leu Met Ala Gly Leu
1               5                   10                  15

Ala Leu Val Val Ala Thr Val Ile Phe Leu Lys Leu Leu Ser Phe
                20                  25                  30

Arg Ser Gly Gly Gly Lys Lys Arg Leu Pro Pro Thr Ile Pro Gly Ala
                35                  40                  45

Pro Val Val Gly Gly Leu Val Lys Phe Met Arg Gly Pro Ile Pro Met
50                  55                  60

Ile Arg Glu Gln Tyr Ala Ala Leu Gly Ser Val Phe Thr Val Pro Ile
65                  70                  75                  80

Ile Thr Arg Arg Ile Thr Phe Leu Ile Gly Pro Glu Val Ser Ala His
                85                  90                  95

Phe Phe Lys Gly Asn Glu Ala Glu Met Ser Gln Gln Glu Val Tyr Arg
                100                 105                 110

Phe Asn Val Pro Thr Phe Gly Pro Gly Val Val Phe Asp Val Asp Tyr
                115                 120                 125

Ser Val Arg Gln Glu Gln Phe Arg Phe Phe Thr Glu Ala Leu Arg Ala
                130                 135                 140

Asn Lys Leu Arg Ser Tyr Val Asp Gln Met Val Ala Glu Ala Glu Glu
145                 150                 155                 160

Tyr Phe Ser Lys Trp Gly Glu Ser Gly Thr Val Asp Leu Lys Tyr Glu
                165                 170                 175

Leu Glu His Leu Ile Ile Leu Thr Ala Ser Arg Cys Leu Leu Gly Arg
```

```
                    180                 185                 190
Glu Val Arg Glu Lys Leu Phe Asp Asp Val Ser Ala Leu Phe His Asp
                195                 200                 205
Leu Asp Asn Gly Ile Gln Pro Ile Ser Val Leu Phe Pro Tyr Leu Pro
            210                 215                 220
Ile Pro Ala His Lys Arg Arg Asp Lys Ala Arg Ala Arg Leu Ala Glu
225                 230                 235                 240
Ile Phe Ala Thr Ile Ile Lys Ser Arg Lys Ala Ser Gly Gln Ser Glu
                245                 250                 255
Glu Asp Met Leu Gln Cys Phe Ile Asp Ser Lys Tyr Lys Asn Gly Arg
            260                 265                 270
Pro Thr Thr Glu Gly Glu Val Thr Gly Leu Leu Ile Ala Ala Leu Phe
            275                 280                 285
Ala Gly Gln His Thr Ser Ser Ile Thr Ser Thr Trp Thr Gly Ala Tyr
            290                 295                 300
Met Leu Arg Phe Lys Gln Tyr Phe Ala Glu Ala Val Glu Glu Gln Lys
305                 310                 315                 320
Asp Val Met Lys Arg His Gly Asp Lys Ile Asp His Asp Ile Leu Ala
                325                 330                 335
Glu Met Asp Val Leu Tyr Arg Cys Ile Lys Glu Ala Leu Arg Leu His
                340                 345                 350
Pro Pro Leu Ile Met Leu Leu Arg Gln Ser His Ser Asp Phe Thr Val
            355                 360                 365
Thr Thr Lys Glu Gly Lys Glu Tyr Asp Ile Pro Lys Gly His Ile Val
            370                 375                 380
Ala Thr Ser Pro Ser Phe Ala Asn Arg Leu Pro His Ile Tyr Lys Asn
385                 390                 395                 400
Pro Asp Ser Tyr Asp Pro Asp Arg Phe Gly Pro Gly Arg Glu Glu Asp
                405                 410                 415
Lys Ala Ala Gly Ala Phe Ser Tyr Ile Ser Phe Gly Gly Arg His
                420                 425                 430
Gly Cys Leu Gly Glu Pro Phe Ala Tyr Leu Gln Ile Lys Ala Ile Trp
            435                 440                 445
Thr His Leu Leu Arg Asn Phe Glu Phe Glu Leu Val Ser Pro Phe Pro
            450                 455                 460
Glu Asn Asp Trp Asn Ala Met Val Val Gly Ile Lys Gly Glu Val Met
465                 470                 475                 480
Val Asn Tyr Lys Arg Arg Lys Leu Val Val Asp Asn
                485                 490

<210> SEQ ID NO 177
<211> LENGTH: 490
<212> TYPE: PRT
<213> ORGANISM: Zea mays

<400> SEQUENCE: 177

Met Met Asp Leu Ala Asp Ser Gln Gln Gln Arg Leu Ile Ala Gly Ala
1               5                   10                  15
Ala Leu Leu Val Ala Thr Val Ala Phe Phe Arg Phe Leu Leu Arg Ser
                20                  25                  30
Arg Ser Gly Gly Lys Arg Leu Pro Pro Thr Ile Pro Gly Ala Pro Val
            35                  40                  45
Val Gly Gly Leu Val Lys Phe Met Arg Gly Pro Ile Pro Met Ile Arg
        50                  55                  60
Glu Gln Tyr Ala Arg Leu Gly Ser Val Phe Thr Val Pro Ile Ile Ser
```

```
          65                  70                  75                  80
Arg Lys Ile Thr Phe Leu Val Gly Pro Glu Val Ser Ala His Phe Phe
                85                  90                  95
Lys Gly Asn Glu Ala Glu Met Ser Gln Gln Glu Val Tyr Arg Phe Asn
                100                 105                 110
Val Pro Thr Phe Gly Pro Gly Val Phe Asp Val Asp Tyr Ser Ile
                115                 120                 125
Arg Gln Glu Gln Phe Arg Phe Phe Thr Glu Ala Leu Arg Ala Asn Lys
                130                 135                 140
Leu Arg Ser Tyr Val Asp Gln Met Val Val Glu Ala Glu Tyr Phe
145                 150                 155                 160
Ser Lys Trp Gly Glu Ser Gly Thr Val Asp Leu Lys Tyr Glu Leu Glu
                165                 170                 175
His Leu Ile Ile Leu Thr Ala Ser Arg Cys Leu Leu Gly Arg Glu Val
                180                 185                 190
Arg Glu Lys Leu Phe Asp Asp Val Ser Ala Leu Phe His Asp Leu Asp
                195                 200                 205
Asn Gly Met Gln Pro Ile Ser Val Leu Phe Pro Tyr Leu Pro Ile Pro
210                 215                 220
Ala His Lys Arg Arg Asp Arg Ala Arg Ala Arg Leu Ala Glu Ile Phe
225                 230                 235                 240
Ala Thr Ile Ile Lys Ser Arg Lys Ala Ser Gly Gln Ser Glu Glu Asp
                245                 250                 255
Met Leu Gln Cys Phe Ile Asp Ser Lys Tyr Lys Asn Gly Arg Ser Thr
                260                 265                 270
Ser Glu Gly Glu Val Thr Gly Leu Leu Ile Ala Ala Leu Phe Ala Gly
                275                 280                 285
Gln His Thr Ser Ser Ile Thr Ser Thr Trp Thr Gly Ala Tyr Met Leu
                290                 295                 300
Arg Phe Lys Gln Tyr Phe Ala Glu Ala Val Glu Glu Gln Lys Asp Val
305                 310                 315                 320
Met Lys Arg His Gly Asp Lys Ile Asp His Asp Ile Leu Ala Glu Met
                325                 330                 335
Asp Val Leu Tyr Arg Cys Ile Lys Glu Ala Leu Arg Leu His Pro Pro
                340                 345                 350
Leu Ile Met Leu Leu Arg Gln Ser His Ser Asp Phe Thr Val Thr Thr
                355                 360                 365
Lys Glu Gly Lys Val Tyr Asp Ile Pro Lys Gly His Ile Val Ala Thr
                370                 375                 380
Ser Pro Ser Phe Ala Asn Arg Leu Pro His Ile Tyr Lys Asn Pro Asp
385                 390                 395                 400
Ser Tyr Asp Pro Asp Arg Phe Gly Pro Gly Arg Glu Glu Asp Lys Ala
                405                 410                 415
Ala Gly Ala Phe Ser Tyr Ile Ser Phe Gly Gly Arg His Gly Cys
                420                 425                 430
Leu Gly Glu Pro Phe Ala Tyr Leu Gln Ile Lys Ala Ile Trp Thr His
                435                 440                 445
Leu Leu Arg Asn Phe Glu Phe Glu Leu Val Ser Pro Phe Pro Glu Asn
                450                 455                 460
Asp Trp Asn Ala Met Val Val Gly Ile Lys Gly Glu Val Met Val Asn
465                 470                 475                 480
Tyr Lys Arg Arg Lys Leu Val Val Asp Asn
                485                 490
```

-continued

```
<210> SEQ ID NO 178
<211> LENGTH: 490
<212> TYPE: PRT
<213> ORGANISM: Oryza sativa

<400> SEQUENCE: 178
```

| | | | | | | | | | | | | | | |
|---|---|---|---|---|---|---|---|---|---|---|---|---|---|---|
| Met | Met | Asp | Leu | Ala | Asp | Pro | Asn | His | Arg | Leu | Ile | Ala | Gly | Ala |
| 1 | | | | 5 | | | | | 10 | | | | | 15 |
| Leu | Leu | Val | Ala | Thr | Leu | Ala | Phe | Ile | Lys | Leu | Leu | Ser | Ser | Ala |
| | | | 20 | | | | | 25 | | | | | 30 | |
| Gly | Gly | Gly | Lys | Lys | Arg | Leu | Pro | Pro | Thr | Ile | Pro | Ala | Ala | Pro | Leu |
| | | 35 | | | | | 40 | | | | | 45 | | |
| Val | Gly | Gly | Leu | Leu | Arg | Phe | Met | Arg | Gly | Pro | Ile | Pro | Met | Ile | Arg |
| 50 | | | | | 55 | | | | | 60 | | | | |
| Glu | Glu | Tyr | Ala | Arg | Leu | Gly | Ser | Val | Phe | Thr | Val | Pro | Ile | Leu | Ser |
| 65 | | | | | 70 | | | | | 75 | | | | | 80 |
| Arg | Lys | Ile | Thr | Phe | Leu | Ile | Gly | Pro | Glu | Val | Ser | Ala | His | Phe | Phe |
| | | | | 85 | | | | | 90 | | | | | 95 | |
| Lys | Gly | Asn | Glu | Ala | Glu | Met | Ser | Gln | Gln | Glu | Val | Tyr | Lys | Phe | Asn |
| | | | 100 | | | | | 105 | | | | | 110 | |
| Val | Pro | Thr | Phe | Gly | Pro | Gly | Val | Val | Phe | Asp | Val | Asp | Tyr | Ser | Val |
| | | 115 | | | | | 120 | | | | | 125 | | |
| Arg | Gln | Glu | Gln | Phe | Arg | Phe | Phe | Thr | Glu | Ala | Leu | Arg | Ala | Asn | Lys |
| | 130 | | | | | 135 | | | | | 140 | | | |
| Leu | Arg | Ser | Tyr | Val | Asp | Gln | Met | Val | Val | Glu | Ala | Glu | Tyr | Phe |
| 145 | | | | | 150 | | | | | 155 | | | | 160 |
| Ser | Lys | Trp | Gly | Glu | Ser | Gly | Thr | Val | Asp | Leu | Lys | Tyr | Glu | Leu | Glu |
| | | | 165 | | | | | 170 | | | | | 175 | |
| His | Leu | Ile | Ile | Leu | Thr | Ala | Ser | Arg | Cys | Leu | Leu | Gly | Arg | Glu | Val |
| | | | 180 | | | | | 185 | | | | | 190 | |
| Arg | Glu | Lys | Leu | Phe | Asp | Asp | Val | Ser | Ser | Leu | Phe | His | Asp | Leu | Asp |
| | | 195 | | | | | 200 | | | | | 205 | | |
| Asn | Gly | Met | Gln | Pro | Val | Ser | Val | Ile | Phe | Pro | Tyr | Leu | Pro | Ile | Pro |
| | 210 | | | | | 215 | | | | | 220 | | | |
| Ala | His | Arg | Arg | Arg | Asp | Arg | Ala | Arg | Gln | Arg | Leu | Lys | Glu | Ile | Phe |
| 225 | | | | | 230 | | | | | 235 | | | | | 240 |
| Ala | Thr | Ile | Ile | Lys | Ser | Arg | Lys | Ala | Ser | Gly | Arg | Ala | Glu | Glu | Asp |
| | | | | 245 | | | | | 250 | | | | | 255 | |
| Met | Leu | Gln | Cys | Phe | Ile | Asp | Ser | Lys | Tyr | Lys | Ser | Gly | Arg | Ser | Thr |
| | | | 260 | | | | | 265 | | | | | 270 | |
| Thr | Glu | Gly | Glu | Ile | Thr | Gly | Leu | Leu | Ile | Ala | Ala | Leu | Phe | Ala | Gly |
| | | 275 | | | | | 280 | | | | | 285 | | |
| Gln | His | Thr | Ser | Ser | Ile | Thr | Ser | Thr | Trp | Thr | Gly | Ala | Tyr | Met | Leu |
| | 290 | | | | | 295 | | | | | 300 | | | |
| Arg | Phe | Lys | Gln | Tyr | Phe | Ala | Ala | Ala | Glu | Glu | Glu | Gln | Lys | Glu | Val |
| 305 | | | | | 310 | | | | | 315 | | | | | 320 |
| Met | Lys | Arg | His | Gly | Asp | Lys | Ile | Asp | His | Asp | Ile | Leu | Ala | Glu | Met |
| | | | | 325 | | | | | 330 | | | | | 335 | |
| Asp | Val | Leu | Tyr | Arg | Cys | Ile | Lys | Glu | Ala | Leu | Arg | Leu | His | Pro | Pro |
| | | | 340 | | | | | 345 | | | | | 350 | |
| Leu | Ile | Met | Leu | Leu | Arg | Gln | Ser | His | Asn | Asp | Phe | Ser | Val | Thr | Thr |
| | | 355 | | | | | 360 | | | | | 365 | | |
| Lys | Asp | Gly | Lys | Glu | Phe | Asp | Ile | Pro | Lys | Gly | His | Ile | Val | Ala | Thr |
| | 370 | | | | | 375 | | | | | 380 | | | |

```
Ser Pro Ala Phe Ala Asn Arg Leu Pro His Ile Phe Lys Asn Pro Asp
385                 390                 395                 400

Ser Tyr Asp Pro Asp Arg Tyr Ala Pro Gly Arg Glu Glu Asp Lys Ala
            405                 410                 415

Ala Gly Ala Phe Ser Tyr Ile Ser Phe Gly Gly Gly Arg His Gly Cys
        420                 425                 430

Leu Gly Glu Pro Phe Ala Tyr Leu Gln Ile Lys Ala Ile Trp Thr His
    435                 440                 445

Leu Leu Arg Asn Phe Glu Phe Glu Leu Val Ser Pro Phe Pro Glu Thr
450                 455                 460

Asn Trp Lys Ala Met Val Val Gly Ile Lys Asp Glu Val Met Val Asn
465                 470                 475                 480

Phe Lys Arg Arg Lys Leu Val Val Asp Asn
                485                 490

<210> SEQ ID NO 179
<211> LENGTH: 490
<212> TYPE: PRT
<213> ORGANISM: Avena strigosa

<400> SEQUENCE: 179

Met Asp Leu Leu Ala Asp Ala Lys Pro Gln Trp Leu Leu Ala Gly Ala
1               5                   10                  15

Ala Leu Leu Leu Ala Thr Leu Ala Phe Leu Lys Val Leu Phe Gly Ser
            20                  25                  30

Gly Gly Gly Lys Arg Ala Pro Pro Thr Ile Pro Gly Ala Pro Val
        35                  40                  45

Val Gly Gly Leu Leu Arg Phe Leu Lys Gly Pro Ile Pro Leu Ile Arg
50                  55                  60

Ala Glu Tyr Ala Arg Leu Gly Ser Val Phe Thr Val Pro Ile Leu Thr
65                  70                  75                  80

Arg Arg Ile Thr Phe Leu Ile Gly Pro Glu Val Ser Gly His Phe Phe
                85                  90                  95

Lys Gly Asn Glu Ser Glu Met Ser Gln Gln Glu Val Tyr Arg Phe Asn
            100                 105                 110

Val Pro Thr Phe Gly Pro Gly Val Phe Asp Val Asp Tyr Leu Val
            115                 120                 125

Arg Gln Glu Gln Phe Arg Phe Phe Thr Glu Ala Leu Lys Ser Asn Lys
130                 135                 140

Leu Arg Ser Tyr Val Asp Met Met Val Ala Glu Ala Glu Asp Tyr Phe
145                 150                 155                 160

Ser Thr Trp Gly Glu Ser Gly Thr Val Asp Leu Lys Tyr Glu Leu Glu
            165                 170                 175

His Leu Ile Ile Leu Thr Ala Ser Arg Cys Leu Leu Gly Arg Glu Val
            180                 185                 190

Arg Glu Lys Leu Phe Asp Asp Val Ser Ala Leu Phe His Asp Leu Asp
        195                 200                 205

Asn Gly Met Gln Pro Ile Ser Val Ile Phe Pro Tyr Leu Pro Ile Pro
    210                 215                 220

Ala His Arg Lys Arg Asp Gln Ala Arg Ala Arg Leu Ala Glu Ile Phe
225                 230                 235                 240

Ala Thr Ile Ile Lys Ser Arg Lys Ala Ser Gly Gln Ser Glu Glu Asp
                245                 250                 255

Met Leu Gln Cys Phe Ile Asp Ser Lys Tyr Arg Asn Gly Arg Pro Thr
            260                 265                 270
```

```
Thr Glu Ile Glu Val Thr Gly Leu Leu Ile Ala Ala Leu Phe Ala Gly
        275                 280                 285

Gln His Thr Ser Ser Ile Thr Ser Thr Trp Thr Gly Ala Tyr Leu Leu
    290                 295                 300

Lys Phe Gln Gln Tyr Phe Ala Glu Ala Val Glu Glu Gln Lys Arg Val
305                 310                 315                 320

Met Lys Arg His Gly Asp Lys Ile Asp His Asp Ile Leu Ala Glu Met
                325                 330                 335

Asp Val Leu Tyr Arg Cys Ile Lys Glu Ala Leu Arg Leu His Pro Pro
            340                 345                 350

Leu Ile Met Leu Leu Arg Gln Ser His Thr Asp Phe Ser Val Thr Thr
        355                 360                 365

Arg Glu Gly Lys Glu Tyr Asp Ile Pro Lys Gly His Ile Val Ala Thr
    370                 375                 380

Ser Pro Ser Phe Ala Asn Arg Leu Pro His Ile Phe Lys Asn Pro Asp
385                 390                 395                 400

Ser Tyr Asp Pro Asp Arg Phe Ala Pro Gly Arg Glu Glu Asp Lys Ala
                405                 410                 415

Ala Gly Ala Phe Ser Tyr Ile Ser Phe Gly Gly Gly Arg His Gly Cys
            420                 425                 430

Leu Gly Glu Pro Phe Ala Tyr Leu Gln Ile Lys Ala Ile Trp Thr His
        435                 440                 445

Leu Leu Arg Asn Phe Glu Phe Glu Leu Val Ser Pro Phe Pro Glu Asn
    450                 455                 460

Asp Trp Asn Ala Met Val Val Gly Ile Lys Gly Glu Val Met Val Asn
465                 470                 475                 480

Tyr Lys Arg Arg Lys Leu Val Val Asp Asn
                485                 490

<210> SEQ ID NO 180
<211> LENGTH: 490
<212> TYPE: PRT
<213> ORGANISM: Avena strigosa

<400> SEQUENCE: 180

Met Asp Met Thr Ile Cys Val Val Trp Leu Val Leu Ala Ile Ile Ser
1               5                   10                  15

Ile Ala Ala Val Val Ser Lys Ser Ser Lys Arg Ser Asn Ala Ser Asp
                20                  25                  30

Ser Val Val Thr Arg Pro Pro Pro Val Val Thr Gly Ile Asp Leu
            35                  40                  45

Leu Lys Phe Leu His Ala Leu Cys Arg Lys Asp Pro Glu Ala Ala Met
        50                  55                  60

Met Tyr Leu Tyr Asn Lys Leu Gly Ser Ile Phe Thr Leu Ser Phe Leu
65                  70                  75                  80

Trp Lys Arg Val Thr Ile Leu Ile Gly His Ala Ser Ile Pro Phe
                85                  90                  95

Phe His Gly Leu Glu Ser Asp Val Ser Gln Gly Asn Phe Asn Glu Phe
            100                 105                 110

Thr Val Pro Met Phe Gly Lys Glu Asn Gly Tyr Ala Val Glu Tyr Ala
        115                 120                 125

Thr Arg Ile Glu Gln Ser Arg Phe Phe Tyr Asp Ser Leu Lys Ala Ser
    130                 135                 140

Gln Leu Arg Ser His Val Asp Leu Ile Arg Gln Glu Val Glu Glu Tyr
145                 150                 155                 160
```

```
Phe Ala Lys Trp Gly Asp Glu Gly Val Asp Leu Lys Gln Glu Phe
            165                 170                 175
Thr Lys Leu Leu Met Leu Ile Ala Gly Arg Cys Leu Leu Gly Ser Glu
        180                 185                 190
Val Arg Asp Thr Ile Phe Gly Glu Phe Tyr Thr Leu Phe Ala Asp Ile
            195                 200                 205
Glu Glu Gly Val Asn Leu Phe Ser Tyr Met Phe Pro Tyr Met Pro Val
        210                 215                 220
Pro Val Asn Asn Arg Arg Asp Arg Ala Gln Met Lys Leu Thr Ser Ile
225                 230                 235                 240
Val Ser Glu Ile Val Arg Ser Arg Lys Arg Cys Asn Arg Val Glu Asp
            245                 250                 255
Asp Met Leu Gln Arg Leu Ile Asp Ser Arg Tyr Lys Asp Gly Arg Pro
        260                 265                 270
Thr Thr Glu Gly Glu Val Ser Gly Met Ile Ile Gly Leu Ile Phe Ala
            275                 280                 285
Gly Lys His Thr Ser Thr Ile Thr Ala Ser Trp Thr Gly Ala Cys Leu
        290                 295                 300
Leu Thr His Pro Lys Phe Leu Gly Ala Ala Val Glu Glu Gln Lys Gln
305                 310                 315                 320
Met Met Ser Lys Tyr Lys Asp Asn Ile Asp Tyr Asn Ile Leu Ser Glu
            325                 330                 335
Met Glu Ile Leu His Ser Cys Ile Lys Glu Ala Gly Arg Met Tyr Pro
        340                 345                 350
Ala Ala Pro Val Leu Leu Arg Lys Thr Leu Lys Glu Ile Ser Val Gln
            355                 360                 365
Thr Arg Glu Gly Gly Glu Tyr Gly Ile Pro Lys Gly Thr Thr Leu Ala
        370                 375                 380
His Leu Val Met Leu Thr Gly Lys Val Pro His Thr Tyr Lys Asp Pro
385                 390                 395                 400
Glu Val Tyr Asp Pro Asp Arg Phe Arg Val Gly Arg Glu Glu Asp Lys
            405                 410                 415
Ile Gly Gly Lys Leu Ser Tyr Thr Ile Phe Gly Ala Gly Arg His Ala
        420                 425                 430
Cys Ala Gly Glu Ser Phe Ala Phe Met Gln Ile Lys Ile Ile Trp Ser
            435                 440                 445
His Leu Leu Arg Asn Phe Asp Leu Lys Leu Thr Ser Pro Phe Pro Lys
        450                 455                 460
Gln Asp Trp Ser Lys Phe Ile Ile Glu Pro Lys Gly Lys Val Met Val
465                 470                 475                 480
Ser Tyr Lys Arg Cys Arg Met Pro Ala Asn
            485                 490

<210> SEQ ID NO 181
<211> LENGTH: 2998
<212> TYPE: DNA
<213> ORGANISM: Avena strigosa

<400> SEQUENCE: 181
gtttattgat cacacaatag tgagagacac ggcccttgca aaacagactg ccaaaccact      60
gcatagtcgc caaacaacg acaataaagc tcgaaaacta tctccaagga gcagagcatg     120
acgggccaca ctaagacttg gaatggagga atgctacttt taatccatgc cgccttaatt    180
acggaaattt ttcacgaata acacgctaaa gtgacaaaga tatataccta attccacatg    240
acagacgaac catgcatcca ttgcaaccca ataacttata gatcgtgtta aggtgagggg    300
```

```
aatgattttg tgtaagagta aacactttgt tataagttaa cataaaaaac caaatattta      360
caaactctaa taacaataca attgaataac gagagtgtat ttacttggat caagtgtctt      420
gtccatattg tcacatagtc actacaaaca ttattcttac aaaagtatcc acatcaaaaa      480
aataaattat attatgtata aaaagcaaca taagacctaa aatagagaga tattctagaa      540
attcttacaa aagccaaaca tccagctgct aatatggtag accatattgg tatttaaaca      600
tatcacaact aggggttttg tttctcgctg gaaggaaata cttgtgggca atggtatttc      660
cggttttcga aaatactaga gctgccggtc aaactacctc ccgaatttt  tcaaacaaac      720 ccatccaaag tttatcaaaa ttctttaaat tttagaaaaa tattaaaata cctatgaatt      780
tggtatggta gtatttgttc ttagtggtaa ccggaaacac ccgtttctga ctacataccc      840
gaacatcggt caagaataaa aacctgatca taaccattga atctccgtaa gtttgctaac      900
gtatcatgct gttctcatgt tacataagaa aaatgataaa aatcccctcg atttagtaac      960
actatgcatt aggtttgtag aagagtaaat gtttgagaaa atgatagtag attattaata     1020
tttgtcctga ccatgcgcat gagacactag ctaagtgtcc catagtaagt attgacacat     1080
ctagagatat gtccatgtct taaatatcgt gtatttgtta tattaaggat ataaatgtga     1140
gaatatgttg gtataacatt ggaaaaaatg ttaacatact aaacatgact acctcacatt     1200
ttttacggac attgatattc tagaactatc aataccgcta tactaccagt aggatatcat     1260
cttcaatatc gatgatgtag atatgcaaac ttgcactttc aaaagaatgt taatataat      1320 tttctaagtg aactatctac cgagacatta tatctttaat aatataaaaa attctttatt     1380
gattttcctg aatttgaaac ccaaaatatg tcggtctacc tcttcgaaaa atgacattta     1440
gctcatggta tgtcttttc catgatataa taaagtaatt tgtatcttat atttaagtat      1500
acaagtcatt caaaaggtag ttttagtcat gtgatatttt ttgtgtggtg tctctagaat     1560
aattattaat aaattcaaaa ttttagtatg tatataacca taaatttatt tctcaagcaa     1620
ataaaatgag attaagacat tgccctcgca attgcgaggt ctacctggct agtgagagaa     1680
aaaaggagaa catgcattga accagagaga gagtaataaa tgagataacc cttataatct     1740
caaacaatat aaaaaagctc ttaggactaa taatcctgaa cagaggtagt aacatgcaac     1800
tgtatgcatt gcgaactacg cattttgatg acatgacatg tcattaaata atgaaaacag     1860
tcttgtggta actagctatg ttaccataac acaagacatg tctaagtaag atgagtctat     1920
gatataataa atgagatatt ccataaaact agatataagt tactacccac tctgaagatg     1980
ataacaaaga atagtaatgc acgcatgaca atacactatt tactagtctt ctgtaaattt     2040
atccgatcaa aatggcctgc tcgggttgca atgcattctc acgtgttgaa gtttctgata     2100
tcgatgtaag gtggtcatac aagacgagaa taccaatgga gtactagatc tcgatggact     2160
aagcatatgc aaattttatc tgaacaagaa gcaggcttac tcaggttgca atgtattctc     2220
acgtactgtt gccttgctcc agacgacccg catgcaaaag cgagcttgtc ccctagagtt     2280
gtgaatacta gtttcattag aaacatcacg tactgcgaaa gccattaatg cctctgtgaa     2340
cacaatcggg cagtattgac tagaatctcc aagatcaggc catgaaatta gttgtttact     2400
tgataatatt gtccaagagt tagggtttag gtcaagtaga ggccgtggct ttttccatt      2460 tctccataat aaaagggctt aggtcaagta gtagctgcct atataaatga ggcattgcgg     2520
ggttccttac tcacttgtgt gcattgactg ctaccagctg tgtgctggac actcgttcac     2580
agtgaaccag tcaggaggat ttcaaattcg tattcaggta tgcttgattt tagttttaa      2640 gtcatatgag ttcattttta gatcattttt tcatacgaga gaaataagac tagggctagg     2700
```

```
tttgttcttc atatgggccg ggtgcaacat ttcgataaca atcacgcatc agagctatta    2760
cttgttcttc tgaattttct atagccttta aaaaccgaca atcagagttc aattaccaat    2820
ctagtcttgg tcatattttg tttcttaatg aagtgttttt gcttcacttt gtccttgtgg    2880
agtcgaatgt ggcttcctgt ttagactgtt agctaggttc acccttttcag atttcttcat   2940 actaattatc ttcatattct gccagtgtga atcctctagt caataacgac atggcacc     2998
```

<210> SEQ ID NO 182
<211> LENGTH: 2996
<212> TYPE: DNA
<213> ORGANISM: Avena strigosa

<400> SEQUENCE: 182

```
aaaatatgtc cctatctata tttgagttta tatagatata tcttattttt ctgcaaattt     60
tgatatatta tatgtatttt tctgaattta ataatttag ttatgatttt tctaagatta     120
atgtggcaaa aaaagaaaa atagctaagc cgtcggcgta ggtctgaaac ctacgcgtag     180
acttgacgcc gttgctctac cgttagccca atgggctacg ccgacggtca tgtttacgcc    240 gacgcggcc gtcggcctat ttattctacg ccgacggcaa aattgggccg acgcccgtc     300 aagctacgcc gacggtcccg acattttgcc gtcggcgtat aaaagaccg tcggcctatt   360 tagttattcc cgtagtgtgt cggtgttgac actattatgg taactatcct aaccggtagg   420
ttacaattat cagggctttg tcatgcacat ttataaatgt gaatcaggtt gaactttatt   480
tggtgttccc aatcagacgt tagtaaacac aatatcagat taacctggga aatcttcatg   540
taacttagac taataaaatg catctgttac cgtgtacaaa tactatcact aaccagatcc   600
ctgcaagaca agatccacgg atcatggtgc agcgatttac gagataatct attgactaat   660
tatacttgtt ctagtactat ctactgaccc ttctctggaa gacaaccatc gtgtattctg   720
caccgatgga agtgaataga tctttcttgt attatccctc atgaaggcac tcagagcaaa   780
cttgagcgaa ccttccgcat tcatttcttc acatgcggtg tctgatcagt caaacaacct   840
ccagagattt agtaaaaaca atgtctcggg attccgcgat taatttagtc gtcttatggc   900
ctcgagtact tgttataata agatgatttg atacttgcag tatctttaca aactgctagc    960
taaattggac agtagctagt tttgtcagtc tagtacgtac tacatagtat tttttctgt    1020 atctagtggc actactgaaa tctcactttc cacgatttca ataaaaatt acctgatctg    1080 acatgatcac tggctacgcc gagattctac aaatatttct ataagtagtt tgtggattcc    1140
aatatatata cggattccgt aaagctctct taccgatggt atgactttag tagtaacaaa    1200
atcataggct tcgagtgaag attggctacc aactgtaatg taagattgtt gtccaagata    1260
agatactcaa gttacagatg cactactcta atactaagag ttattgatct atattacggc    1320
tcccgtaccg tagagatatt gattctacgt tcaccttctt aaaaggagat tcttgtacaa    1380
tcaaaacaaa tgggtctagc taccttggtc aatatgtatt tctatcggta tttagttata    1440
aaggagagga atacagaata attttttaa ctccatagta cctctattgc tttcagtata    1500
aagagtttga tgcacggttc tctgtactaa taaatgttct attgttgatt gattcttaac    1560
cgcatcctat gcaattttaa cctcaaaaaa gtttcacggt acaccgactt gccttactag    1620
ccctactgtt ttcttgagaa ggatgttcaa actttgggct tttgcatcta aaataagaca    1680
cacatcattt ttggtttatt attcaacaat gtgtgggaaa agcatacaac aatcaactcg    1740
atataccacc ttcgcggagg gcctcctctt taaatgtctg ggagtactac acatatgtaa    1800
agatgatgcc cacttacaaa gaacgaggac accacttaaa ccgggtgtac aaagtactac    1860
```

```
acatatgtaa agatgaggcc atagaacaag caagagcacc aagatattta gatccactaa    1920
aatgcaacca cctcgatgtc cataaaaaat gatggtgacg tacaacactc aacaaatatc    1980
gataaaaatg atagtgtcct agttgcacat cttctaacat gttggtgtct attatgcaca    2040
agtgggcatg gaagcaagta aatattgtgt actatagcta ctggtgactc gagtgtatct    2100
ccaagactcg atagcaaacc cgaagcctct tcagcttgtc cacatatcat tgtggaatgt    2160
tcactacgac tcgccacgcc aagcataacc tggataagcc acgtgggata tgagatttcc    2220
cgcagcttcc ctctgagtga ggaggcagaa ctatacgcct caacacgacg agccacccccc   2280 taaggctagt catagtggga gtaacttggg tagtaacata ttcctacata tattgcgaac    2340
taagcattta gatgacatga catgcaatta aatgatgaga gagagtctta tgataactag    2400
ctatgttacc ataacatcac acatttctaa aaaaataaat ctatattata ataaataagg    2460
ttttgcatga taccacatct atgttatttt gcactatgaa gatagtaact tagactagta    2520
acatatacat gttactactc taagttactc cccacaatga ccagcctaac accttttgta    2580
ctgttttgca catttgcagt ttacttttte ttaggtgaag agaaaacaca agacataatt    2640
ttaatatttc aacttcatta cgtgctggtg caaataattt ttacggtgca attttcgaca    2700
tgatttattg tatatttaca gaaatttatg ctccaaattt gtttggtacc ttcagtatta    2760
gtttctggac attgtacata ttatgttgcc gtataagctg agctagaagg atcattagtg    2820
taattccata tatatctaaa tgtacctgtg gaatcacatt tgaggaagtt ccaatgatgc    2880
cctttttgcc ctgcacacgc atatataaga accctttgcc cgcagcatag agctagtact    2940
agctagtatc ccattgcttg ttttcctcgc atacactgcc cgttgttggt gcgcac         2996

<210> SEQ ID NO 183
<211> LENGTH: 2996
<212> TYPE: DNA
<213> ORGANISM: Avena strigosa

<400> SEQUENCE: 183
gtgcgcacca caacgggca gtgtatgcga ggaaaacaag caatgggata ctagctagta      60
ctagctctat gctgcgggca aagggttctt atatatgcgt gtgcagggca aaagggcat     120 cattggaact tcctcaaatg tgattccaca ggtacattta gatatatatg gaattacact    180
aatgatcctt ctagctcagc ttatacggca acataatatg tacaatgtcc agaaactaat    240
actgaaggta ccaaacaaat ttggagcata aatttctgta aatatacaat aaatcatgtc    300
gaaaattgca ccgtaaaaat tatttgcacc agcacgtaat gaagttgaaa tattaaaatt    360
atgtcttgtg ttttctcttc acctaagaaa agtaaactg caaatgtgca aaacagtaca    420
aaaggtgtta ggctggtcat tgtggggagt aacttagagt agtaacatgt atatgttact    480
agtctaagtt actatcttca tagtgcaaaa taacatagat gtggtatcat gcaaaacctt    540
atttattata atatagattt atttttttag aaatgtgtga tgttatggta acatagctag    600
ttatcataag actctctctc atcatttaat tgcatgtcat gtcatctaaa tgcttagttc    660
gcaatatatg taggaatatg ttactaccca agttactccc actatgacta gccttagggg    720
gtggctcgtc gtgttgaggc gtatagttct gcctcctcac tcagagggaa gctgcgggaa    780
atctcatatc ccacgtggct tatccaggtt atgcttggcg tggcgagtcg tagtgaacat    840
tccacaatga tatgtggaca agctgaagag gcttcgggtt tgctatcgag tcttggagat    900
acactcgagt caccagtagc tatagtacac aatatttact tgcttccatg cccacttgtg    960
cataatagac accaacatgt tagaagatgt gcaactagga cactatcatt tttatcgata   1020
```

```
tttgttgagt gttgtacgtc accatcattt tttatggaca tcgaggtggt tgcattttag    1080
tggatctaaa tatcttggtg ctcttgcttg ttctatggcc tcatctttac atatgtgtag    1140
tactttgtac acccggttta agtggtgtcc tcgttctttg taagtgggca tcatctttac    1200
atatgtgtag tactcccaga catttaaaga ggaggccctc cgcgaaggtg gtatatcgag    1260
ttgattgttg tatgcttttc ccacacattg ttgaataata aaccaaaaat gatgtgtgtc    1320
ttattttaga tgcaaaagcc caaagtttga acatccttct caagaaaaca gtagggctag    1380
taaggcaagt cggtgtaccg tgaaactttt ttgaggttaa aattgcatag gatgcggtta    1440
agaatcaatc aacaatagaa catttattag tacagagaac cgtgcatcaa actctttata    1500
ctgaaagcaa tagaggtact atggagttaa aaaaattatt ctgtattcct ctcctttata    1560
actaaatacc gatagaaata catattgacc aaggtagcta gacccatttg ttttgattgt    1620
acaagaatct ccttttaaga aggtgaacgt agaatcaata tctctacggt acggagccg     1680
taatatagat caataactct tagtattaga gtagtgcatc tgtaacttga gtatcttatc    1740
ttggacaaca atcttacatt acagttggta gccaatcttc actcgaagcc tatgattttg    1800
ttactactaa agtcatacca tcggtaagag agctttacgg aatccgtata tatattggaa    1860
tccacaaact acttatagaa atatttgtag aatctcggcg tagccagtga tcatgtcaga    1920
tcaggtaatt tttatttgaa atcgtggaaa gtgagatttc agtagtgcca ctagatacag    1980
aaaaaaatac tatgtagtac gtactagact gacaaaacta gctactgtcc aatttagcta    2040
gcagtttgta aagatactgc aagtatcaaa tcatcttatt ataacaagta ctcgaggcca    2100
taagacgact aaattaatcg cggaatcccg agacattgtt tttactaaat ctctggaggt    2160
tgtttgactg atcagacacc gcatgtgaag aaatgaatgc ggaaggttcg ctcaagtttg    2220
ctctgagtgc cttcatgagg gataatacaa gaaagatcta ttcacttcca tcggtgcaga    2280
atacacgatg gttgtcttcc agagaagggt cagtagatag tactgaaaca agtataatta    2340
gtcaatagat tatctcgtaa atcgctgcac catgatccgt ggatcttgtc ttgcagggat    2400
ctggttagtg atagtatttg tacacggtaa cagatgcatt ttattagtct aagttacatg    2460
aagatttccc aggttaatct gatattgtgt ttactaacgt ctgattggga acaccaaata    2520
aagttcaacc tgattcacat ttataaatgt gcatgacaaa gccctgataa ttgtaaccta    2580
ccggttagga tagttaccat aatagtgtca acaccgacac actacgggaa taactaaata    2640
ggccgacggt ctttttatac gccgacggca aaatgtcggg accgtcggcg tagcttgacg    2700
gggcgtcggc ccaattttgc cgtcggcgta gaataaatag gccgacggcc gccgtcggcg    2760
taaacatgac cgtcggcgta gcccattggg ctaacggtag agcaacgcg tcaagtctac     2820
gcgtaggttt cagacctacg ccgacggctt agctattttt cttttttttg ccacattaat    2880
cttagaaaaa tcataactaa attatttaaa ttcagaaaaa tacatataat atatcaaaat    2940
ttgcagaaaa ataagatata tctatataaa ctcaaatata gatagggaca tatttt        2996
```

<210> SEQ ID NO 184
<211> LENGTH: 2998
<212> TYPE: DNA
<213> ORGANISM: Avena strigosa

<400> SEQUENCE: 184

```
gaaaatatgt ccctatctat atttgagttt atatagatat atcttatttt tctgcaaatt      60
ttgatatatt atatgtattt ttctgaattt aaataattta gttatgattt ttctaagatt     120
aatgtggcaa aaaaaagaaa aatagctaag ccgtcggcgt aggtctgaaa cctacgcgta    180
```

```
gacttgacgc cgttgctcta ccgttagccc aatgggctac gccgacggtc atgtttacgc    240
cgacggcggc cgtcggccta tttattctac gccgacggca aaattgggcc gacgcccgt     300 caagctacgc cgacggtccc gacattttgc cgtcggcgta taaaaagacc gtcggcctat    360
ttagttattc ccgtagtgtg tcggtgttga cactattatg gtaactatcc taaccggtag    420
gttacaatta tcagggcttt gtcatgcaca tttataaatg tgaatcaggt tgaactttat    480
ttggtgttcc caatcagacg ttagtaaaca caatatcaga ttaacctggg aaatcttcat    540
gtaacttaga ctaataaaat gcatctgtta ccgtgtacaa atactatcac taaccagatc    600
cctgcaagac aagatccacg gatcatggtg cagcgattta cgagataatc tattgactaa    660
ttatacttgt tctagtacta tctactgacc cttctctgga agacaaccat cgtgtattct    720
gcaccgatgg aagtgaatag atctttcttg tattatccct catgaaggca ctcagagcaa    780
acttgagcga accttccgca ttcatttctt cacatgcggt gtctgatcag tcaaacaacc    840
tccagagatt tagtaaaaac aatgtctcgg gattccgcga ttaatttagt cgtcttatgg    900
cctcgagtac ttgttataat aagatgattt gatacttgca gtatctttac aaactgctag    960
ctaaattgga cagtagctag ttttgtcagt ctagtacgta ctacatagta tttttttctg   1020
tatctagtgg cactactgaa atctcacttt ccacgatttc aaataaaaat tacctgatct   1080
gacatgatca ctggctacgc cgagattcta caaatatttc tataagtagt ttgtggattc   1140
caatatatat acggattccg taaagctctc ttaccgatgg tatgacttta gtagtaacaa   1200
aatcataggc ttcgagtgaa gattggctac caactgtaat gtaagattgt tgtccaagat   1260
aagatactca agttacagat gcactactct aatactaaga gttattgatc tatattacgg   1320
ctcccgtacc gtagagatat tgattctacg ttccaccttct taaaaggaga ttcttgtaca   1380
atcaaaacaa atgggtctag ctaccttggt caatatgtat ttctatcggt atttagttat   1440
aaaggagagg aatacagaat aatttttta actccatagt acctctattg ctttcagtat    1500
aaagagtttg atgcacggtt ctctgtacta ataaatgttc tattgttgat tgattcttaa    1560
ccgcatccta tgcaatttta acctcaaaaa agtttcacgg tacaccgact tgccttacta    1620
gccctactgt tttcttgaga aggatgttca aactttgggc ttttgcatct aaaataagac    1680
acacatcatt tttggtttat tattcaacaa tgtgtgggaa aagcatacaa caatcaactc    1740
gatataccac cttcgcggag ggcctcctct ttaaatgtct gggagtacta cacatatgta    1800
aagatgatgc ccacttacaa agaacgagga caccacttaa accgggtgta caaagtacta    1860
cacatatgta aagatgaggc catagaacaa gcaagagcac caagatattt agatccacta    1920
aaatgcaacc acctcgatgt ccataaaaaa tgatggtgac gtacaacact caacaaatat    1980
cgataaaaat gatagtgtcc tagttgcaca tcttctaaca tgttggtgtc tattatgcac    2040
aagtgggcat ggaagcaagt aaatattgtg tactatagct actggtgact cgagtgtatc    2100
tccaagactc gatagcaaac ccgaagcctc ttcagcttgt ccacatatca ttgtggaatg    2160
ttcactacga ctcgccacgc caagcataac ctgataagc cacgtgggat atgagatttc     2220
ccgcagcttc cctctgagtg aggaggcaga actatacgcc tcaacacgac gagccacccc    2280
ctaaggctag tcatagtggg agtaacttgg gtagtaacat attcctacat atattgcgaa    2340
ctaagcattt agatgacatg acatgcaatt aaatgatgag agagagtctt atgataacta    2400
gctatgttac cataacatca cacatttcta aaaaataaa tctatattat aataaataag     2460
gttttgcatg ataccacatc tatgttattt tgcactatga agatagtaac ttagactagt    2520
aacatataca tgttactact ctaagttact ccccacaatg accagcctaa cacctttgt     2580
```

| | |
|---|---:|
| actgttttgc acatttgcag tttactttt cttaggtgaa gagaaaacac aagacataat | 2640 |
| tttaatattt caacttcatt acgtgctggt gcaaataatt tttacggtgc aattttcgac | 2700 |
| atgatttatt gtatatttac agaaatttat gctccaaatt tgtttggtac cttcagtatt | 2760 |
| agtttctgga cattgtacat attatgttgc cgtataagct gagctagaag gatcattagt | 2820 |
| gtaattccat atatatctaa atgtacctgt ggaatcacat ttgaggaagt tccaatgatg | 2880 |
| cccttttttgc cctgcacacg catatataag aacccttttgc ccgcagcata gagctagtac | 2940 |
| tagctagtat cccattgctt gttttcctcg catacactgc ccgttgttgg tgcgcacc | 2998 |

<210> SEQ ID NO 185
<211> LENGTH: 1900
<212> TYPE: DNA
<213> ORGANISM: Avena strigosa

<400> SEQUENCE: 185

| | |
|---|---:|
| gccgagattc tacaaatatt tctataagta gtttgtggat tccaatatat atacggattc | 60 |
| cgtaaagctc tcttaccgat ggtatgactt tagtagtaac aaaatcatag gcttcgagtg | 120 |
| aagattggct accaactgta atgtaagatt gttgtccaag ataagatact caagttacag | 180 |
| atgcactact ctaatactaa gagttattga tctatattac ggctcccgta ccgtagagat | 240 |
| attgattcta cgttcacctt cttaaaagga gattcttgta caatcaaaac aaatgggtct | 300 |
| agctaccttg gtcaatatgt atttctatcg gtatttagtt ataaaggaga ggaatacaga | 360 |
| ataatttttt taactccata gtacctctat tgctttcagt ataaagagtt tgatgcacgg | 420 |
| ttctctgtac taataaatgt tctattgttg attgattctt aaccgcatcc tatgcaattt | 480 |
| taacctcaaa aaagtttcac ggtacaccga cttgccttac tagccctact gttttcttga | 540 |
| gaaggatgtt caaactttgg gcttttgcat ctaaaataag acacacatca ttttggtttt | 600 |
| attattcaac aatgtgtggg aaaagcatac aacaatcaac tcgatatacc accttcgcgg | 660 |
| agggcctcct ctttaaatgt ctgggagtac tacacatatg taaagatgat gcccacttac | 720 |
| aaagaacgag gacaccactt aaaccgggtg tacaaagtac tacacatatg taaagatgag | 780 |
| gccatagaac aagcaagagc accaagatat ttagatccac taaaatgcaa ccacctcgat | 840 |
| gtccataaaa aatgatggtg acgtacaaca ctcaacaaat atcgataaaa atgatagtgt | 900 |
| cctagttgca catcttctaa catgttggtg tctattatgc acaagtgggc atggaagcaa | 960 |
| gtaaatattg tgtactatag ctactggtga ctcgagtgta tctccaagac tcgatagcaa | 1020 |
| acccgaagcc tcttcagctt gtccacatat cattgtggaa tgttcactac gactcgccac | 1080 |
| gccaagcata acctggataa gccacgtggg atatgagatt tcccgcagct tccctctgag | 1140 |
| tgaggaggca gaactatacg cctcaacacg acgagccacc ccctaaggct agtcatagtg | 1200 |
| ggagtaactt gggtagtaac atattcctac atatattgcg aactaagcat ttagatgaca | 1260 |
| tgacatgcaa ttaaatgatg agagagagtc ttatgataac tagctatgtt accataacat | 1320 |
| cacacatttc taaaaaaata aatctatatt ataataaata aggttttgca tgataccaca | 1380 |
| tctatgttat tttgcactat gaagatagta acttagacta gtaacatata catgttacta | 1440 |
| ctctaagtta ctccccacaa tgaccagcct aacacctttt gtactgtttt gcacatttgc | 1500 |
| agtttacttt ttcttaggtg aagagaaaac acaagacata attttaatat ttcaacttca | 1560 |
| ttacgtgctg gtgcaaataa ttttttacggt gcaattttcg acatgattta ttgtatattt | 1620 |
| acagaaattt atgctccaaa tttgtttggt accttcagta ttagtttctg gacattgtac | 1680 |
| atattatgtt gccgtataag ctgagctaga aggatcatta gtgtaattcc atatatatct | 1740 |

```
aaatgtacct gtggaatcac atttgaggaa gttccaatga tgccctttt gccctgcaca    1800 cgcatatata agaacccttt gcccgcagca tagagctagt actagctagt atcccattgc    1860
ttgttttcct cgcatacact gcccgttgtt ggtgcgcacc                          1900
```

<210> SEQ ID NO 186
<211> LENGTH: 1900
<212> TYPE: DNA
<213> ORGANISM: Avena strigosa

<400> SEQUENCE: 186

```
cttaaatatc gtgtatttgt tatattaagg atataaatgt gagaatatgt tggtataaca     60
ttggaaaaaa tgttaacata ctaaacatga ctacctcaca ttttttacgg acattgatat    120
tctagaacta tcaataccgc tatactacca gtaggatatc atcttcaata tcgatgatgt    180
agatatgcaa acttgcactt tcaaaagaat gtttaatata attttctaag tgaactatct    240
accgagacat tatatcttta ataatataaa aaattcttta ttgattttcc tgaatttgaa    300
acccaaaata tgtcggtcta cctcttcgaa aaatgacatt tagctcatgg tatgtctttt    360
tccatgatat aataaagtaa tttgtatctt atatttaagt atacaagtca ttcaaaaggt    420
agttttagtc atgtgatatt ttttgtgtgg tgtctctaga ataattatta ataaattcaa    480
aattttagta tgtatataac cataaatta tttctcaagc aaataaaatg agattaagac    540
attgccctcg caattgcgag gtctacctgg ctagtgagag aaaaaaggag aacatgcatt    600
gaaccagaga gagagtaata aatgagataa cccttatat ctcaaacaat ataaaaaagc    660
tcttaggact aataatcctg aacagaggta gtaacatgca actgtatgca ttgcgaacta    720
cgcattttga tgacatgaca tgtcattaaa taatgaaaac agtcttgtgg taactagcta    780
tgttaccata acacaagaca tgtctaagta agatgagtct atgatataat aaatgagata    840
ttccataaaa ctagatataa gttactaccc actctgaaga tgataacaaa gaatagtaat    900
gcacgcatga caatacacta tttactagtc ttctgtaaat ttatccgatc aaaatggcct    960
gctcgggttg caatgcattc tcacgtgttg aagtttctga tatcgatgta aggtggtcat   1020
acaagacgag aataccaatg gagtactaga tctcgatgga ctaagcatat gcaaatttta   1080
tctgaacaag aagcaggctt actcaggttg caatgtattc tcacgtactg ttgccttgct   1140
ccagacgacc cgcatgcaaa agcgagcttg tcccctagag ttgtgaatac tagtttcatt   1200
agaaacatca cgtactgcga aagccattaa tgcctctgtg aacacaatcg ggcagtattg   1260
actagaatct ccaagatcag gccatgaaat tagttgttta cttgataata ttgtccaaga   1320
gttagggttt aggtcaagta gaggccgtgg cttttttcca tttctccata taaaagggc   1380 ttaggtcaag tagtagctgc ctatataaat gaggcattgc ggggttcctt actcacttgt   1440
gtgcattgac tgctaccagc tgtgtgctgg acactcgttc acagtgaacc agtcaggagg   1500
atttcaaatt cgtattcagg tatgcttgat tttagttttt aagtcatatg agttcatttt   1560
tagatcattt tttcatacga gagaaataag actagggcta ggtttgttct tcatatgggc   1620
cgggtgcaac atttcgataa caatcacgca tcagagctat tacttgttct tctgaatttt   1680
ctatagcctt taaaaaccga caatcagagt tcaattacca atctagtctt ggtcatattt   1740
tgtttcttaa tgaagtgttt ttgcttcact ttgtccttgt ggagtcgaat gtggcttcct   1800
gtttagactg ttagctaggt tcacccttc agatttcttc atactaatta tcttcatatt   1860
ctgccagtgt gaatcctcta gtcaataacg acatggcacc                         1900
```